(12) United States Patent
Seehra et al.

(10) Patent No.: US 12,269,858 B2
(45) Date of Patent: Apr. 8, 2025

(54) ACTIVIN RECEPTOR TYPE IIB VARIANTS AND METHODS OF USE THEREOF

(71) Applicant: Keros Therapeutics, Inc., Lexington, MA (US)

(72) Inventors: Jasbir S. Seehra, Lexington, MA (US); Jennifer Lachey, Lincoln, MA (US)

(73) Assignee: Keros Therapeutics, Inc., Lexington, MA (US)

( * ) Notice: Subject to any disclaimer, the term of this patent is extended or adjusted under 35 U.S.C. 154(b) by 0 days.

(21) Appl. No.: 18/407,929

(22) Filed: Jan. 9, 2024

(65) Prior Publication Data
US 2024/0141012 A1 May 2, 2024

Related U.S. Application Data

(60) Division of application No. 16/924,473, filed on Jul. 9, 2020, now Pat. No. 11,884,715, which is a continuation of application No. PCT/US2019/013329, filed on Jan. 11, 2019.

(60) Provisional application No. 62/702,747, filed on Jul. 24, 2018, provisional application No. 62/616,991, filed on Jan. 12, 2018.

(51) Int. Cl.
| | |
|---|---|
| *A61K 38/17* | (2006.01) |
| *A61P 9/12* | (2006.01) |
| *A61P 19/00* | (2006.01) |
| *A61P 21/00* | (2006.01) |
| *C07K 14/04* | (2006.01) |
| *C07K 14/47* | (2006.01) |
| *C07K 14/705* | (2006.01) |
| *C07K 14/71* | (2006.01) |
| *A61K 38/00* | (2006.01) |

(52) U.S. Cl.
CPC ........ *C07K 14/705* (2013.01); *A61K 38/1709* (2013.01); *A61K 38/179* (2013.01); *A61P 9/12* (2018.01); *A61P 19/00* (2018.01); *A61P 21/00* (2018.01); *C07K 14/04* (2013.01); *C07K 14/47* (2013.01); *C07K 14/71* (2013.01); *A61K 38/00* (2013.01); *C07K 2317/52* (2013.01)

(58) Field of Classification Search
CPC .. A61K 38/1709; A61K 38/179; C07K 14/47; C07K 14/71
See application file for complete search history.

(56) References Cited

U.S. PATENT DOCUMENTS

| | | | |
|---|---|---|---|
| 7,612,041 B2 | 11/2009 | Knopf et al. | |
| 7,709,605 B2 | 5/2010 | Knopf et al. | |
| 7,842,663 B2 | 11/2010 | Knopf et al. | |
| 7,947,646 B2 | 5/2011 | Sun et al. | |
| 7,951,771 B2 | 5/2011 | Knopf et al. | |
| 7,960,343 B2 | 6/2011 | Knopf et al. | |
| 7,988,973 B2 | 8/2011 | Sherman | |
| 8,007,809 B2 | 8/2011 | Sherman | |
| 8,058,229 B2 | 11/2011 | Seehra et al. | |
| 8,067,360 B2 | 11/2011 | Knopf et al. | |
| 8,067,562 B2 | 11/2011 | Han et al. | |
| 8,101,564 B2 | 1/2012 | Choi et al. | |
| 8,138,142 B2 | 3/2012 | Seehra et al. | |
| 8,173,601 B2 | 5/2012 | Knopf et al. | |
| 8,178,488 B2 | 5/2012 | Knopf et al. | |
| 8,216,997 B2 | 7/2012 | Seehra et al. | |
| 8,252,900 B2 | 8/2012 | Knopf et al. | |
| 8,293,881 B2 | 10/2012 | Seehra et al. | |
| 8,343,933 B2 | 1/2013 | Knopf et al. | |
| 8,361,957 B2 | 1/2013 | Seehra et al. | |
| 8,367,611 B2 | 2/2013 | Knopf et al. | |
| 8,501,768 B2 | 8/2013 | Conte et al. | |
| 8,614,292 B2 | 12/2013 | Han et al. | |
| 8,629,109 B2 | 1/2014 | Knopf et al. | |
| 8,703,927 B2 | 4/2014 | Seehra et al. | |
| 8,710,016 B2 | 4/2014 | Seehra et al. | |
| 8,716,459 B2 | 5/2014 | Sun et al. | |
| 8,871,209 B2 | 10/2014 | Stitt et al. | |
| 8,895,016 B2 | 11/2014 | Sherman et al. | |
| 8,999,917 B2 | 4/2015 | Sun et al. | |
| 9,138,459 B2 | 9/2015 | Knopf et al. | |
| 9,163,075 B2 | 10/2015 | Knopf et al. | |
| 9,181,533 B2 | 11/2015 | Seehra et al. | |

(Continued)

FOREIGN PATENT DOCUMENTS

| | | |
|---|---|---|
| AU | 2013204964 A1 | 5/2013 |
| AU | 2016250354 A1 | 11/2016 |

(Continued)

OTHER PUBLICATIONS

"A Phase 2 Study of Intravenous or Subcutaneous Dosing of Sotatercept (ACE-011) in Patients With End-Stage Kidney Disease on Hemodialysis," U.S. National Library of Medicine, <clinicaltrials.gov/ct2/show/NCT01999582?term=sotatercept&draw=2&rank=9>, first posted Dec. 3, 2013, retrieved on Mar. 30, 2020 (6 pages).
"A Phase IIa Study of Sotatercept on Bone Mass and Turnover in Patients With Multiple Myeloma," U.S. National Library of Medicine, <clinicaltrials.gov/ct2/show/NCT02230917?term=sotatercept&draw=2&rank=4>, first posted Sep. 3, 2014, retrieved Mar. 30, 2020 (7 pages).

(Continued)

*Primary Examiner* — Xiaozhen Xie
(74) *Attorney, Agent, or Firm* — Clark & Elbing LLP

(57) ABSTRACT

The invention features polypeptides that include an extracellular ActRIIB variant. In some embodiments, a polypeptide of the invention includes an extracellular ActRIIB variant fused to an Fc domain monomer or moiety. The invention also features pharmaceutical compositions and methods of using the polypeptides to treat diseases and conditions involving weakness and atrophy of muscles, bone damage, low red blood cell levels (e.g., anemia or blood loss), fibrosis, and/or pulmonary hypertension.

13 Claims, 20 Drawing Sheets
Specification includes a Sequence Listing.

(56) References Cited

U.S. PATENT DOCUMENTS

| | | |
|---|---|---|
| 9,273,114 B2 | 3/2016 | Sun et al. |
| 9,284,364 B2 | 3/2016 | Han et al. |
| 9,353,356 B2 | 5/2016 | Knopf et al. |
| 9,399,669 B2 | 7/2016 | Knopf et al. |
| 9,439,945 B2 | 9/2016 | Seehra et al. |
| 9,447,165 B2 | 9/2016 | Sun et al. |
| 9,493,556 B2 | 11/2016 | Seehra et al. |
| 9,505,813 B2 | 11/2016 | Seehra et al. |
| 9,526,759 B2 | 12/2016 | Knopf et al. |
| 9,572,865 B2 | 2/2017 | Knopf et al. |
| 9,610,327 B2 | 4/2017 | Sun et al. |
| 9,617,319 B2 | 4/2017 | Seehra et al. |
| 9,745,559 B2 | 8/2017 | Seehra et al. |
| 9,809,638 B2 | 11/2017 | Sun et al. |
| 9,850,298 B2 | 12/2017 | Attie |
| 9,932,379 B2 | 4/2018 | Seehra et al. |
| 10,093,707 B2 | 10/2018 | Sherman et al. |
| 10,131,700 B2 | 11/2018 | Seehra et al. |
| 10,189,882 B2 | 1/2019 | Attie et al. |
| 10,227,393 B2 | 3/2019 | Kumar et al. |
| 10,259,861 B2 | 4/2019 | Knopf et al. |
| 10,308,704 B2 | 6/2019 | Sun et al. |
| 10,358,476 B2 | 7/2019 | Kumar et al. |
| 10,358,633 B2 | 7/2019 | Seehra et al. |
| 10,377,996 B2 | 8/2019 | Seehra et al. |
| 10,407,487 B2 | 9/2019 | Sun et al. |
| 10,487,144 B2 | 11/2019 | Attie |
| 10,550,170 B2 | 2/2020 | Sherman et al. |
| 11,013,785 B2 | 5/2021 | Seehra et al. |
| 11,090,361 B2 | 8/2021 | Seehra et al. |
| 11,484,573 B2 | 11/2022 | Lachey et al. |
| 11,717,558 B2 | 8/2023 | Seehra et al. |
| 11,884,715 B2 | 1/2024 | Seehra et al. |
| 2006/0068468 A1 | 3/2006 | Knopf et al. |
| 2009/0005308 A1 | 1/2009 | Knopf et al. |
| 2009/0163417 A1 | 6/2009 | Sherman |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2010/0266591 A1 | 10/2010 | Bugelski et al. |
| 2010/0267133 A1 | 10/2010 | Knopf et al. |
| 2010/0316644 A1 | 12/2010 | Seehra et al. |
| 2011/0038831 A1 | 2/2011 | Seehra et al. |
| 2011/0092670 A1 | 4/2011 | Knopf et al. |
| 2011/0135638 A1 | 6/2011 | Seehra et al. |
| 2011/0250198 A1 | 10/2011 | Wolfman et al. |
| 2012/0015877 A1 | 1/2012 | Seehra et al. |
| 2012/0121576 A1 | 5/2012 | Seehra et al. |
| 2012/0148588 A1 | 6/2012 | Knopf et al. |
| 2013/0065299 A1 | 3/2013 | Knopf et al. |
| 2013/0071393 A1 | 3/2013 | Seehra et al. |
| 2013/0177559 A1 | 7/2013 | Seehra et al. |
| 2013/0288983 A1 | 10/2013 | Sun et al. |
| 2013/0315924 A1 | 11/2013 | Hsu et al. |
| 2014/0079700 A1 | 3/2014 | Knopf et al. |
| 2014/0314759 A1 | 10/2014 | Seehra et al. |
| 2015/0023970 A1 | 1/2015 | Seehra et al. |
| 2015/0023981 A1 | 1/2015 | De Kretser et al. |
| 2015/0030595 A1 | 1/2015 | Lee et al. |
| 2015/0183845 A1 | 7/2015 | Sherman et al. |
| 2016/0039922 A1 | 2/2016 | Attie |
| 2016/0108379 A1 | 4/2016 | Knopf et al. |
| 2016/0298093 A1 | 10/2016 | Kumar et al. |
| 2016/0333418 A1 | 11/2016 | Haqq |
| 2017/0058016 A1 | 3/2017 | Knopf et al. |
| 2017/0327800 A1 | 11/2017 | Seehra et al. |
| 2017/0360887 A1 | 12/2017 | Attie et al. |
| 2018/0050089 A1 | 2/2018 | Kumar et al. |
| 2018/0125928 A1 | 5/2018 | Attie et al. |
| 2018/0148491 A1 | 5/2018 | Han et al. |
| 2018/0161426 A1 | 6/2018 | Cappellini et al. |
| 2018/0334673 A1 | 11/2018 | Wood et al. |
| 2019/0085067 A1 | 3/2019 | Schurpf et al. |
| 2019/0151463 A1 | 5/2019 | Gegg et al. |
| 2019/0233486 A1 | 8/2019 | Attie et al. |
| 2019/0256605 A1 | 8/2019 | Han et al. |
| 2019/0282663 A1 | 9/2019 | Seehra et al. |
| 2019/0284251 A1 | 9/2019 | Seehra et al. |
| 2019/0330307 A1 | 10/2019 | Han et al. |
| 2019/0345225 A1 | 11/2019 | Seehra et al. |
| 2019/0352619 A1 | 11/2019 | Knopf et al. |
| 2020/0055919 A1 | 2/2020 | Kumar et al. |
| 2020/0071381 A1 | 3/2020 | Knopf et al. |
| 2020/0407415 A1 | 12/2020 | Seehra et al. |
| 2021/0030841 A1 | 2/2021 | Lachey et al. |
| 2021/0052698 A1 | 2/2021 | Seehra et al. |
| 2021/0275637 A1 | 9/2021 | Seehra et al. |
| 2023/0079602 A1 | 3/2023 | Seehra et al. |
| 2023/0087128 A1 | 3/2023 | Seehra et al. |
| 2023/0265162 A1 | 8/2023 | Seehra et al. |
| 2023/0348565 A1 | 11/2023 | Seehra et al. |

FOREIGN PATENT DOCUMENTS

| | | | |
|---|---|---|---|
| CN | 102131515 A | 7/2011 | |
| CN | 103298832 A | 9/2013 | |
| EP | 2314617 A2 | 4/2011 | |
| EP | 2303918 | 8/2012 | |
| EP | 2318028 | 8/2012 | |
| EP | 2594280 A1 | 5/2013 | |
| JP | 2008-507288 A | 3/2008 | |
| WO | WO-2004/039948 A2 | 5/2004 | |
| WO | WO-2006/012627 A2 | 2/2006 | |
| WO | WO-2006/012627 A3 | 5/2006 | |
| WO | WO-2008/076437 A2 | 6/2008 | |
| WO | WO-2008/094708 A2 | 8/2008 | |
| WO | WO-2008/097541 A2 | 8/2008 | |
| WO | WO-2008/100384 A2 | 8/2008 | |
| WO | WO-2009/015345 A1 | 1/2009 | |
| WO | WO-2009/158015 A2 | 12/2009 | |
| WO | WO-2009/158025 A2 | 12/2009 | |
| WO | WO-2009/158033 A2 | 12/2009 | |
| WO | WO-2009/158035 A2 | 12/2009 | |
| WO | WO-2009/158015 A3 | 3/2010 | |
| WO | WO-2010/062383 A2 | 6/2010 | |
| WO | WO-2010/083034 A1 | 7/2010 | |
| WO | WO-2010/151426 A1 | 12/2010 | |
| WO | WO-2011/020045 A1 | 2/2011 | |
| WO | WO-2011/031901 A1 | 3/2011 | |
| WO | WO-2011/056896 A1 | 5/2011 | |
| WO | WO-2011/063018 A1 | 5/2011 | |
| WO | WO-2012/027065 A2 | 3/2012 | |
| WO | WO-2012/064771 A1 | 5/2012 | |
| WO | WO-2013/059347 A1 | 4/2013 | |
| WO | WO-2013/188448 A3 | 4/2014 | |
| WO | WO-2014/066487 A2 | 5/2014 | |
| WO | WO-2014/138485 A1 | 9/2014 | |
| WO | WO-2014/144903 A1 | 9/2014 | |
| WO | WO-2015/143403 A1 | 9/2015 | |
| WO | WO-2015/161220 A1 | 10/2015 | |
| WO | WO-2015/192111 A1 | 12/2015 | |
| WO | WO-2015/192127 A2 | 12/2015 | |
| WO | WO-2016/069234 A1 | 5/2016 | |
| WO | WO-2016/090188 A1 | 6/2016 | |
| WO | WO-2016/164501 A1 | 10/2016 | |
| WO | WO-2016171948 A1 * | 10/2016 | ............ A61K 38/17 |
| WO | WO-2016/187378 A1 | 11/2016 | |
| WO | WO-2017/079591 A2 | 5/2017 | |
| WO | WO-2017/091706 A1 | 6/2017 | |
| WO | WO-2017/147182 A1 | 8/2017 | |
| WO | WO-2018/013936 A1 | 1/2018 | |
| WO | WO-2018/022762 A1 | 2/2018 | |
| WO | WO-2018/067740 A1 | 4/2018 | |
| WO | WO-2018/067874 A1 | 4/2018 | |
| WO | WO-2018/075747 A1 | 4/2018 | |
| WO | WO-2018/089702 A1 | 5/2018 | |
| WO | WO-2018/089706 A2 | 5/2018 | |
| WO | WO-2018/089715 A1 | 5/2018 | |
| WO | WO-2018/100483 A1 | 6/2018 | |
| WO | WO-2018/144542 A1 | 8/2018 | |
| WO | WO-2018/144968 A1 | 8/2018 | |
| WO | WO-2018/231905 A1 | 12/2018 | |
| WO | WO-2019/094751 A1 | 5/2019 | |
| WO | WO-2019/217715 A1 | 11/2019 | |

(56) References Cited

FOREIGN PATENT DOCUMENTS

| WO | WO-2021/062163 A1 | 4/2021 |
|---|---|---|
| WO | WO-2021/189006 A1 | 9/2021 |
| WO | WO-2021/189010 A1 | 9/2021 |
| WO | WO-2021/189019 A1 | 9/2021 |
| WO | WO-2022/072882 A1 | 4/2022 |
| WO | WO-2022/235620 A1 | 11/2022 |
| WO | WO-2022/271716 A2 | 12/2022 |
| WO | WO-2023/023345 A2 | 2/2023 |
| WO | WO-2024/054985 A2 | 3/2024 |
| WO | WO-2024/102906 A2 | 5/2024 |

OTHER PUBLICATIONS

"A Study of Sotatercept for the Treatment of Pulmonary Arterial Hypertension (PAH) (PULSAR)," U.S. National Library of Medicine, <clinicaltrials.gov/ct2/show/NCT03496207?term=sotatercept&draw=2&rank=3>, first posted Apr. 12, 2018, retrieved Mar. 30, 2020 (8 pages).

"A Study of Sotatercept for the Treatment of Pulmonary Arterial Hypertension (SPECTRA)," U.S. National Library of Medicine, <clinicaltrials.gov/ct2/show/NCT03738150?term=sotatercept&draw=2&rank=1>, first posted Nov. 13, 2018, retrieved on Mar. 30, 2020 (9 pages).

"Efficacy and Safety Study of Luspatercept (ACE-536) Versus Epoetin Alfa for the Treatment of Anemia Due to IPSS-R Very Low, Low or Intermediate Risk Myelodysplastic Syndromes (MDS) in ESA Naïve Subjects Who Require Red Blood Cell Transfusions (COMMANDS)," U.S. National Library of Medicine, <clinicaltrials.gov/ct2/show/NCT03682536?term=luspatercept&draw=2&rank=10>, first posted Sep. 24, 2018, retrieved Mar. 30, 2020 (13 pages).

"Safety and Efficacy Study of Sotatercept in Adults With Transfusion Dependent Diamond Blackfan Anemia (ACE-011-DBA)," U.S. National Library of Medicine, <clinicaltrials.gov/ct2/show/NCT01464164?term=sotatercept&draw=2&rank=2>, first posted Nov. 3, 2011, retrieved Mar. 30, 2020 (10 pages).

"Sotatercept in Treating Patients With Myeloproliferative Neoplasm-Associated Myelofibrosis or Anemia," U.S. National Library of Medicine, <clinicaltrials.gov/ct2/show/NCT01712308?term=sotatercept&draw=2&rank=8>, first posted Oct. 23, 2012, retrieved Mar. 30, 2020 (7 pages).

"Study of ACE-536 for the Treatment of Anemia in Patients With Myelodysplastic Syndromes (MDS)," U.S. National Library of Medicine, <clinicaltrials.gov/ct2/show/NCT01749514?term=luspatercept&draw=2&rank=12>, first posted Dec. 13, 2012, retrieved Mar. 30, 2020 (8 pages).

"Study of ACE-536 in Healthy Postmenopausal Women," U.S. National Library of Medicine, <clinicaltrials.gov/ct2/show/NCT01432717?term=luspatercept&draw=2&rank=13>, first posted Sep. 13, 2011, retrieved Mar. 30, 2020 (5 pages).

"Study of Sotatercept for the Treatment of Anemia in low-or Intermediate-1 Risk Myelodysplastic Syndromes (MDS) or Nonproliferative Chronic Myelomonocytic Leukemia (CMML)," U.S. National Library of Medicine, <clinicaltrials.gov/ct2/show/NCT01736683?term=sotatercept&draw=2&rank=5>, first posted Nov. 29, 2012, retrieved Mar. 30, 2020 (12 pages).

"Study to Evaluate Effect of a Single Dose of Sotatercept (ACE-011) on Red Blood Cell Mass and Plasma Volume in Subjects With Solid Tumors," U.S. National Library of Medicine, <clinicaltrials.gov/ct2/show/NCT01190644?term=sotatercept&draw=2&rank=7>, first posted Aug. 27, 2010, retrieved Mar. 30, 2020 (6 pages).

"Study to Evaluate the Effects of ACE-536 in Patients With Beta-thalassemia," U.S. National Library of Medicine, <clinicaltrials.gov/ct2/show/NCT01749540?term=luspatercept&draw=2&rank=11>, first posted Dec. 13, 2012, retrieved Mar. 30, 2020 (8 pages).

"To Determine Safe and Effective Dose of ACE-011 for the Treatment of Chemotherapy Induced Anemia in Patients With Advanced Non-small Cell Lung Cancer," U.S. National Library of Medicine, <clinicaltrials.gov/ct2/show/NCT01284348?term=sotatercept&draw=2&rank=6>, first posted Jan. 27, 2011, retrieved Mar. 30, 2020 (10 pages).

"To Document the Burden of Illness on the Quality of Life and the Impact on Healthcare Utilization in (Beta)-thalassemia Subjects Who Are Transfusion Dependent (TD) and Non-transfusion Dependent (NTD) Receiving Standard of Care," U.S. National Library of Medicine, <clinicaltrials.gov/ct2/show/NCT02626689?term=luspatercept&draw=2&rank=14>, first posted Dec. 10, 2015, retrieved Mar. 30, 2020 (9 pages).

Abdulkadyrov et al., "Sotatercept in Patients with Osteolytic Lesions of Multiple Myeloma," Br J Haematol. 165(6):814-823 (2014).

Akpan et al., "The effects of a soluble activin type IIB receptor on obesity and insulin sensitivity," available in PMC May 1, 2010, published in final edited form as: Int J Obes (Lond). 33(11):1265-73 (2009) (17 pages).

Attie et al., "A phase 1 study of ACE-536, a regulator of erythroid differentiation, in healthy volunteers," Am J Hematol. 89(7): 766-770 (2014) (5 pages).

Attie et al., "A single ascending-dose study of muscle regulator ACE-031 in healthy volunteers." Muscle Nerve. 47(3):416-23 (2013).

Badesch et al., "PULSAR: A Phase 2, Randomized, Double-Blind, Placebo-Controlled Study to Assess the Efficacy and Safety of Sotatercept (ACE-011) When Added to Standard of Care for the Treatment of Pulmonary Arterial Hypertension (PAH)," ERS International Congress Sep. 28-Oct. 2, 2019, Madrid, Spain, Poster PA4750, Abstract 19918, retrieved from <acceleronpharma.com/wp-content/uploads/2019/10/Badesch-et-al-ERS-2019-PULSAR-TIP-Poster_FINAL-2.pdf> (2019) (1 page).

Bernstein et al., "Activin Decoy Receptor ActRIIB:Fc Lowers FSH and Therapeutically Restores Oocyte Yield, Prevents Oocyte Chromosome Misalignments and Spindle Aberrations, and Increases Fertility in Midlife Female SAMP8 Mice," Endocrinology. 157(3):1234-47 (Mar. 2016).

Bond et al., "Modeling Energy Dynamics in Mice with Skeletal Muscle Hypertrophy Fed High Calorie Diets," Int J Biol Sci. 12(5):617-30 (Apr. 2016).

Cadena et al., "Administration of a soluble activin type IIB receptor promotes skeletal muscle growth independent of fiber type," J Appl Physiol. 109(3):635-642 (2010) (21 pages).

Campbell et al., "Myostatin inhibitor ACE-031 treatment of ambulatory boys with Duchenne muscular dystrophy: Results of a randomized, placebo-controlled clinical trial," Muscle Nerve. 55(4):458-464 (Apr. 2017).

Cappellini et al., "A Phase 2a, Open-Label, Dose-Finding Study To Determine The Safety and Tolerability Of Sotatercept (ACE-011) In Adults With Beta-Thalassemia: Interim Results," 55th Annual Meeting of the American Society of Hematology (ASH), Dec. 7-10, New Orleans, LA, Poster 3448 (2013) (1 page).

Cappellini et al., "The BELIEVE Trial: Results of a Phase 3, Randomized, Double-Blind, Placebo-Controlled Study of Luspatercept in Adult Beta-Thalassemia Patients Who Require Regular Red Blood Cell (RBC) Transfusions," 60th Annual Meeting of the American Society of Hematology (ASH), Dec. 1-4, San Diego CA, Oral Presentation, retrieved from <http://acceleronpharma.com/wp-content/uploads/2018/12/BELIEVE-ASH-2018-Oral-Presentation-for-upload.pdf> (Dec. 2018) (17 pages).

Carlson et al., "Soluble Activin Receptor Type IIB Increases Forward Pulling Tension in the MDX Mouse," available in PMC May 1, 2012, published in final edited form as: Muscle Nerve. 43(5):694-699 (2011) (11 pages).

Carrancio et al., "An activin receptor IIA ligand trap promotes erythropoiesis resulting in a rapid induction of red blood cells and haemoglobin," Br J Haematol. 165(6):870-882 (2014).

Cash et al., "The structure of myostatin:follistatin 288: insights into receptor utilization and heparin binding," EMBO J. 28(17):2662-76 (2009).

Chantry et al., "Inhibiting activin-A signaling stimulates bone formation and prevents cancer-induced bone destruction in vivo." J Bone Miner Res. 25(12):2633-46 (2010).

Chen et al., "Pharmacokinetics and Exposure-Response of Luspatercept in Patients With Anemia Due to Low- or Intermediate-1-Risk Myelodysplastic Syndromes (MDS): Preliminary Results From Phase 2 Studies," 58th Annual Meeting of the American Society of Hematology (ASH), Dec. 3-6, San Diego, California, Poster 1990,

(56) References Cited

OTHER PUBLICATIONS retrieved from <acceleronpharma.com/wp-content/uploads/2017/03/Chen-ASH-2016-Poster-Luspatercept-PK-MDS.pdf>, (Dec. 2016) (1 page).
Chen et al., "Pharmacokinetics and Exposure-Response of Luspatercept in Patients With Beta-Thalassemia: Preliminary Results From Phase 2 Studies," 58th Annual Meeting of the American Society of Hematology (ASH), Dec. 3-6, San Diego, CA, Poster 2463, retrieved from <acceleronpharma.com/wp-content/uploads/2017/03/20161204-Chen-ASH-2016-Poster-Luspatercept-PK-B-thal.pdf>, (Dec. 2016) (1 page).
Dellanna, "Safety and Hemoglobin Effect of Sotatercept, Administered Intravenously and Subcutaneously, for Maintenance of Hemoglobin in Hemodialysis Subjects: Interim Analysis of a Phase 2 Study," 48th Annual American Society of Nephrology Kidney Week, Nov. 3-8, San Diego, CA, retrieved from <acceleronpharma.com/wp-content/uploads/2017/03/20151106-ASN-2015_Sotatercept-REN-002-Oral-Presentation_10-22-15-v3-Final.pdf>, (2015) (14 pages).
DiGirolamo et al., "Administration of soluble activin receptor 2B increases bone and muscle mass in a mouse model of osteogenesis imperfecta," Bone Res. 3:14042 (2015) (6 pages).
Dussiot et al., "An activin receptor IIA ligand trap corrects ineffective erythropoiesis in beta-thalassemia," Nat Med. 20(4):398-407 (2014) (12 pages).
El-Shahawy et al., "Interim Analysis of ACE-011-REN-001: The First 28 Day Dose Cycle of Low and Medium Starting Doses of Sotatercept Compared to Placebo for Correction of Anemia in Hemodialysis Subjects," National Kidney Foundation (NKF) 2014 Spring Clinical Meeting, Apr. 22-26, Las Vegas, NV, retrieved from <acceleronpharma.com/wp-content/uploads/2017/03/20140423-NKF-2014_REN-001-Interim-Analysis-Poster_FINAL.pdf>, (2014) (7 pages).
El-Shahawy et al., "Long-term Effects of Sotatercept Compared With Placebo for Correction of Anemia in Hemodialysis Subjects: Interim Analysis of ACE-011-REN-001 Phase 2A Study," 51st Congress of the European Renal Association and European Dialysis and Transplant Association, May 31-Jun. 3, Amsterdam, Poster SP244, retrieved from <acceleronpharma.com/wp-content/uploads/2014/06/20140601-Long-Term-Effects-of-Sotatercept-Compared-with-Placebo-for-Correction-of-Anemia.pdf>, (2014) (7 pages).
El-Shahawy et al., "Safety and Hemoglobin Effect of the First 28-Day Dose Cycle of Sotatercept 0.7 mg/kg Compared With Lower Doses and Placebo for Correction of Anemia in Hemodialysis Subjects: Interim Analysis," American Society of Nephrology Kidney Week, Nov. 11-16, 2014, Philadelphia, PA. Poster, retrieved from <acceleronpharma.com/wp-content/uploads/2014/11/20141113-El-Shahawy-ASN-2014-Sotatercept-Safety-Poster.pdf>, (2014) (1 page).
Fajardo et al., "Treatment with a soluble receptor for activin improves bone mass and structure in the axial and appendicular skeleton of female cynomolgus macaques (*Macaca fascicularis*)," Bone. 46(1):64-71 (2010).
Fakhfakh et al., "Administration of a soluble activin type IIB receptor promotes the transplantation of human myoblasts in dystrophic mice," available in PMC Jul. 10, 2014, published in final edited form as: Cell Transplant. 21(7):1419-30 (2012) (19 pages).
Fenaux et al., "Assessment of Longer-Term Efficacy and Safety in the Phase 3, Randomized, Double-Blind, Placebo-Controlled MEDALIST Trial of Luspatercept to Treat Anemia in IPSS-R Very Low-, Low-, or Int-Risk RBC Transfusion-Dependent MDS with Ring Sideroblasts," 61st Annual Meeting of the American Society of Hematology (ASH), Dec. 7-10, Orlando, Florida, retrieved from <acceleronpharma.com/wp-content/uploads/2019/12/ASH-2019-MEDALIST-long-term-analysis-Fenaux-oral-7-Dec-2019V2.pdf>, (2019) (18 pages).
Fenaux et al., "Luspatercept in Patients with Lower-Risk Myelodysplastic Syndromes," N Engl J Med. 382(2):140-151 (Jan. 2020).
Fenaux et al., "The MEDALIST Trial: Results of a Phase 3, Randomized, Double-Blind, Placebo-Controlled Study of Luspatercept to Treat Patients With Very Low-, Low-, or Intermediate-Risk Myelodysplastic Syndromes (MDS) Associated Anemia With Ring Sideroblasts (RS) Who Require Red Blood Cell (RBC) Transfusions," 60th Annual Meeting of the American Society of Hematology (ASH), Dec. 1-4, San Diego, California, Oral Presentation (2018) (18 pages).
Fields et al., "Activin receptor antagonists for cancer-related anemia and bone disease," Exp Opin Invest Drugs. 22(1):87-101 (2013) (16 pages).
Garcia-Manero et al., "Hematologic Improvement-Neutrophil and -Platelet in the MEDALIST Trial: Multilineage Data from a Phase 3, Randomized, Double-Blind, Placebo-Controlled Study of Luspatercept to Treat Anemia in Patients with Very Low-, Low-, or Intermediate-Risk Myelodysplastic Syndromes with Ring Sideroblasts Who Require Red Blood Cell (RBC) Transfusions," 61st Annual Meeting of the American Society of Hematology (ASH), Dec. 7-10, Orlando, Florida, Abstract 4243 (2019) (1 page).
Gerds et al., "A Phase 2 Study of Luspatercept in Patients With Myelofibrosis-Associated Anemia," 61st Annual Meeting of the American Society of Hematology (ASH), Dec. 7-10, Orlando FL, Presentation, Abstract 557, retrieved from <acceleronpharma.com/wp-content/uploads/2019/12/Gerds-et-al.-Luspatercept-in-MF_ASH-2019-7-Dec-2019-FINAL-FOR-UPLOAD.pdf>, (2019) (13 pages).
Giagounidis et al., "Luspatercept Increases Hemoglobin and Reduces Transfusion Burden in Patients With Lower-Risk Myelodysplastic Syndromes (MDS): Long-Term Results From the Phase 2 PACE-MDS Study," 22nd European Hematology Association Congress, Jun. 22-25, Madrid, Spain, Abstract p. 666, retrieved from <acceleronpharma.com/wp-content/uploads/2017/06/EHA-2017-MDS-Poster-20Jun2017-FINAL.pdf>, (Jun. 2017) (1 page).
Giagounidis et al., "Luspatercept Treatment Leads to Long Term Increases in Hemoglobin and Reductions in Transfusion Burden in Patients with Low or Intermediate-1 Risk Myelodysplastic Syndromes (MDS): Preliminary Results from the Phase 2 PACE-MDS Extension Study," Presentation. (2015) (16 pages).
Goh et al., "Activin receptor type 2A (ACVR2A) functions directly in osteoblasts as a negative regulator of bone mass," J Biol Chem. 292(33):13809-13822 (Jun. 2017).
Graham et al., "A Soluble Activin Receptor IIB Fails to Prevent Muscle Atrophy in a Mouse Model of Spinal Cord Injury," J Neurotrauma. 33(12):1128-1135 (Jun. 2016).
Guo et al., "Myostatin inhibition in muscle, but not adipose tissue, decreases fat mass and improves insulin sensitivity," PLoS One. 4(3):e4937 (2009) (11 pages).
Guo et al., "Myostatin inhibition prevents diabetes and hyperphagia in a mouse model of lipodystrophy," Diabetes. 61(10):2414-23 (2012).
Havill et al., "Sotatercept Improves Anemia, Vascular Calcification, and Bone Loss in Patients With End-Stage Kidney Disease on Hemodialysis," American Society of Nephrology Kidney Week, Nov. 5-8, 2015, San Diego, CA, Poster TH-P0038, retrieved from <acceleronpharma.com/wp-content/uploads/2017/03/20151105-ASN-2015_Sotatercept-REN-001-Poster_10.20.15-Final-1.pdf>, (2015) (1 page).
International Search Report and Written Opinion for International Application No. PCT/US17/60960, mailed Aug. 9, 2018 (14 pages).
International Search Report and Written Opinion for International Application No. PCT/US17/60970, mailed Mar. 27, 2018 (15 pages).
International Search Report and Written Opinion for International Application No. PCT/US2018/060076, mailed Mar. 14, 2019 (18 pages).
International Search Report and Written Opinion for International Application No. PCT/US2019/013329, mailed May 13, 2019 (19 pages).
International Search Report and Written Opinion for International Application No. PCT/US2019/031573, mailed Sep. 17, 2019 (16 pages).
Joshi et al., "ActRIIA-Fc (Sotatercept) Reverses Pulmonary Vascular Remodeling to Attenuate Pulmonary Arterial Hypertension by Rebalancing Activin/BMP Signaling in a Preclinical Model," American Thoracic Society 2019 International Conference, May 17-22, Dallas, TX, Poster, retrieved from <acceleronpharma.com/wp-content/uploads/2019/06/Joshi-SR-et-al-ATS-2019-Poster-Sotatercept-Reverses-Pulmonary-Vascular-R...-1.pdf>, (2019) (1 page).

(56) References Cited

OTHER PUBLICATIONS

Joshi et al., "RAP-011, a Murine Ortholog of ACTRIIA-FC (Sotatercept), Improves Pulmonary Hemodynamics and Restores Right Ventricular Structure and Function in a Preclinical Model of Severe Angio-obliterative Pulmonary Arterial Hypertension," American Heart Association Scientific Session, Nov. 10-12, Chicago, Illinois, retrieved from <http://acceleronpharma.com/wp-content/uploads/2018/11/SRJ-AHA-2018-Poster.pdf>, (2018) (1 page).
Komrokji et al., "A Phase 2, Dose-Finding Study of Sotatercept (ACE-011) in Patients with Lower-Risk Myelodysplastic Syndromes or Non-Proliferative Chronic Myelomonocytic Leukemia and Anemia Requiring Transfusion," The 13th International Symposium on Myelodysplastic Syndromes, Apr. 29-May 2, Washington, D.C., retrieved from <http://acceleronpharma.com/wp-content/uploads/2017/03/20150429-Komrokji-MDS-001_MDSF-2015-presentation_29-April-2015_FINAL.pdf>, (2015) (21 pages).
Komrokji et al., "An Open-Label, Phase 2, Dose-Finding Study of Sotatercept (ACE-011) in Patients with Low or Intermediate (Int)-1-Risk Myelodysplastic Syndromes (MDS) or Non-Proliferative Chronic Myelomonocytic Leukemia (CMML) and Anemia Requiring Transfusion," 56th Annual Meeting of the American Society of Hematology (ASH), Dec. 6-9, San Francisco, California. Poster p. 3251 (2014) (1 page).
Lee et al., "Growth differentiation factor 11 signaling controls retinoic acid activity for axial vertebral development," available in PMC Nov. 1, 2011, published in final edited form as: Dev Biol. 347(1):195-203 (2010) (19 pages).
Lee et al., "Myostatin and the control of skeletal muscle mass," Curr Opin Genet Devel. 9(5):604-607 (1999).
Lee et al., "Regulation of muscle growth by multiple ligands signaling through activin type II receptors," Proc Natl Acad Sci U S A. 102(50):18117-18122 (2005).
Lee et al., "Regulation of myostatin activity and muscle growth," Proc Natl Acad Sci U S A. 98(16):9306-9311 (2001).
Lee et al., "Role of satellite cells versus myofibers in muscle hypertrophy induced by inhibition of the myostatin/activin signaling pathway," Proc Natl Acad Sci U S A. 109(35):E2353-60 (2012).
Lotinun et al., "A soluble activin receptor Type IIA fusion protein (ACE-011) increases bone mass via a dual anabolic-antiresorptive effect in Cynomolgus monkeys." Bone. 46(4):1082-8 (2010).
MacDonald et al., "Denervation atrophy is independent from Akt and mTOR activation and is not rescued by myostatin inhibition," first posted online on Feb. 6, 2014, published in final edited form as: Dis Model Mech. 7(4):471-81 (2014) (Author manuscript) (39 pages).
Malluche et al., "Sotatercept: Initial Signal-Seeking Quantitative Computed Tomography Results for Bone Mass and Vascular Calcification in Hemodialysis Subjects Treated With Escalating Doses: Interim Analysis of ACE-011-REN-001," American Society of Nephrology Kidney Week, Nov. 11-16, 2014, Philadelphia, PA, retrieved from <http://acceleronpharma.com/wp-content/uploads/2017/03/20141113-Malluche_ASN-2014_Sotatercept-Bone-Mass-VC-Poster_11-10-14-Final.pdf>, (2014) (1 page).
Malluche et al., "The Role of Activin Signaling in the Pathogenesis of Renal Osteodystrophy of CKD-MBD," 52nd ERA-EDTA Congress, May 28-31, London, United Kingdom, Poster FP406, retrieved from <acceleronpharma.com/wp-content/uploads/2017/03/20150529-ERA-2015_RAP-011-Bone-Histomorphometry-Poster_05.22.15-Final-for-QR-Code.pdf>, (2015) (1 page).
Martinez, "Luspatercept Inhibits pSmad2/3 Signaling and Promotes Erythroid Maturation Through a GATA1 Dependent Mechanism," 23rd European Hematology Association Congress, Jun. 14-17, Stockholm, Sweden, Oral Presentation, retrieved from <acceleronpharma.com/wp-content/uploads/2018/06/EHA2018PMFinal.pdf>, (2018) (25 pages).
Martinez, "RAP-536 (Murine ACE-536/Luspatercept) Inhibits Smad2/3 Signaling and Promotes Erythroid Differentiation By Restoring GATA1 Function in Murine Beta-thalassemia," 21st European Hematology Association Congress, Jun. 9-12, Copenhagen, Denmark, Oral Presentation, retrieved from <acceleronpharma.com/wp-content/uploads/2017/03/20160610-PedroEHA2016Final.pdf> (Jun. 2016) (23 pages).
Martinez, "RAP-536 (Murine ACE-536/Luspatercept) Inhibits Smad2/3 Signaling and Promotes Erythroid Differentiation By Restoring GATA1 Function in Murine Beta-thalassemia," Oral Presentation, Blood. 126(23):751 (2015) (25 pages).
McPherron et al., "Double muscling in cattle due to mutations in the myostatin gene," Proc Natl Acad Sci USA. 94(23):12457-61 (1997).
McPherron et al., "GDF-3 and GDF-9: two new members of the transforming growth factor-beta superfamily containing a novel pattern of cysteines," J Biol Chem. 268(5):3444-3449 (1993) (7 pages).
McPherron et al., "Redundancy of myostatin and growth/differentiation factor 11 function," BMC Dev Biol. 9:24 (2009) (9 pages).
McPherron et al., "Regulation of anterior/posterior patterning of the axial skeleton by growth/differentiation factor 11," Nat Genet. 22(3):260-264 (1999).
McPherron et al., "Regulation of skeletal muscle mass in mice by a new TGF-beta superfamily member," Nature. 387(6628):83-90 (1997).
McPherron et al., "Soluble activin receptor type IIB treatment does not cause fat loss in mice with diet-induced obesity," available in PMC Mar. 1, 2013, published in final edited form as: Diabetes Obes Metab. 14(3):279-82 (2012) (6 pages).
McPherron et al., "Suppression of body fat accumulation in myostatin-deficient mice," J Clin Invest. 109(5):595-601 (2002).
McPherron et al., "The transforming growth factor beta superfamily," Growth Factors and Cytokines in Health and Disease. 1:357-393 (1996).
Mesa et al., "A Phase 2, Multicenter, Open-Label Study of the Safety and Efficacy of Luspatercept in Subjects With Myeloproliferative Neoplasm (MPN)-Associated Myelofibrosis and Anemia With or Without RBC Transfusion Dependence," American Society of Clinical Oncology (ASCO) Annual Meeting, Jun. 1-5, Chicago Illinois, Poster TPS7083, retrieved from <http://acceleronpharma.com/wp-content/uploads/2018/06/Mesa-MF-TiP-ASCO-2018-Poster-May-24-2018_FINAL-1.pdf>, (2018) (1 page).
Morine et al., "Activin IIB receptor blockade attenuates dystrophic pathology in a mouse model of Duchenne muscular dystrophy," available in PMC Jul. 17, 2015, published in final edited form as: Muscle Nerve. 42(5):722-30 (2010) (17 pages).
Nagy et al., "Electrical impedance myography as a biomarker of myostatin inhibition with ActRIIB-mFc: a study in wild-type mice," Future Sci OA. 04(06):FSO308 (Apr. 2018) (10 pages).
Nielsen et al., "Postnatal Hyperplasic Effects of ActRIIB Blockade in a Severely Dystrophic Muscle," J Cell Physiol. 232(7):1774-1793 (Nov. 2016) (21 pages).
Paulson, "Targeting a new regulator of erythropoiesis to alleviate anemia," Nat Med. 20(4):334-335 (2014).
Pearsall et al., "A soluble activin type IIA receptor induces bone formation and improves skeletal integrity," Proc Nat Acad Sci U S A. 105(19):7082-7087 (2008).
Piga et al., "Improvements in Hemoglobin, Quality of Life, and Six-Minute-Walk Distance in Adults with beta-Thalassemia Treated with Luspatercept: Long-Term Phase 2 Study," 23rd European Hematology Association Congress, Jun. 14-17, Stockholm, Sweden, Oral Presentation, retrieved from <acceleronpharma.com/wp-content/uploads/2018/06/Piga-et-al-EHA-2018-Presentation-Improvements-in-Hemoglobin-Quality-of-Life-and-Six-Minute-Walk-Distance.pdf>, (2018) (22 pages).
Piga et al., "Luspatercept (ACE-536) Increases Hemoglobin and Decreases Transfusion Burden and Liver Iron Concentration in Adults with Beta-Thalassemia: Preliminary Results from a Phase 2 Study," EHA (2015) (22 pages).
Piga et al., "Luspatercept (ACE-536) Increases Hemoglobin and Decreases Transfusion Burden and Serum Ferritin in Adults with Beta-Thalassemia: Preliminary Results from a Phase 2 Study," American Society of Hematology, Oral Presentation, dated Dec. 7, 2014 (21 pages).
Piga et al., "Luspatercept Decreases Transfusion Burden and Liver Iron Concentration in Regularly Transfused Adults with Beta-

(56) References Cited

OTHER PUBLICATIONS

Thalassemia," 21st European Hematology Association Congress, Jun. 9-12, Copenhagen, Denmark, Presentation, retrieved from <acceleronpharma.com/wp-content/uploads/2017/03/20160612-EHA-2016-Luspatercept-Thal-TD-FINAL.pdf>, (Jun. 2016) (15 pages).

Piga et al., "Luspatercept improves hemoglobin levels and blood transfusion requirements in a study of patients with beta-thalassemia," Blood. 133(12):1279-1289 (Mar. 2019).

Platzbecker et al., "Luspatercept Increases Hemoglobin and Reduces Transfusion Burden in Patients with Low-Intermediate Risk Myelodysplastic Syndromes (MDS): Long-Term Results From Phase 2 PACE-MDS Study," 21st European Hematology Association Congress, Jun. 9-12, Copenhagen, Denmark, Presentation, retrieved from <http://acceleronpharma.com/wp-content/uploads/2017/03/20160610-EHA-2016-Luspatercept-MDS-FINAL.pdf> (Jun. 2016) (16 pages).

Piga et al., "Luspatercept Increases Hemoglobin, Decreases Transfusion Burden, and Improves Patient-Reported Outcomes in Adults with Beta-Thalassemia," 58th Annual Meeting of the American Society of Hematology (ASH), Dec. 3-6, San Diego, California, Oral Presentation, retrieved from <http://acceleronpharma.com/wp-content/uploads/2017/03/20161205-Luspatercept-Increases-Hemoglobin.pdf>, (Dec. 2016) (21 pages).

Piga et al., "Luspatercept Increases Hemoglobin, Reduces Liver Iron Concentration and Improves Quality of Life in Non-Transfusion Dependent Adults with Beta-Thalassemia," 21st European Hematology Association Congress, Jun. 9-12, Copenhagen, Denmark, Abstract p. 758, retrieved from <http://acceleronpharma.com/wp-content/uploads/2017/03/20160611-EHA-2016-Luspatercept-BThal-NTD-poster-FINAL.pdf>, (Jun. 2016) (1 page).

Piga et al., "Luspatercept Increases Hemoglobin, Reduces Liver Iron Concentration and Improves Quality of Life in Non-Transfusion Dependent Adults with Beta-Thalassemia," 2nd MEGMA Conference, Nov. 11-12, Amman, Jordan, retrieved from <http://acceleronpharma.com/wp-content/uploads/2017/03/20161111-TIF-2016-Luspatercept-BThal-NTD-poster_FINAL_16-10-31.pdf>, (Nov. 2016) (1 page).

Platzbecker et al., "Biomarkers of Ineffective Erythropoiesis Predict Response to Luspatercept in Patients with Low or Intermediate-1 Risk Myelodysplastic Syndromes (MDS): Final Results from the Phase 2 PACE-MDS Study," 57th American Society of Hematology Annual Meeting and Exposition, Dec. 5-8, Orlando, FL, Abstract 2862, retrieved from <Biomarkers of Ineffective Erythropoiesis Predict Response to Luspatercept in Patients with Low or Intermediate-1 Risk Myelodysplastic Syndromes (MDS): Final Results from the Phase 2 PACE-MDS Study>, (2015) (1 page).

Platzbecker et al., "Luspatercept (ACE-536) Increases Hemoglobin and Reduces Transfusion Burden in Patients with Low or Intermediate-1 Risk Myelodysplastic Syndromes (MDS): Preliminary Results from a Phase 2 Study," American Society of Hematology, Oral Presentation (2014) (21 pages).

Platzbecker et al., "Luspatercept for the treatment of anaemia in patients with lower-risk myelodysplastic syndromes (PACE-MDS): a multicentre, open-label phase 2 dose-finding study with long-term extension study," Lancet Oncol. 18(10): p. 1338-1347 (Sep. 2017).

Platzbecker et al., "Luspatercept Increases Hemoglobin And Reduces Transfusion Burden In Patients With Low Or Intermediate-1 Risk Myelodysplastic Syndromes (MDS): Preliminary Results From A Phase 2 Study," EHA MDS Oral Presentation, Jun. 13, 2015 (16 pages).

Platzbecker et al., "Luspatercept Increases Hemoglobin And Reduces Transfusion Burden In Patients With Low Or Intermediate-1 Risk Myelodysplastic Syndromes (MDS): Preliminary Results From A Phase 2 Study," Advancing Research & Patient Care, The 13th International Symposium on Myelodyplastic Syndromes, Washington, D.C., Apr. 19-May 2, 2015 (15 pages).

Platzbecker et al., "Luspatercept Response in New Subpopulations of Patients With Lower-Risk Myelodysplastic Syndromes (MDS): Update of the PACE Study," 14th International Symposium on Myelodysplastic Syndromes, May 3-6, Valencia, Spain, Oral Presentation, retrieved from <acceleronpharma.com/wp-content/uploads/2017/05/Platzbecker-U-MDS-Symposium-2017-Slides-Luspatercept-Response-in-New-Subpopulations-Website-Version.pdf>, (May 2017) (16 pages).

Platzbecker et al., "Luspatercept Significantly Reduces Red Blood Cell (RBC) Transfusion Burden, Regardless of Gene Mutation Frequency, Spectrum, and Prognostic Significance, Among Patients with Lower-Risk Myelodysplastic Syndromes Enrolled in the MED-ALIST Trial," retrieved from <http://acceleronpharma.com/wp-content/uploads/2019/12/ASH-2019-Platzbecker-MEDALIST-Mutational-analysis.pdf>, (2019) (1 page).

Platzbecker et al., "Mutational and Subgroup Analyses of Lower-Risk Myelodysplastic Syndromes (MDS) Patients Treated With Luspatercept: Phase 2 PACE-MDS Study," 23rd European Hematology Association Congress, Jun. 14-17, Stockholm, Sweden, Abstract p. F498, retrieved from <http://acceleronpharma.com/wp-content/uploads/2018/06/EHA-2018-MDS-Poster-06June2018.pdf>, (2018) (1 page).

Platzbecker et al., "Mutational Profile and Analysis of Lower-Risk Myelodysplastic Syndromes (MDS) Patients Treated with Luspatercept: Phase 2 PACE-MDS Study," American Society of Hematology (ASH) 59th Annual Meeting & Exposition, Dec. 9-12, Atlanta, GA, Abstract 2982, retrieved from <acceleronpharma.com/wp-content/uploads/2017/12/Platzbecker-U-ASH-2017-MDS-Luspatercept-Poster-Final.pdf> (Dec. 2017) (1 page).

Platzbecker et al., "Erythropoietic cellular analyses in luspatercept-treated lower-risk myelodysplastic syndromes (MDS): Phase 2 PACE-MDS study," 2018 American Society of Clinical Oncology (ASCO) Annual Meeting, Jun. 1-5, Chicago, Illinois, Abstract 7018, retrieved from <http://acceleronpharma.com/wp-content/uploads/2018/06/Platzbecker-ASCO-2018-Poster-Erythropoietic-Cellular-Analyses-Ph-2-PACE-MDS-Study-1.pdf>, (2018) (1 page).

Porter et al., "Effects of Luspatercept on Iron Overload and Impact on Responders to Luspatercept: Results from the BELIEVE Trial," 61st Annual Meeting of the American Society of Hematology (ASH), Abstract 2245, Blood. 134(Supplement 1):2245 (Dec. 2019) (1 page).

Raftopoulos et al., "Sotatercept (ACE-011) for the treatment of chemotherapy-induced anemia in patients with metastatic breast cancer or advanced or metastatic solid tumors treated with platinum-based chemotherapeutic regimens: results from two phase 2 studies," Support Care Cancer. 24(4):1517-25 (2015).

Ruckle et al., "Single-Dose, Randomized, Double-Blind, Placebo-Controlled Study of ACE-011 (ActRIIA-IgG1) in Postmenopausal Women," J Bone Mineral Res. 24(4):744-752 (2009).

Sako et al., "Characterization of the ligand binding functionality of the extracellular domain of activin receptor Type IIB," J Biol Chem. 285(27):21037-48 (2010).

Sanchez et al., "Evaluation of Electrical Impedance as a Biomarker of Myostatin Inhibition in Wild Type and Muscular Dystrophy Mice," PLoS One. 10(10):e0140521 (2015) (14 pages).

Sherman et al., "Multiple-Dose, Safety, Pharmacokinetic, and Pharmacodynamic Study of Sotatercept (ActRIIA-IgG1), a Novel Erythropoietic Agent, in Healthy Postmenopausal Women," J Clin Pharmacol. 53(11):1121-1130 (2013).

Smith et al., "Long-term Effects of Sotatercept Compared With Placebo for Correction of Anemia in Hemodialysis Subjects: Interim Analysis of ACE-011-REN-001," 52nd ERA-EDTA Congress, May 28-31, London, UK, Poster FP661, retrieved from <http://acceleronpharma.com/wp-content/uploads/2017/03/20150529-ERA-2015_Sotatercept-Hb-Safety-Poster_05.22.15-Final-for-QR-Code-1.pdf>, (2015) (1 page).

Smith et al., "Quantitative Computed Tomography Results for Bone Mass and Abdominal Aortic Vascular Calcification in Hemodialysis Subjects Treated With Escalating Dose Levels of Sotatercept: Interim Analysis of ACE-011-REN-001," 52nd ERA-EDTA Congress, May 28-31, London, UK, Poster SP645, retrieved from <acceleronpharma.com/wp-content/uploads/2017/03/20150530-ERA-2015_Sotatercept-QCT-Poster_05.22.15-Final-for-QR-Code.pdf>, (2015) (1 page).

Sunada, "Anti-myostatin antibody therapy for myopathies," Clin Neurol. 51:1157-1159 (2011) (3 pages) (English abstract included).

(56) References Cited

OTHER PUBLICATIONS

Sunada, "Myostatin Blockade Therapy for Muscular Atrophy," Brain Nerve. 63(11):1271-7 (2011) (Abstract only) (2 pages).
Suragani et al., "Modified activin receptor IIB ligand trap mitigates ineffective erythropoiesis and disease complications in murine beta-thalassemia," Blood. 123(25):3864-3872 (2014).
Suragani et al., "Modified ActRIIB-Fc Fusion Protein (ACE-536) Decreases Irreversible Sickle Cells in a Murine Model of Sickle Cell Disease," EHA, Poster p. 535, retrieved from <acceleronpharma.com/wp-content/uploads/2017/03/20140614-ACE-536-20140613-Modified-ActRIIB-Fc-Fusion-Protein-Decreases-Irreversible-Sickle-Cells-in-a-Murine-Model-of-1.pdf>, (2014) (1 page).
Suragani et al., "Modified ActRIIB-mFc Fusion Protein (murine ortholog of Luspatercept) Mitigates Sickling and Red Cell Pathology in a Murine Model of Sickle Cell Disease," ASH 56th Annual Meeting, Dec. 6-9, San Francisco, California. Poster 4055 (2014) (1 page).
Suragani et al., "Transforming growth factor-beta superfamily ligand trap ACE-536 corrects anemia by promoting late-stage erythropoiesis," Nat Med. 20(4):408-414 (2014) (10 pages).
Thevis et al., "Emerging drugs affecting skeletal muscle function and mitochondrial biogenesis—Potential implications for sports drug testing programs," Rapid Commun Mass Spectrom. 30(5):635-51 (Jan. 2016).
Tomillero et al., "Gateways to Clinical Trials," Methods Find Exp Clin Pharmacol. 32(1):47-86 (2010).
Townson et al., "Specificity and Structure of a High Affinity Activin Receptor-like Kinase 1 (ALK1) Signaling Complex," J Biol Chem. 287(33):27313-27325 (2012).
Vallet et al., "Activin A promotes multiple myeloma-induced osteolysis and is a promising target for myeloma bone disease," Proc Nat Acad Sci. 107(11):5124-9 (2010).
Viprakasit et al., "Evaluating Luspatercept Responders in the Phase 3, Randomized, Double-Blind, Placebo-Controlled BELIEVE Trial of Luspatercept in Adult beta-Thalassemia Patients Who Require Regular Red Blood Cell Transfusions," Blood. 134(Supplement 1):3545 (Dec. 2019) (1 page).
Wagner et al., "Loss of myostatin attenuates severity of muscular dystrophy in mdx mice," Ann Neurol. 52(6):832-6 (2002).
Wang et al., "A soluble activin receptor Type IIB does not improve blood glucose in streptozotocin-treated mice," Int J Biol Sci. 11(2):199-208 (2015).
Wang et al., "Myostatin inhibition induces muscle fibre hypertrophy prior to satellite cell activation," J Physiol. 590(9):2151-65 (2012).
Wolfman et al., "Activation of latent myostatin by the BMP-1/tolloid family of metalloproteinases," Proc Nat Acad Sci. 100(26):15842-6 (2003).
Yee et al., "Phase 1 Dose-Escalation Study of Sotatercept (ACE-011) in Combination with Lenalidomide and Dexamethasone in Patients with Relapsed and/or Refractory Multiple Myeloma," Headache. 1:0 (2015) (1 page).
Yu, "Sotatercept for rebalancing BMP/TGF-beta/activin signaling in PAH," Scientific Sessions Presentation (Nov. 2018) (12 pages).
Yung et al., "ACTRIIA-Fc rebalances BMP and activin/TGF-beta signaling to attenuate experimental pulmonary hypertension," American Heart Association Scientific Session, Nov. 11-15, Anaheim, CA, retrieved from <acceleronpharma.com/wp-content/uploads/2017/11/Dr.-Yu-Presentation-AHA-17-1.pdf>, (Nov. 2017) (15 pages).
Yung, "ACTRIIA-Fc Rebalances Activin/GDF and BMP9 Signaling to Attenuate Experimental Pulmonary Hypertension," American Heart Association Scientific Session, Nov. 10-12, Chicago, Illinois, retrieved from <acceleronpharma.com/wp-content/uploads/2018/11/Lai-Ming-AHA-2018-ActRIIa-Fc-v2-final.pdf>, (2018) (14 pages).
Zimmers et al., "Induction of Cachexia in Mice by Systemically Administered Myostatin," Science. 296(5572):1486-8 (2002) (4 pages).
Ngo et al., Computational Complexity, Protein Structure Prediction, and the Levinthal Paradox. The Protein Folding Problem and Tertiary Structure Prediction. Birkhäuser Boston, pp. 433, 492-495 (1994).
Wells, "Additivity of mutational effects in proteins," Biochemistry. 29(37):8509-17 (1990).
"Keros Therapeutics Presents Results from Preclinical Studies Investigating KER-012 at the American Society for Bone and Mineral Research 2020 Annual Meeting," Keros Therapeutics, <https://www.globenewswire.com/news-release/2020/09/11/2092586/0/en/Keros-Therapeutics-Presents-Results-from-Preclinical-Studies-Investigating-KER-012-at-the-American-Society-for-Bone-and-Mineral-Research-2020-Annual-Meeting.html>, dated Sep. 11, 2020, retrieved on Feb. 25, 2021 (4 pages).
Marisavljevic et al., "Myelofibrosis in primary myelodysplastic syndromes: clinical and biological significance," Med Oncol. 21(4):325-31 (2004) (Abstract only) (2 pages).
Morgenroth et al., "Insights into bone health in Duchenne muscular dystrophy," Bonekey Rep. 1:9 (2012) (11 pages).
International Search Report and Written Opinion for International Application No. PCT/US2021/023353, mailed Jul. 20, 2021 (9 pages).
International Search Report and Written Opinion for International Application No. PCT/US2021/023335, mailed Jul. 9, 2021 (29 pages).
International Search Report and Written Opinion for International Application No. PCT/US2021/023339, mailed Jun. 21, 2021 (23 pages).
Kuo et al., "MB109 as bioactive human bone morphogenetic protein-9 refolded and purified from E. coli inclusion bodies," Microb Cell Fact. 13(1):29 (2014) (13 pages).
Wu et al., "Identification and analysis of type II TGF-beta receptors in BMP-9-induced osteogenic differentiation of C3H10T1/2 mesenchymal stem cells," Acta Biochim Biophys Sin (Shanghai). 42(10):699-708 (2010).
International Search Report and Written Opinion for International Application No. PCT/US2021/053239, mailed Feb. 23, 2022 (13 pages).
Rodgarkia-Dara et al., "The activin axis in liver biology and disease," Mutat Res. 613(2-3):123-37 (2006).
Ballen et al., "Outcome of transplantation for myelofibrosis," Biol Blood Marrow Transplant. 16(3):358-67 (Mar. 2010).
Stegelmann et al., "Updated Results from the German Mpnsg-0212 Combination Trial: Ruxolitinib Plus Pomalidomide in Myelofibrosis with Anemia," Blood. 134(Supplement_1):672 (5 pages) (Nov. 2019).
Bose et al. "Management of Myelofibrosis-Related Cytopenias," Curr Hematol Malig Rep. 13(3):164-172 (May 2018).
International Search Report and Written Opinion for International Application No. PCT/US2022/040920, dated Mar. 29, 2023 (13 pages).
International Search Report and Written Opinion for International Application No. PCT/US2022/034366, mailed Jan. 4, 2023 (13 pages).
Humeniuk et al., "Brief Report: Loss of p15Ink4b Accelerates Development of Myeloid Neoplasms in Nup98-HoxD13 Transgenic Mice," Stem Cells. 32(5):1361-1366 (2014).
Park et al., "The prognostic value of serum erythropoietin in patients with lower-risk myelodysplastic syndromes: a review of the literature and expert opinion." Ann Hematol. 99(1):7-19 (Jan. 2020).
Feigenson et al., "Ker-050, a Modified Actriia Ligand Trap, Alleviates Cytopenia Arising from Multiple Etiologies," Blood. 136(Supplement_1):38 (2 Pages) (Nov. 2020).
International Search Report and Written Opinion for International Application No. PCT/US2022/027399, mailed Sep. 21, 2022 (14 pages).
Fenaux et al., "Luspatercept for the treatment of anemia in myelodysplastic syndromes and primary myelofibrosis," Blood. 133(8):790-794 (Feb. 2019) (5 pages).
Tournier et al., "Calibrated automated thrombography demonstrates hypercoagulability in patients with idiopathic pulmonary arterial hypertension," Thrombosis Res. 126:e418-e422 (2010) (5 pages).
Rabinovitch et al., "Inflammation and Immunity in the Pathogenesis of Pulmonary Arterial Hypertension," Circ Res. 115(1):165-175 (Jun. 2014) (11 pages).
Highland et al., "Development of the Pulmonary Hypertension Functional Classification Self-Report: a patient version adapted

(56) References Cited

OTHER PUBLICATIONS from the World Health Organization Functional Classification measure," Health Qual Life Outcomes. 19(1):202 (Aug. 2021) (13 pages).
Hoffmann et al., "Compartment-specific expression of collagens and their processing enzymes in intrapulmonary arteries of IPAH patients," Am J Physiol Lung Cell Mol Physiol. 308(10):L1002-L1013 (2015) (12 pages).
Bauer et al., "Complement C3 Deficiency Attenuates Chronic Hypoxia-Induced Pulmonary Hypertension in Mice," PLoS ONE 6(12):e28578 (Dec. 2011) (10 pages).
Ogawa et al., "Long-term patient survival with idiopathic/heritable pulmonary arterial hypertension treated at a single center in Japan," Life Science 118(2):414-419 (2014) (6 pages).
Galiè et al., "2015 ESC/ERS Guidelines for the diagnosis and treatment of pulmonary hypertension: The Joint Task Force for the Diagnosis and Treatment of Pulmonary Hypertension of the European Society of Cardiology (ESC) and the European Respiratory Society (ERS): Endorsed by: Association for European Paediatric and Congenital Cardiology (AEPC), International Society for Heart and Lung Transplantation (ISHLT)," European Heart Journal. 37:67-119 (Jan. 2016) (58 pages).
Huertas et al., "Immune Dysregulation and Endothelial Dysfunction in Pulmonary Arterial Hypertension: a complex interplay," Circulation. 129(12):1332-40 (Mar. 2014) (9 pages).
Yndestad et al., "Elevated levels of activin A in clinical and experimental pulmonary hypertension," J Appl Physiol 106(4):1356-1364 (2009) (9 pages).
Langdon et al., "RAP-011, an activin receptor ligand trap, increases hemoglobin concentration in Hepcidin transgenic mice," Am J. Hematol. 90(1): 8-14 (Jan. 2015) (18 pages).
Mulivor et al., "RAP-011, a Soluble Activin Receptor Type IIa Murine IgG-Fc Fusion Protein, Prevents Chemotherapy Induced Anemia," Blood. 114(22):161 (Nov. 2009) (2 pages).
"Hybrid human mutant activin IIB receptor hu-ActRIIB-ECD, SEQ ID 114.", retrieved from EBI accession No. GSP:BDH87204, dated Dec. 15, 2016 (1 page).
"Human ActRII extracellular region chimera, SEQ ID 174.", retrieved from EBI accession No. GSP:BKX55865, dated May 19, 2022 (1 page).
International Search Report and Written Opinion for PCT/US2023/079222, dated Apr. 19, 2024 (18 pages).
Lema et al., "P.127KER-050, a novel muscle anabolic, functions as a ligand trap that binds myo-catabolic TGFß ligands and has reduced binding affinity for BMP9, a critical vascular remodeling ligand," Neuromuscular Disorders. 29:Abstract p. 127 (Sep. 2019) (1 page).
Morrell et al., "Targeting BMP signalling in cardiovascular disease and anaemia," Nat Rev Cardiol. 13(2):106-20 (with supplemental material) (2016) (32 pages).
Paddock and O'Meara, "Steps toward therapeutically targeting the activin type II receptor for treating heart failure," Am J Physiol Heart Circ Physiol. 318:H326-H328 (Jan. 2020) (3 pages).
Roh et al., "Activin type II receptor signaling in cardiac aging and heart failure," Sci. Transl. Med. 11, eaau8680 (Mar. 2019) (15 pages).
Hardy et al., "The activin A antagonist follistatin inhibits cystic fibrosis-like lung inflammation and pathology," Immunology and Cell Biology 93:567-574 (Mar. 2015) (8 pages).
Farrell et al., "Bisphosphonate conjugation for bone specific drug targeting," Bone Reports 9:47-60 (Jul. 2018) (14 pages).
Fabre et al., "Anti-Sclerostin Antibodies in Osteoporosis and Other Bone Diseases," J. Clin. Med. 9, 3439 (Oct. 2020) (16 pages).
Ralston and Gaston, "Management of Osteogenesis Imperfecta," Frontier in Endocrinology 10, 924 (Feb. 2020) (10 pages).
Jiang et al. "Activin A as a Novel Chemokine Induces Migration of L929 Fibroblasts by ERK Signaling in Microfluidic Devices," Frontiers in Cell and Developmental Biology 9, 660316 (May 2021) (11 pages).

* cited by examiner

FIG. 1

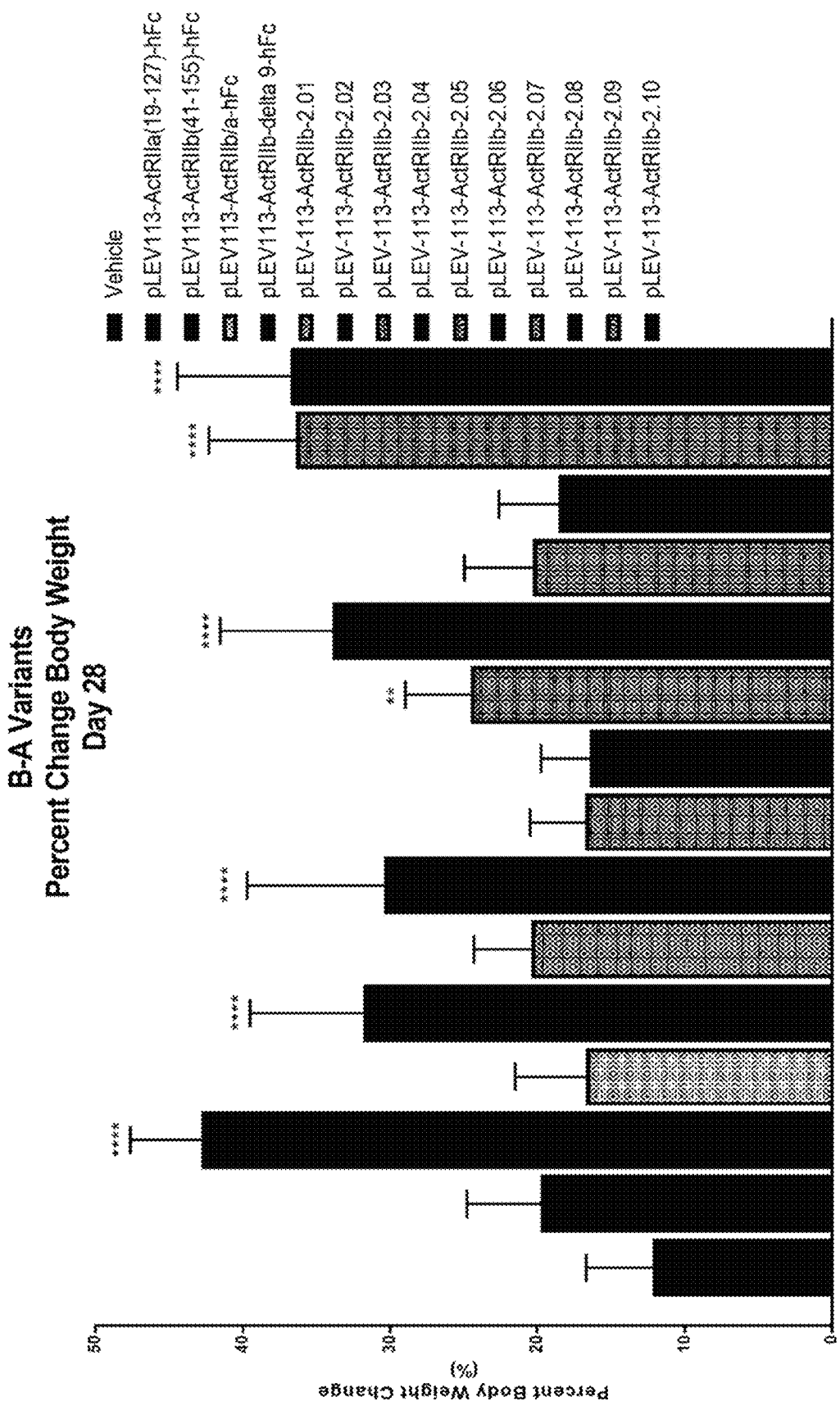

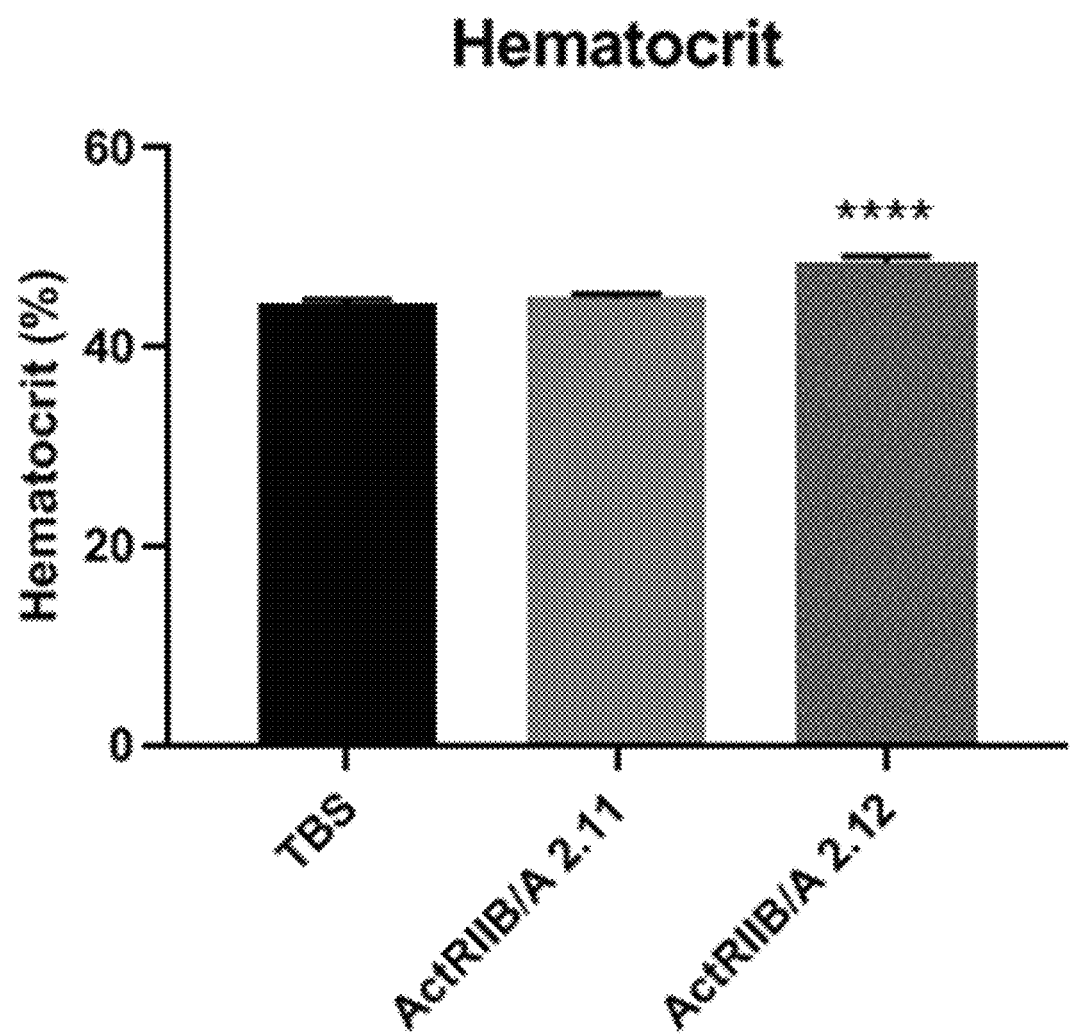

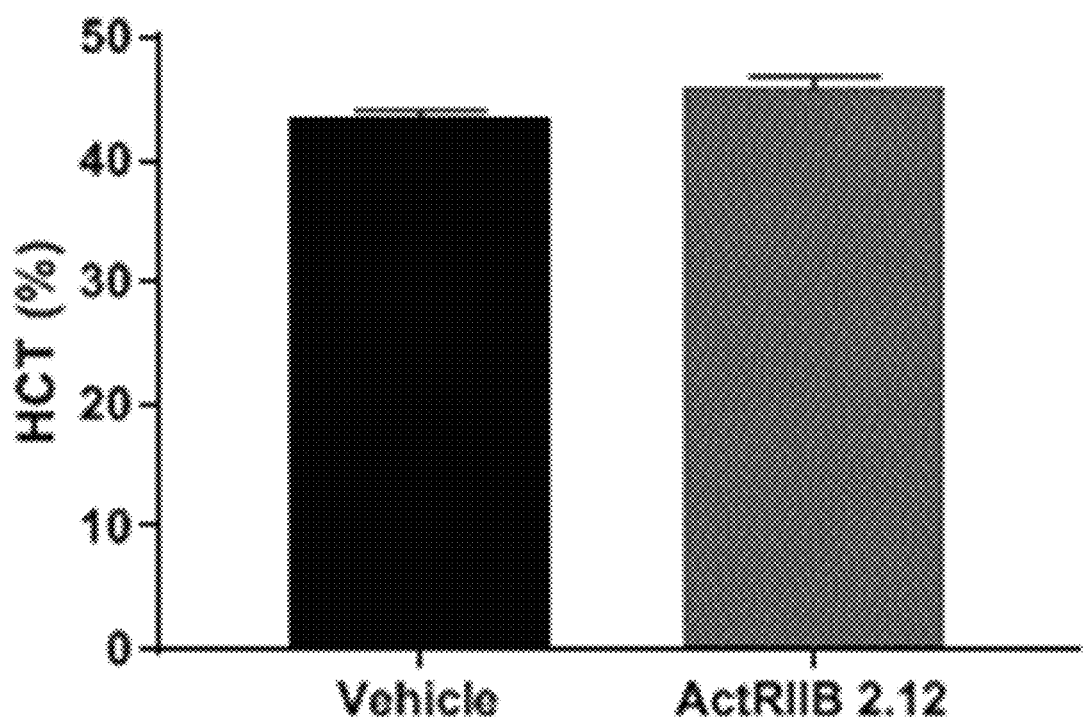

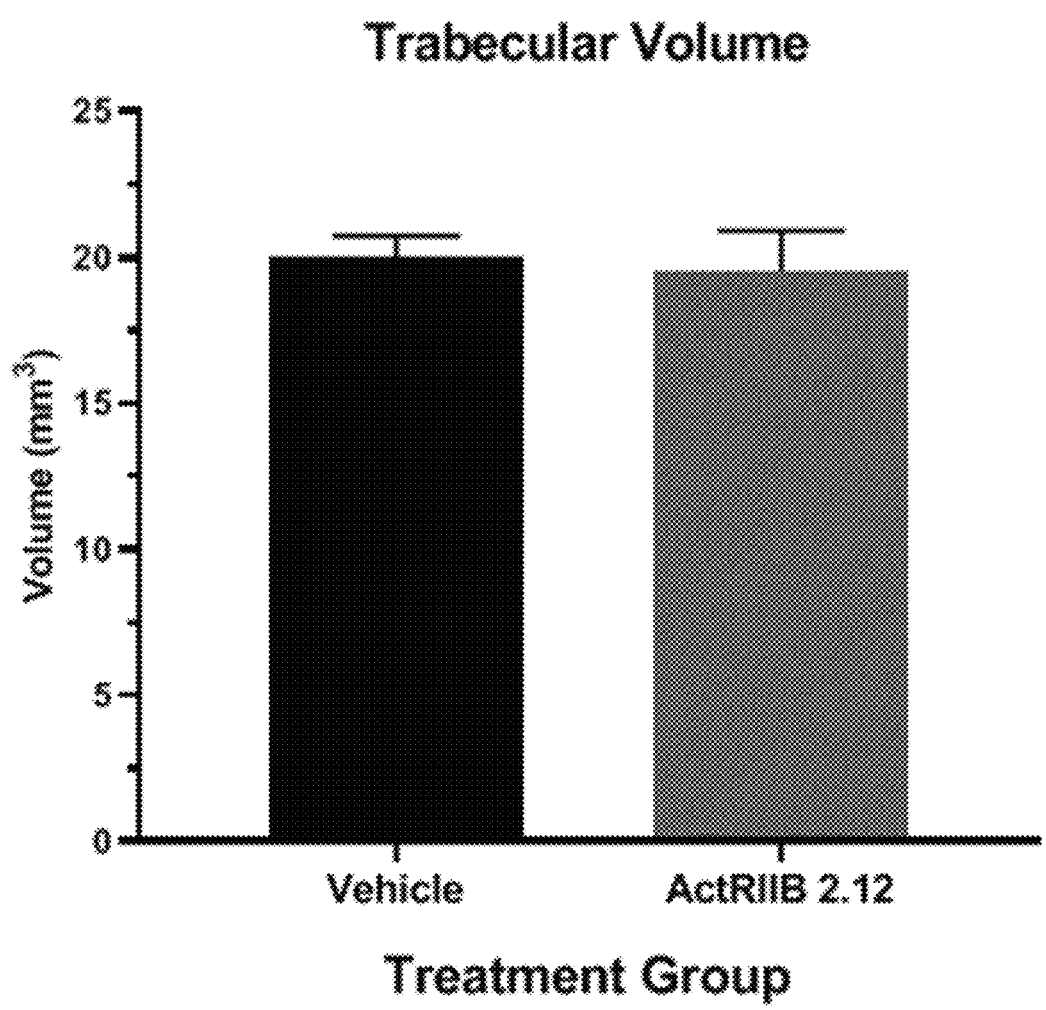

ACTIVIN RECEPTOR TYPE IIB VARIANTS AND METHODS OF USE THEREOF

SEQUENCE LISTING

The instant application contains a Sequence Listing which has been submitted electronically in XML file format and is hereby incorporated by reference in its entirety. Said XML copy, created on Dec. 27, 2023, is named 51184-007004_Sequence_Listing_12_27_23._xml and is 79,199 bytes in size.

BACKGROUND OF THE INVENTION

Duchenne muscular dystrophy (DMD), facioscapulohumeral muscular dystrophy (FSHD), inclusion body myositis (IBM), and amyotrophic lateral sclerosis (ALS) are examples of muscle diseases that involve weakness and atrophy of muscles and/or motor neurons that control voluntary muscle movements. DMD is caused by mutations in the X-linked dystrophin gene and characterized by progressive muscle degeneration and weakness in all skeletal muscles. FSHD particularly affects skeletal muscles of the face, shoulders, upper arms, and lower legs. IBM is an inflammatory muscle disease that mainly affects muscles of the thighs and muscles of the arms that control finger and wrist flexion. ALS is a motor neuron disease characterized by stiff muscles, muscle twitching, and muscle atrophy throughout the body due to the degeneration of the motor neurons. Efforts to improve treatment and survival of subjects having these devastating muscle diseases have not been successful.

Healthy bone undergoes a constant remodeling that involves both bone breakdown and bone growth. Bone growth is mediated by the osteoblast cell type whereas the osteoclasts resorb the bone. Pathology occurs when these systems fall out of balance either through downregulation of the anabolic program, upregulation of the catabolic system or a combination of both, resulting in a net bone loss. Therefore, controlling the balance in bone remodeling can be useful for promoting the healing of damage to bone as well as the treatment of disorders, such as osteoporosis, associated with loss of bone mass and bone demineralization.

Bone damage can result from a range of root causes, including age- or cancer-related bone loss, genetic conditions, or adverse side effects of drug treatment. The World Health Organization estimates that osteoporosis alone affects 75 million people in the U.S., Europe and Japan, and is a significant risk factor in bone damage. In general, the whole of bone loss represents pathological states for which there are few effective treatments. Treatment instead focuses on immobilization, exercise and dietary modifications rather than agents that directly promote bone growth and increase bone density. With respect to osteoporosis, estrogen, calcitonin, osteocalcin with vitamin K, or high doses of dietary calcium are all used as therapeutic interventions. Other therapeutic approaches to osteoporosis include bisphosphonates, parathyroid hormone, parathyroid hormone related protein (PTHrP), calci mimetics, statins, anabolic steroids, lanthanum and strontium salts, and sodium fluoride. Such therapeutics, however, are often associated with undesirable side effects.

Fibrosis is the formation of excess connective tissue in an organ or tissue. The connective tissue, which can form in response to damage (e.g., injury) or as part of an immune response (e.g., an inflammatory response), can disrupt the structure and function of the organ or tissue in which it forms, leading to an increase in tissue stiffness. Fibrosis can occur in many organs and tissues within the body, including the lung (e.g., pulmonary fibrosis, cystic fibrosis), liver (e.g., cirrhosis), heart (e.g., endomyocardial fibrosis or fibrosis after myocardial infarction), brain (e.g., glial scar formation), skin (e.g., formation of keloids), kidney (e.g., renal fibrosis), and eye (e.g., corneal fibrosis), among others; and is known to be associated with certain medical treatments (e.g., chemotherapy, radiation therapy, and surgery). There are limited treatment options for patients with fibrosis, and most treatments are focused on improving quality of life or temporarily slowing disease progression.

Anemia is a global health problem with health implications that affect both morbidity and mortality. In the United States alone, the prevalence of anemia nearly doubled from 2003 to 2012. Symptoms of anemia include fatigue, weakness, shortness of breath, heart palpitations, and reduced cognitive performance, and children, pregnant women, women of reproductive age, and the elderly have been found to have the highest risk of developing anemia. The most common form of anemia is iron deficiency anemia, but anemia can also be caused by chronic diseases, blood loss, and red blood cell destruction. While iron deficiency anemia can be treated with iron supplements, many other forms of anemia, such as aplastic anemia, anemia of chronic disease, and hemolytic anemia may require blood transfusions.

Pulmonary hypertension (PH) is a serious condition characterized by higher than normal pressure in the blood vessels between the lungs and the heart. PH can be categorized into five major types: arterial (PAH), venous (PH secondary to left-sided heart disease), hypoxic (PH caused by lung disease), thromboembolic (PH caused by chronic arterial obstruction, e.g., blood clots), or miscellaneous (PH with unclear or multifactorial mechanisms), also known as WHO groups I-V. PAH features increased pressure in blood vessels of the lungs caused by obstruction in or narrowing of small blood vessels in the lungs due to scarring. This leads to increased resistance to blood flow through the lungs and forces the right side of the heart to work harder, which may lead to heart failure, reduced blood oxygenation, and reduced life expectancy. PAH can be idiopathic (e.g., having no identifiable cause), heritable (e.g., familial, often due to a genetic mutation), or may be related to drug use (e.g., methamphetamine or cocaine use), infection (e.g., HIV infection or schistosomiasis), cirrhosis of the liver, congenital heart abnormalities, or connective tissue/autoimmune disorders (e.g., scleroderma or lupus). Treatments for PH include vasodilators, anticoagulants, and supplemental oxygen, but these treatments manage disease symptoms rather than targeting the biological mechanisms that cause the disease.

There exists a need for novel and effective treatments for muscular diseases, bone diseases, anemia, fibrosis, and PH.

SUMMARY OF THE INVENTION

The present invention features polypeptides that include an extracellular activin receptor type IIB (ActRIIB) variant. In some embodiments, a polypeptide of the invention includes an extracellular ActRIIB variant fused to the N- or C-terminus of an Fc domain monomer or another moiety. Such moieties may be attached by amino acid or other covalent bonds and may increase stability of the polypeptide. A polypeptide including an extracellular ActRIIB variant fused to an Fc domain monomer may also form a dimer (e.g., a homodimer or heterodimer) through the interaction between two Fc domain monomers. The polypeptides of the invention may be used to increase muscle mass and strength in a subject having or at risk of developing a disease or condition involving weakness and atrophy of muscles, e.g., Duchenne muscular dystrophy (DMD), facioscapulohumeral muscular dystrophy (FSHD), inclusion body myositis (IBM), amyotrophic lateral sclerosis (ALS), sarcopenia, or cancer cachexia. The polypeptides of the invention may also be used to increase bone mass or bone mineral density in a subject having or at risk of developing a disease or condition involving bone damage, e.g., primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility. Additionally, the polypeptides of the invention may be used to increase red blood cell levels (e.g., increase hemoglobin levels, increase hematocrit, and/or increase red blood cell count) in a subject in need thereof, e.g., a subject having or at risk of developing anemia or blood loss, to prevent or reduce fibrosis in a subject having or at risk of developing fibrosis, or to treat, prevent, or delay the development or progression of pulmonary hypertension in a subject having or at risk of developing pulmonary hypertension (e.g., arterial, venous, hypoxic, thromboembolic, or miscellaneous pulmonary hypertension). Further, the polypeptides of the invention may also be used to affect myostatin, activin, and/or bone morphogenetic protein 9 (BMP9) signaling in a subject having a risk of developing or having a disease or condition involving weakness and atrophy of muscles, bone damage or bone demineralization, low blood cell levels (e.g., low hemoglobin levels, low hematocrit, and/or low red blood cell counts), fibrosis, or pulmonary hypertension (e.g., arterial, venous, hypoxic, thromboembolic, or miscellaneous pulmonary hypertension).

In a first aspect, the invention features a polypeptide containing an extracellular ActRIIB variant having one or more amino acid substitutions relative to the sequence of GRGEAETRECIYYNANWELERTNQSGLERCEGEQDKRLHCYASWRNSSGTIELVKKGCWL DDFNCYDRQECVATEENPQVYFCCCEGNFCNERFTHLPEAGGPEVTYEPPPTAPT (SEQ ID NO: 17), in which the variant contains one or more amino acid substitutions that impart reduced BMP9 binding relative to wild type extracellular ActRIIB, and one or more additional amino acid substitutions, wherein the substitutions that reduce BMP9 binding are one or more of: (a) amino acid substitution E75K; (b) amino acid substitutions Q69T and E70D; or (c) amino acid substitutions Q69D and E70T.

In some embodiments, the one or more additional amino acid substitutions are selected from the group consisting of I11L, Y12F, L19K, E20D, S25T, L27V, R29P, E31Y, E33D, Q34K, L38R, Y41F, R45K, S47I, S48T, T50S, I51L, L53I, K56Q, F63I, T74K, E76D, N77S, Q79E, and F89M.

In some embodiments, the variant contains amino acid substitution E75K and additional amino acid substitutions E20D and F63I.

In some embodiments, the variant contains amino acid substitution E75K and additional amino acid substitutions that reduce BMP9 binding. In some embodiments of any of the above aspects, the additional amino acid substitutions that reduce BMP9 binding are T74K, E76D, N77S, and Q79E.

In some embodiments, the variant further contains one or more additional amino acid substitutions.

In some embodiments, the variant contains additional amino acid substitutions Y41F, R45K, and K56Q. In some embodiments, the variant further contains additional amino acid substitutions Y12F, L19K, E20D, R29P, E31Y, E33D, L38R, and F63I.

In some embodiments, the variant contains additional amino acid substitutions S25T and S47I. In some embodiments, the variant contains additional amino acid substitution S48T.

In some embodiments, the variant contains additional amino acid substitution R29P.

In some embodiments, the variant contains additional amino acid substitutions E31Y, E33D, and Q34K.

In some embodiments, the variant contains additional amino acid substitutions Y12F, L19K, and E20D.

In some embodiments, the variant contains additional amino acid substitutions E31Y, E33D, and L38R.

In some embodiments, the variant contains amino acid substitutions Q69T and E70D, and additional amino acid substitutions I11L, L27V, Q34K, T50S, I51L, L53I, and F89M.

In some embodiments, the variant contains amino acid substitutions Q69D and E70T, and additional amino acid substitutions I11L, L27V, Q34K, T50S, I51L, L53I, and F89M.

In some embodiments, the variant further contains amino acid substitution E75K.

Embodiments E1 to E59 below describe other features of the invention.

E1. A polypeptide containing an ActRIIB variant, the variant having a sequence of GRGEAETRECX$_1$X$_2$YNANWEX$_3$X$_4$RTNQX$_5$GX$_6$EX$_7$CX$_8$GX$_9$X$_{10}$DKRX$_{11}$HCX$_{12}$ASWX$_{13}$NX$_{14}$X$_{15}$GX$_{16}$X$_{17}$EX$_{18}$VKX$_{19}$GCWLDDX$_{20}$NCYDRX$_{21}$X$_{22}$CVAX$_{23}$X$_{24}$X$_{25}$X$_{26}$PX$_{27}$VYFCCCEGNX$_{28}$CNERFT HLPEAGGPEVTYEPP PTAPT (SEQ ID NO: 1), wherein $X_1$ is I or L; $X_2$ is F or Y; $X_3$ is L or K; $X_4$ is D or E; $X_5$ is T or S; X6 is L or V; $X_7$ is P or R; $X_8$ is Y or E; $X_9$ is D or E; $X_{10}$ is K or Q; $X_{10}$ is R or L; $X_{12}$ is Y or F; $X_{13}$ is R or K; $X_{14}$ iS S or I; $X_{15}$ is S or T; $X_{16}$ is S or T; $X_{17}$ is I or L; $X_{18}$ is I or L; $X_{19}$ is K or Q; $X_{20}$ is F or I; $X_{21}$ is Q, T, or D; $X_{22}$ is E, D, or T; $X_{23}$ is K or T; $X_{24}$ is K or E; $X_{25}$ is D or E; $X_{26}$ is S or N; $X_{27}$ is E or Q; and $X_{28}$ is F or M, and wherein $X_{24}$ is E and/or either $X_{21}$ is T and $X_{22}$ is D or $X_{21}$ is D and $X_{22}$ is T.

E2. The variant of E1, wherein $X_1$ is I.
E3. The variant of E1, wherein $X_1$ is L.
E4. The variant of any one of E1-E3, wherein $X_2$ is F.
E5. The variant of any one of E1-E3, wherein $X_2$ is Y.
E6. The variant of any one of E1-E5, wherein $X_3$ is L.
E7. The variant of any one of E1-E5, wherein $X_3$ is K.
E8. The variant of any one of E1-E7, wherein $X_4$ is D.
E9. The variant of any one of E1-E7, wherein $X_4$ is E.
E10. The variant of any one of E1-E9, wherein $X_5$ is T.
E11. The variant of any one of E1-E9, wherein $X_5$ is S.
E12. The variant of any one of E1-E11, wherein $X_6$ is L.
E13. The variant of any one of E1-E11, wherein $X_6$ is V.
E14. The variant of any one of E1-E13, wherein $X_7$ is P.
E15. The variant of any one of E1-E13, wherein $X_7$ is R.
E16. The variant of any one of E1-E15, wherein $X_8$ is Y.
E17. The variant of any one of E1-E15, wherein $X_8$ is E.
E18. The variant of any one of E1-E17, wherein $X_9$ is D.
E19. The variant of any one of E1-E17, wherein $X_9$ is E.
E20. The variant of any one of E1-E19, wherein $X_{10}$ is K.
E21. The variant of any one of E1-E19, wherein $X_{10}$ is Q.
E22. The variant of any one of E1-E21, wherein $X_{11}$ is R.
E23. The variant of any one of E1-E21, wherein $X_{11}$ is L.
E24. The variant of any one of E1-E23, wherein $X_{12}$ is Y.

E25. The variant of any one of E1-E23, wherein $X_{12}$ is F.
E26. The variant of any one of E1-E25, wherein $X_{13}$ is R.
E27. The variant of any one of E1-E25, wherein $X_{13}$ is K.
E28. The variant of any one of E1-E27, wherein $X_{14}$ is S.
E29. The variant of any one of E1-E27, wherein $X_{14}$ is I.
E30. The variant of any one of E1-E29, wherein $X_{15}$ is S.
E31. The variant of any one of E1-E29, wherein $X_{15}$ is T.
E32. The variant of any one of E1-E31, wherein $X_{15}$ is S.
E33. The variant of any one of E1-E31, wherein $X_{16}$ is T.
E34. The variant of any one of E1-E33, wherein $X_{17}$ is I.
E35. The variant of any one of E1-E33, wherein $X_{17}$ is L.
E36. The variant of any one of E1-E35, wherein $X_{18}$ is I.
E37. The variant of any one of E1-E35, wherein $X_{18}$ is L.
E38. The variant of any one of E1-E37, wherein $X_{19}$ is K.
E39. The variant of any one of E1-E37, wherein $X_{19}$ is Q.
E40. The variant of any one of E1-E39, wherein $X_{20}$ is F.
E41. The variant of any one of E1-E39, wherein $X_{20}$ is I.
E42. The variant of any one of E1-E41, wherein $X_{21}$ is Q.
E43. The variant of any one of E1-E41, wherein $X_{21}$ is T.
E44. The variant of any one of E1-E41, wherein $X_{21}$ is D.
E45. The variant of any one of E1-E42, wherein $X_{22}$ is E.
E46. The variant of any one of E1-E41 and E43, wherein $X_{22}$ is D.
E47. The variant of any one of E1-E41 and E44, wherein $X_{22}$ is T.
E48. The variant of any one of E1-E47, wherein $X_{23}$ is K.
E49. The variant of any one of E1-E47, wherein $X_{23}$ is T.
E50. The variant of any one of E1-E49, wherein $X_{24}$ is K.
E51. The variant of any one of E1-E41, E43, E44, E46, and E47-E49, wherein $X_{24}$ is E.
E52. The variant of any one of E1-E51, wherein $X_{25}$ is D.
E53. The variant of any one of E1-E51, wherein $X_{25}$ is E.
E54. The variant of any one of E1-E53, wherein $X_{26}$ is S.
E55. The variant of any one of E1-E53, wherein $X_{26}$ is N.
E56. The variant of any one of E1-E55, wherein $X_{27}$ is E.
E57. The variant of any one of E1-E55, wherein $X_{27}$ is Q.
E58. The variant of any one of E1-E57, wherein $X_{28}$ is F.
E59. The variant of any one of E1-E57, wherein $X_{28}$ is M.

In some embodiments, the variant has the sequence of any one of SEQ ID NOs: 2-15.

In some embodiments, the polypeptide further includes an Fc domain monomer fused to the C-terminus of the polypeptide (e.g., the C-terminus of the variant) by way of a linker. In some embodiments, the Fc domain monomer has the sequence of SEQ ID NO: 19. In some embodiments, the polypeptide forms a dimer.

In some embodiments, the polypeptide further includes a wild-type Fc domain fused to the C-terminus of the polypeptide (e.g., the C-terminus of the variant) by way of a linker. In some embodiments, the wild-type Fc domain has the sequence of SEQ ID NO: 71.

In some embodiments, the polypeptide further includes an Fc domain with amino acid substitutions fused to the C-terminus of the polypeptide (e.g., the C-terminus of the variant) by way of a linker. In some embodiments, the Fc domain does not form a dimer.

In some embodiments, the polypeptide further includes an albumin-binding peptide fused to the C-terminus of the polypeptide (e.g., the C-terminus of the variant) by way of a linker. In some embodiments, the albumin-binding peptide has the sequence of SEQ ID NO: 72.

In some embodiments, the polypeptide further includes a fibronectin domain fused to the C-terminus of the polypeptide (e.g., the C-terminus of the variant) by way of a linker. In some embodiments, the fibronectin domain has the sequence of SEQ ID NO: 73.

In some embodiments, the polypeptide further includes a human serum albumin fused to the C-terminus of the polypeptide (e.g., the C-terminus of the variant) by way of a linker. In some embodiments, the human serum albumin has the sequence of SEQ ID NO: 74.

In some embodiments, the linker is an amino acid spacer. In some embodiments of any of the above aspects, the amino acid spacer is GGG, GGGA (SEQ ID NO: 20), GGGG (SEQ ID NO: 22), GGGAG (SEQ ID NO: 52), GGGAGG (SEQ ID NO: 53), or GGGAGGG (SEQ ID NO: 54).

In some embodiments, the amino acid spacer is GA, GS, GG, GGA, GGS, GGG, GGGS (SEQ ID NO: 21), GGGGA (SEQ ID NO: 23), GGGGS (SEQ ID NO: 24), GGGGG (SEQ ID NO: 25), GGAG (SEQ ID NO: 26), GGSG (SEQ ID NO: 27), AGGG (SEQ ID NO: 28), SGGG (SEQ ID NO: 29), GAGA (SEQ ID NO: 30), GSGS (SEQ ID NO: 31), GAGAGA (SEQ ID NO: 32), GSGSGS (SEQ ID NO: 33), GAGAGAGA (SEQ ID NO: 34), GSGSGSGS (SEQ ID NO: 35), GAGAGAGAGA (SEQ ID NO: 36), GSGSGSGSGS (SEQ ID NO: 37), GAGAGAGAGAGA (SEQ ID NO: 38), GSGSGSGSGSGS (SEQ ID NO: 39), GGAGGA (SEQ ID NO: 40), GGSGGS (SEQ ID NO: 41), GGAGGAGGA (SEQ ID NO: 42), GGSGGSGGS (SEQ ID NO: 43), GGAGGAGGAGGA (SEQ ID NO: 44), and GGSGGSGGSGGS (SEQ ID NO: 45), GGAGGGAG (SEQ ID NO: 46), GGSGGGSG (SEQ ID NO: 47), GGAGGGAGGGAG (SEQ ID NO: 48), and GGSGGGSGGGSG (SEQ ID NO: 49), GGGGAGGGGAGGGGA (SEQ ID NO: 50), GGGGSGGGGSGGGGS (SEQ ID NO: 51), AAAL (SEQ ID NO: 55), AAAK (SEQ ID NO: 56), AAAR (SEQ ID NO: 57), EGKSSGSGSESKST (SEQ ID NO: 58), GSAGSAAGSGEF (SEQ ID NO: 59), AEAAAKEAAAKA (SEQ ID NO: 60), KESGSVSSEQLAQFRSLD (SEQ ID NO: 61), GENLYFQSGG (SEQ ID NO: 62), SACYCELS (SEQ ID NO: 63), RSIAT (SEQ ID NO: 64), RPACKIPNDLKQKVMNH (SEQ ID NO: 65), GGSAGGSGSGSSGGSSGASGTGTAGGTGSGSGTGSG (SEQ ID NO: 66), AAANSSIDLISVPVDSR (SEQ ID NO: 67), GGSGGGSEGGGSEGGGSEGGGSEGGGSEGGGSGGGS (SEQ ID NO: 68), EAAAK (SEQ ID NO: 69), or PAPAP(SEQ ID NO: 70).

In some embodiments, the polypeptide has a serum half-life of at least seven days.

In some embodiments, the polypeptide has increased or decreased binding to one or more an ActRIIB ligands (e.g., activin, myostatin, GDF-11, or BMP9) compared to wild-type ActRIIB.

In some embodiments, the polypeptide binds to human bone morphogenetic protein 9 (BMP9) with a $K_D$ of 200 µM or higher.

In some embodiments, the polypeptide binds to activin and/or myostatin and has reduced or weak binding to human BMP9.

In some embodiments, the polypeptide does not substantially bind to human BMP9.

In some embodiments, the polypeptide binds to human activin A with a $K_D$ of 800 µM or less.

In some embodiments, the polypeptide binds to human activin B with a $K_D$ of 800 µM or less.

In some embodiments, the polypeptide binds to human GDF-11 with a $K_D$ of 5 µM or higher.

In another aspect, the invention features a nucleic acid molecule encoding a polypeptide described herein (e.g., a polypeptide including an extracellular ActRIIB variant having a sequence of any one of SEQ ID NOs: 1-15 (e.g., SEQ ID NOs: 2-15)).

In another aspect, the invention features a vector including a nucleic acid molecule described herein.

In another aspect, the invention features a host cell that expresses a polypeptide described herein, wherein the host cell includes a nucleic acid molecule or vector described in the previous two aspects, wherein the nucleic acid molecule or vector is expressed in the host cell.

In another aspect, the invention features a method of preparing a polypeptide described herein, wherein the method includes: a) providing a host cell comprising a nucleic acid molecule or a vector described herein, and b) expressing the nucleic acid molecule or vector in the host cell under conditions that allow for the formation of the polypeptide.

In another aspect, the invention features a pharmaceutical composition including a polypeptide, nucleic acid molecule, or vector described herein and one or more pharmaceutically acceptable carriers or excipients. In some embodiments of the pharmaceutical composition, the polypeptide, nucleic acid molecule, or vector is in a therapeutically effective amount.

In another aspect, the invention features a construct including two identical polypeptides (e.g., a homodimer), each including an extracellular ActRIIB variant described herein (e.g., an ActRIIB variant having a sequence of any one of SEQ ID NOs: 1-15 (e.g., SEQ ID NOs: 2-15)) fused to the N- or C-terminus of an Fc domain monomer (e.g., the sequence of SEQ ID NO: 19). The two Fc domain monomers in the two polypeptides interact to form an Fc domain in the construct.

In another aspect, the invention features a construct including two different polypeptides (e.g., a heterodimer) each including an extracellular ActRIIB variant described herein (e.g., an ActRIIB variant having a sequence of any one of SEQ ID NOs: 1-15 (e.g., SEQ ID NOs: 2-15)) fused to the N- or C-terminus of an Fc domain monomer (e.g., the sequence of SEQ ID NO: 19). The two Fc domain monomers in the two polypeptides interact to form an Fc domain in the construct.

In another aspect, the invention features a method of increasing lean mass in a subject in need thereof. The method includes administering to the subject a therapeutically effective amount of a polypeptide, nucleic acid molecule, or vector described herein or a pharmaceutical composition described herein.

In another aspect, the invention features a method of increasing muscle mass in a subject in need thereof. The method includes administering to the subject a therapeutically effective amount of a polypeptide, nucleic acid molecule, or vector described herein or a pharmaceutical composition described herein.

In some embodiments of the method of increasing lean mass or muscle mass in a subject, the subject has or is at risk of developing Duchenne muscular dystrophy (DMD), facioscapulohumeral muscular dystrophy (FSHD), inclusion body myositis (IBM), amyotrophic lateral sclerosis (ALS), sarcopenia, or cancer cachexia.

In another aspect, the invention features a method of treating a subject having or at risk of developing muscle disease. The method includes administering to the subject a therapeutically effective amount of a polypeptide, nucleic acid molecule, or vector described herein or a pharmaceutical composition described herein. In some embodiments, the muscle disease is DMD, FSHD, IBM, ALS, sarcopenia, or cancer cachexia In another aspect, the invention features a method of affecting myostatin, activin, and/or BMP9 signaling (e.g., reducing or inhibiting the binding of myostatin, activin, and/or BMP9 to their endogenous receptors) in a subject having or at risk of developing a disease or condition involving weakness and atrophy of muscles, wherein method includes administering to the subject a therapeutically effective amount of a polypeptide, nucleic acid molecule, or vector described herein or a pharmaceutical composition described herein. In some embodiments of this aspect, the disease or condition is DMD, FSHD, IBM, ALS, sarcopenia, or cancer cachexia.

In another aspect, the invention features a method of treating a subject having or at risk of developing DMD by administering to the subject a therapeutically effective amount of a polypeptide, nucleic acid molecule, or vector described herein or a pharmaceutical composition described herein.

In another aspect, the invention features a method of treating a subject having or at risk of developing FSHD by administering to the subject a therapeutically effective amount of a polypeptide, nucleic acid molecule, or vector described herein or a pharmaceutical composition described herein.

In another aspect, the invention features a method of treating a subject having or at risk of developing IBM by administering to the subject a therapeutically effective amount of a polypeptide, nucleic acid molecule, or vector described herein or a pharmaceutical composition described herein.

In another aspect, the invention features a method of treating a subject having or at risk of developing ALS by administering to the subject a therapeutically effective amount of a polypeptide, nucleic acid molecule, or vector described herein or a pharmaceutical composition described herein.

In another aspect, the invention features a method of treating a subject having or at risk of developing sarcopenia by administering to the subject a therapeutically effective amount of a polypeptide, nucleic acid molecule, or vector described herein or a pharmaceutical composition described herein.

In another aspect, the invention features a method of treating a subject having or at risk of developing cancer cachexia by administering to the subject a therapeutically effective amount of a polypeptide, nucleic acid molecule, or vector described herein or a pharmaceutical composition described herein.

In another aspect, the invention features a method of increasing bone mineral density in a subject in need thereof. The method includes administering to the subject a therapeutically effective amount of a polypeptide, nucleic acid molecule, or vector described herein or a pharmaceutical composition described herein.

In another aspect, the invention features a method of reducing bone resorption in a subject in need thereof. The method includes administering to the subject a therapeutically effective amount of a polypeptide, nucleic acid molecule, or vector described herein or a pharmaceutical composition described herein.

In another aspect, the invention features a method of increasing bone formation in a subject in need thereof. The method includes administering to the subject a therapeutically effective amount of a polypeptide, nucleic acid molecule, or vector described herein or a pharmaceutical composition described herein.

In another aspect, the invention features a method of increasing bone strength in a subject in need thereof. The method includes administering to the subject a therapeutically effective amount of a polypeptide, nucleic acid molecule, or vector described herein or a pharmaceutical composition described herein.

In another aspect, the invention features a method of reducing the risk of bone fracture in a subject in need thereof. The method includes administering to the subject a therapeutically effective amount of a polypeptide, nucleic acid molecule, or vector described herein or a pharmaceutical composition described herein.

In some embodiments of any of the above aspects, the subject has or is at risk of developing primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss. In some embodiments, the subject has or is at risk of developing osteoporosis.

In another aspect, the invention features a method of treating a subject having or at risk of developing bone disease. The method includes administering to the subject a therapeutically effective amount of a polypeptide, nucleic acid molecule, or vector described herein or a pharmaceutical composition described herein. In some embodiments, the bone disease is primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss. In some embodiments, the bone disease is osteoporosis.

In another aspect, the invention features a method of affecting myostatin, activin, and/or BMP9 signaling (e.g., reducing or inhibiting the binding of myostatin, activin, and/or BMP9 to their endogenous receptors) in a subject having or at risk of developing a disease or condition involving bone damage, wherein method includes administering to the subject a therapeutically effective amount of a polypeptide, nucleic acid molecule, or vector described herein or a pharmaceutical composition described herein. In some embodiments of this aspect, the disease or condition is primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss. In some embodiments, the disease or condition is osteoporosis.

In another aspect, the invention features a method of treating a subject having or at risk of developing primary osteoporosis by administering to the subject a therapeutically effective amount of a polypeptide, nucleic acid molecule, or vector described herein or a pharmaceutical composition described herein.

In another aspect, the invention features a method of treating a subject having or at risk of developing secondary osteoporosis by administering to the subject a therapeutically effective amount of a polypeptide, nucleic acid molecule, or vector described herein or a pharmaceutical composition described herein.

In another aspect, the invention features a method of treating a subject having or at risk of developing osteopenia by administering to the subject a therapeutically effective amount of a polypeptide, nucleic acid molecule, or vector described herein or a pharmaceutical composition described herein.

In another aspect, the invention features a method of treating a subject having or at risk of developing a fracture by administering to the subject a therapeutically effective amount of a polypeptide, nucleic acid molecule, or vector described herein or a pharmaceutical composition described herein.

In another aspect, the invention features a method of treating a subject having or at risk of developing bone cancer or cancer metastasis-related bone loss by administering to the subject a therapeutically effective amount of a polypeptide, nucleic acid molecule, or vector described herein or a pharmaceutical composition described herein.

In another aspect, the invention features a method of treating a subject having or at risk of developing Paget's disease by administering to the subject a therapeutically effective amount of a polypeptide, nucleic acid molecule, or vector described herein or a pharmaceutical composition described herein.

In another aspect, the invention features a method of treating a subject having or at risk of developing renal osteodystrophy by administering to the subject a therapeutically effective amount of a polypeptide, nucleic acid molecule, or vector described herein or a pharmaceutical composition described herein.

In another aspect, the invention features a method of treating a subject having or at risk of developing treatment-related bone loss by administering to the subject a therapeutically effective amount of a polypeptide, nucleic acid molecule, or vector described herein or a pharmaceutical composition described herein.

In another aspect, the invention features a method of treating a subject having or at risk of developing diet-related bone loss by administering to the subject a therapeutically effective amount of a polypeptide, nucleic acid molecule, or vector described herein or a pharmaceutical composition described herein.

In another aspect, the invention features a method of treating a subject having or at risk of developing low gravity-related bone loss by administering to the subject a therapeutically effective amount of a polypeptide, nucleic acid molecule, or vector described herein or a pharmaceutical composition described herein.

In another aspect, the invention features a method of treating a subject having or at risk of developing immobility-related bone loss by administering to the subject a therapeutically effective amount of a polypeptide, nucleic acid molecule, or vector described herein or a pharmaceutical composition described herein.

In some embodiments of any of the above aspects, the primary osteoporosis is age-related osteoporosis or hormone-related osteoporosis.

In some embodiments of any of the above aspects, the secondary osteoporosis is immobilization-induced osteoporosis or glucocorticoid-induced osteoporosis.

In some embodiments of any of the above aspects, the cancer is multiple myeloma. In some embodiments of any of the above aspects, the treatment is FGF-21 treatment, GLP-1 treatment, cancer therapy, or treatment for obesity or Type-2 diabetes.

In some embodiments of any of the above aspects, the diet-related bone loss is rickets.

In some embodiments of any of the above aspects, the subject is at risk of bone fracture.

In some embodiments of any of the above aspects, the method increases bone formation in the subject. In some embodiments of any of the above aspects, the method decreases bone resorption in the subject. In some embodiments of any of the above aspects, the method decreases bone loss in the subject. In some embodiments of any of the above aspects, the method increases osteoblast activity or osteoblastogenesis. In some embodiments of any of the above aspects, the method decreases osteoclast activity or decreases osteoclastogenesis. In some embodiments of any of the above aspects, the method decreases the risk of bone fracture. In some embodiments of any of the above aspects, the method increases bone strength.

In some embodiments of any of the above aspects, the bone is cortical bone. In some embodiments of any of the above aspects, the bone is trabecular bone.

In another aspect, the invention features method of decreasing or preventing fibrosis in a subject in need thereof by administering to the subject a therapeutically effective amount of a polypeptide, nucleic acid molecule, or vector described herein or a pharmaceutical composition described herein.

In another aspect, the invention features method of slowing or inhibiting the progression of fibrosis in a subject in need thereof by administering to the subject a therapeutically effective amount of a polypeptide, nucleic acid molecule, or vector described herein or a pharmaceutical composition described herein.

In another aspect, the invention features method of reducing the risk of developing fibrosis in a subject in need thereof by administering to the subject a therapeutically effective amount of a polypeptide, nucleic acid molecule, or vector described herein or a pharmaceutical composition described herein.

In another aspect, the invention features method of treating a subject having or at risk of developing fibrosis by administering to the subject a therapeutically effective amount of a polypeptide, nucleic acid molecule, or vector described herein or a pharmaceutical composition described herein.

In some embodiments of any of the above aspects, the fibrosis is chemotherapeutic drug-induced fibrosis, radiation-induced fibrosis, pulmonary fibrosis, hepatic fibrosis, renal fibrosis (e.g., fibrosis related to chronic kidney disease), corneal fibrosis, heart fibrosis, bone marrow fibrosis, mediastinal fibrosis, retropertinoneal fibrosis, arthrofibrosis, osteoarticular fibrosis, tissue fibrosis, a tumor stroma, a desmoplastic tumor, a surgical adhesion, a hypertrophic scar, or a keloid.

In some embodiments of the above aspects, the fibrosis is fibrosis associated with wounds, burns, hepatitis B or C infection, fatty liver disease, Schistosoma infection, kidney disease (e.g., chronic kidney disease), heart disease, macular degeneration, Crohn's disease, retinal or vitreal retinopathy, systemic or local scleroderma, atherosclerosis, or restenosis. In some embodiments of any of the above aspects, the fibrosis results from chronic kidney disease.

In another aspect, the invention features a method of affecting myostatin, activin, and/or BMP9 signaling (e.g., reducing or inhibiting the binding of myostatin, activin, and/or BMP9 to their endogenous receptors) in a subject having or at risk of developing fibrosis or a disease or condition involving fibrosis, wherein method includes administering to the subject a therapeutically effective amount of a polypeptide, nucleic acid molecule, or vector described herein or a pharmaceutical composition described herein. In some embodiments of this aspect, the disease or condition is chemotherapeutic drug-induced fibrosis, radiation-induced fibrosis, pulmonary fibrosis, hepatic fibrosis, renal fibrosis (e.g., fibrosis related to chronic kidney disease), corneal fibrosis, heart fibrosis, bone marrow fibrosis, mediastinal fibrosis, retropertinoneal fibrosis, arthrofibrosis, osteoarticular fibrosis, tissue fibrosis, a tumor stroma, a desmoplastic tumor, a surgical adhesion, a hypertrophic scar, or a keloid. In some embodiments of this aspect, the disease or condition is fibrosis associated with wounds, burns, hepatitis B or C infection, fatty liver disease, Schistosoma infection, kidney disease (e.g., chronic kidney disease), heart disease, macular degeneration, Crohn's disease, retinal or vitreal retinopathy, systemic or local scleroderma, atherosclerosis, or restenosis. In some embodiments of this aspect, the fibrosis results from chronic kidney disease.

In some embodiments of any of the above aspects, the tissue fibrosis is fibrosis affecting a tissue selected from the group consisting of muscle tissue, skin epidermis, skin dermis, tendon, cartilage, pancreatic tissue, uterine tissue, neural tissue, testis, ovary, adrenal gland, artery, vein, colon, small intestine, large intestine, biliary tract, and gut.

In some embodiments of any of the above aspects, the method improves the function of a fibrotic tissue or organ. In some embodiments of any of the above aspects, the method slows or inhibits the progression of fibrosis. In some embodiments of any of the above aspects, the method reduces (e.g., reduces the frequency or severity of) one or more symptom of fibrosis.

In another aspect, the invention features a method of increasing red blood cell levels (e.g., increasing hemoglobin levels, red blood cell count, or hematocrit) in a subject in need thereof by administering to the subject a therapeutically effective amount of a polypeptide, nucleic acid molecule, or vector described herein or a pharmaceutical composition described herein.

In another aspect, the invention features a method of promoting or increasing red blood cell formation in a subject in need thereof by administering to the subject a therapeutically effective amount of a polypeptide, nucleic acid molecule, or vector described herein or a pharmaceutical composition described herein.

In some embodiments of any of the above aspects, the subject has or is at risk of developing anemia or blood loss.

In another aspect, the invention features a method of affecting myostatin, activin, and/or BMP9 signaling (e.g., reducing or inhibiting the binding of myostatin, activin, and/or BMP9 to their endogenous receptors) in a subject having or at risk of developing a disease or condition involving low red blood cell levels (e.g., low hemoglobin levels, low red blood cell count, or low hematocrit), wherein method includes administering to the subject a therapeutically effective amount of a polypeptide, nucleic acid molecule, or vector described herein or a pharmaceutical composition described herein.

In some embodiments of the above aspect, the disease or condition is anemia or blood loss.

In some embodiments of any of the above aspects, the anemia or blood loss is associated with cancer, cancer treatment, renal disease or failure (e.g., chronic kidney disease or acute renal disease or failure), myelodysplastic syndrome, thalassemia, nutritional deficits, adverse reaction to medication, an inflammatory or autoimmune disease, splenomegaly, porphyria, vasculitis, hemolysis, bone marrow defects, bone marrow transplantation, diabetes, liver disease (e.g., acute liver disease or chronic liver disease), bleeding (e.g., acute or chronic bleeding), infection, hemoglobinopathy, drug use, alcohol abuse, advanced age, Churg-Strauss syndrome, Felty syndrome, graft versus host disease, hematopoietic stem cell transplantation, osteomyelofibrosis, pancytopenia, pure red-cell aplasia, purpura Schoenlein-Henoch, Shwachman syndrome (e.g., Shwachman-Diamond syndrome), contraindication to transfusion, surgery, trauma, a wound, an ulcer, urinary tract bleeding, digestive tract bleeding, frequent blood donation, or heavy menstrual bleeding.

In another aspect, the invention features a method of treating a subject having or at risk of developing anemia by administering to the subject a therapeutically effective amount of a polypeptide, nucleic acid molecule, or vector described herein or a pharmaceutical composition described herein. In some embodiments, the anemia is associated with cancer, cancer treatment, renal disease or failure (e.g., chronic kidney disease or acute renal disease or failure), myelodysplastic syndrome, thalassemia, nutritional deficits, adverse reaction to medication, an inflammatory or autoimmune disease, splenomegaly, porphyria, vasculitis, hemolysis, bone marrow defects, bone marrow transplantation, diabetes, liver disease(e.g., acute liver disease or chronic liver disease), bleeding (e.g., acute or chronic bleeding), infection, hemoglobinopathy, drug use, alcohol abuse, advanced age, Churg-Strauss syndrome, Felty syndrome, graft versus host disease, hematopoietic stem cell transplantation, osteomyelofibrosis, pancytopenia, pure red-cell aplasia, purpura Schoenlein-Henoch, Shwachman syndrome (e.g., Shwachman-Diamond syndrome), contraindication to transfusion, surgery, trauma, a wound, an ulcer, urinary tract bleeding, digestive tract bleeding, frequent blood donation, or heavy menstrual bleeding.

In some embodiments of any of the above aspects, the anemia results from chronic kidney disease.

In some embodiments of any of the above aspects, the anemia is aplastic anemia, iron deficiency anemia, vitamin deficiency anemia, anemia of chronic disease, anemia associated with bone marrow disease, hemolytic anemia, sickle cell anemia, microcytic anemia, hypochromic anemia, sideroblastic anemia, Diamond Blackfan anemia, Fanconi's anemia, or refractory anemia with excess of blasts.

In some embodiments of any of the above aspects, the subject does not respond well to treatment with erythropoietin (EPO) or is susceptible to the adverse effects of EPO.

In some embodiments of any of the above aspects, the method increases red blood cell formation, red blood cell count, hemoglobin levels, or hematocrit.

In some embodiments of any of the above aspects, the method reduces the subject's need for a blood transfusion.

In another aspect, the invention features a method of preventing pulmonary hypertension (PH) in a subject in need thereof by administering to the subject a therapeutically effective amount of a polypeptide, nucleic acid molecule, or vector described herein or a pharmaceutical composition described herein.

In another aspect, the invention features a method of reducing the risk of developing PH in a subject in need thereof by administering to the subject a therapeutically effective amount of a polypeptide, nucleic acid molecule, or vector described herein or a pharmaceutical composition described herein.

In another aspect, the invention features a method of slowing or inhibiting the progression of PH in a subject in need thereof by administering to the subject a therapeutically effective amount of a polypeptide, nucleic acid molecule, or vector described herein or a pharmaceutical composition described herein.

In another aspect, the invention features a method of treating a subject having or at risk of developing PH by administering to the subject a therapeutically effective amount of a polypeptide, nucleic acid molecule, or vector described herein or a pharmaceutical composition described herein.

In another aspect, the invention features a method of affecting myostatin, activin, and/or BMP9 signaling (e.g., reducing or inhibiting the binding of myostatin, activin, and/or BMP9 to their endogenous receptors) in a subject having or at risk of developing PH by administering to the subject a therapeutically effective amount of a polypeptide, nucleic acid molecule, or vector described herein or a pharmaceutical composition described herein.

In another aspect, the invention features a method of reducing vascular remodeling in a subject having or at risk of developing PH by administering to the subject a therapeutically effective amount of a polypeptide, nucleic acid molecule, or vector described herein or a pharmaceutical composition described herein.

In another aspect, the invention features a method of reducing right ventricular hypertrophy in a subject having or at risk of developing PH by administering to the subject a therapeutically effective amount of a polypeptide, nucleic acid molecule, or vector described herein or a pharmaceutical composition described herein.

In another aspect, the invention features a method of reducing pulmonary vascular resistance in a subject having or at risk of developing PH by administering to the subject a therapeutically effective amount of a polypeptide, nucleic acid molecule, or vector described herein or a pharmaceutical composition described herein.

In some embodiments of any of the above aspects, the PH is pulmonary arterial hypertension (PAH). In some embodiments, the PAH is idiopathic PAH. In some embodiments, the PAH is heritable PAH. In some embodiments, the PAH is associated with HIV infection, schistosomiasis, cirrhosis of the liver, a congenital heart abnormality, portal hypertension, pulmonary veno-occlusive disease, pulmonary capillary hemangiomatosis, a connective tissue disorder, an autoimmune disorder (e.g., scleroderma or lupus), or drug use or abuse (e.g., use of cocaine or methamphetamine).

In some embodiments of any of the above aspects, the PH is venous PH. In some embodiments, the venous PH is associated with left ventricular systolic dysfunction, left ventricular diastolic dysfunction, valvular heart disease, congenital cardiomyopathy, or congenital or acquired pulmonary venous stenosis.

In some embodiments of any of the above aspects, the PH is hypoxic PH. In some embodiments, the hypoxic PH is associated with chronic obstructive pulmonary disease (e.g., emphysema), interstitial lung disease, sleep-disordered breathing (e.g., sleep apnea), a lung disease (e.g., pulmonary fibrosis), an alveolar hypoventilation disorder, chronic exposure to high altitude, or a developmental abnormality.

In some embodiments of any of the above aspects, the PH is thromboembolic PH. In some embodiments, the thromboembolic PH is associated with chronic thromboembolic pulmonary hypertension, pulmonary emboli, angiosarcoma, arteritis, congenital pulmonary artery stenosis, or parasitic infection.

In some embodiments of any of the above aspects, the PH is miscellaneous PH. In some embodiments, the miscellaneous PH is associated with a hematologic disease (e.g., chronic hemolytic anemia, sickle cell disease), a systemic disease (e.g., sarcoidosis, pulmonary Langerhans cell histiocytosis, lymphangioleiomyomatosis, neurofibromatosis, or vasculitis), a metabolic disorder (e.g., glycogen storage disease, Gaucher disease, or thyroid diseases), pulmonary tumoral thrombotic microangiopathy, fibrosing mediastinitis, chronic kidney failure, or segmental pulmonary hypertension.

In some embodiments of any of the above aspects, the method reduces the frequency or severity of one or more symptoms of PH (e.g., reduces the severity or frequency of one or more of shortness of breath (dyspnea), fatigue, swelling (e.g., edema) of the legs, feet, belly (ascites), or neck, chest pain or pressure, racing pulse or heart palpitations, bluish color to lips or skin (cyanosis), dizziness, or fainting).

In some embodiments of any of the above aspects, the method reduces pulmonary vascular remodeling.

In some embodiments of any of the above aspects, the method reduces vascular remodeling in the heart.

In some embodiments of any of the above aspects, the method reduces right ventricular hypertrophy.

In some embodiments of any of the above aspects, the method reduces pulmonary vascular resistance (e.g., reduces pulmonary vascular resistance compared to measurements taken prior to treatment).

In some embodiments of any of the above aspects, the method improves performance in the 6 minute walk test (e.g., improves performance compared to measurements taken prior to treatment).

In some embodiments of any of the above aspects, the method reduces or inhibits the binding of activin and/or myostatin to their receptors.

In some embodiments of any of the above aspects, the polypeptide, nucleic acid, vector, or pharmaceutical composition is administered in an amount sufficient to increase muscle mass and/or strength, increase bone mineral density, reduce bone resorption, reduce bone loss, reduce the rate of bone resorption, increase bone formation, increase the rate of bone formation, reduce osteoclast activity, increase osteoblast activity, reduce the risk of bone fracture, increase bone strength, reduce fibrosis, prevent the development of fibrosis, delay the development of fibrosis, slow or inhibit the progression of fibrosis, reduce the risk of developing fibrosis, reduce one or more symptom of fibrosis, improve the function of a fibrotic tissue or organ. increase red blood cell levels, increase hemoglobin levels, increase hematocrit, reduce the need for a transfusion, increase red blood cell formation, increase red blood cell count, treat anemia, increase prevent PH, reduce the risk of developing PH, reduce the severity or frequency of one or more symptoms of PH, delay the development of PH, slow or inhibit the progression of PH, treat PH, reduce pulmonary vascular remodeling, reduce vascular remodeling in the heart, reduce right ventricular hypertrophy, reduce pulmonary vascular resistance, improve performance in the 6 minute walk test, affect myostatin, activin, and/or BMP9 signaling in the subject, or reduce or inhibit the binding of activin and/or myostatin to their receptors. In some embodiments, the PH is PAH. In some embodiments, the PH is venous PH. In some embodiments, the PH is hypoxic PH. In some embodiments, the PH is thromboembolic PH. In some embodiments, the PH is miscellaneous PH.

In some embodiments of any of the above aspects, the method does not cause a vascular complication in the subject. In some embodiments, the method does not increase vascular permeability or leakage.

Definitions

As used herein, the term "extracellular activin receptor type IIB (ActRIIB) variant" refers to a peptide including a soluble, extracellular portion of the single transmembrane receptor, ActRIIB, that has at least one amino acid substitution relative to a wild-type extracellular ActRIIB (e.g., bold portion of the sequence of SEQ ID NO: 18 shown below). The sequence of the wild-type, human ActRIIB is shown below (SEQ ID NO: 18), in which the signal peptide is italicized and the extracellular portion is bold.

Wild-type human ActRIIB (SEQ ID NO: 18):
*MTAPWVALALLWGSLCAGS*GRGEAETRECIYYNANWELERTNQSGLERC

EGEQDKRLHCYASWRNSSGTIELVKKGCWLDDFNCYDRQECVATEENPQ

VYFCCCEGNFCNERFTHLPEAGGPEVTYEPPPTAPTLLTVLAYSLLPIG

GLSLIVLLAFWMYRHRKPPYGHVDIHEDPGPPPPSPLVGLKPLQLLEIK

ARGRFGCVWKAQLMNDFVAVKIFPLQDKQSWQSEREIFSTPGMKHENLL

QFIAAEKRGSNLEVELWLITAFHDKGSLTDYLKGNIITWNELCHVAETM

SRGLSYLHEDVPWCRGEGHKPSIAHRDFKSKNVLLKSDLTAVLADFGLA

VRFEPGKPPGDTHGQVGTRRYMAPEVLEGAINFQRDAFLRIDMYAMGLV

LWELVSRCKAADGPVDEYMLPFEEEIGQHPSLEELQEVVVHKKMRPTIK

DHWLKHPGLAQLCVTIEECWDHDAEARLSAGCVEERVSLIRRSVNGTTS

DCLVSLVTSVTNVDLPPKESSI

An extracellular ActRIIB variant may have a sequence of any one of SEQ ID NOs: 1-15. In particular embodiments, an extracellular ActRIIB variant has a sequence of any one of SEQ ID NOs: 2-15 (Table 2). In some embodiments, an extracellular ActRIIB variant may have at least 85% (e.g., at least 85%, 87%, 90%, 92%, 95%, 96%, 97%, 98%, 99%, or greater) amino acid sequence identity to the sequence of a wild-type extracellular ActRIIB (SEQ ID NO: 17).

As used herein, the term "linker" refers to a linkage between two elements, e.g., peptides or protein domains. A polypeptide described herein may include an extracellular ActRIIB variant (e.g., an extracellular ActRIIB variant having the sequence of any one of SEQ ID NOs: 1-15 (e.g., SEQ ID NOs: 2-15)), fused to a moiety. The moiety may increase stability or improve pharmacokinetic properties of the polypeptide. The moiety (e.g., Fc domain monomer, a wild-type Fc domain, an Fc domain with amino acid substitutions (e.g., one or more substitutions that reduce dimerization), an albumin-binding peptide, a fibronectin domain, or a human serum albumin) may be fused to the polypeptide by way of a linker. A linker can be a covalent bond or a spacer. The term "bond" refers to a chemical bond, e.g., an amide bond or a disulfide bond, or any kind of bond created from a chemical reaction, e.g., chemical conjugation. The term "spacer" refers to a moiety (e.g., a polyethylene glycol (PEG) polymer) or an amino acid sequence (e.g., a 1-200 amino acid sequence) occurring between two elements, e.g., peptides or protein domains, to provide space and/or flexibility between the two elements. An amino acid spacer is part of the primary sequence of a polypeptide (e.g., fused to the spaced peptides via the polypeptide backbone). The formation of disulfide bonds, e.g., between two hinge regions that form an Fc domain, is not considered a linker.

As used herein, the term "Fc domain" refers to a dimer of two Fc domain monomers. An Fc domain has at least 80% sequence identity (e.g., at least 85%, 90%, 95%, 97%, or 100% sequence identity) to a human Fc domain that includes at least a CH$_2$ domain and a CH$_3$ domain. An Fc domain monomer includes second and third antibody constant domains (CH₂ and CH₃). In some embodiments, the Fc domain monomer also includes a hinge domain. An Fc domain does not include any portion of an immunoglobulin that is capable of acting as an antigen-recognition region, e.g., a variable domain or a complementarity determining region (CDR). In the wild-type Fc domain, the two Fc domain monomers dimerize by the interaction between the two CH₃ antibody constant domains, as well as one or more disulfide bonds that form between the hinge domains of the two dimerizing Fc domain monomers. In some embodiments, an Fc domain may be mutated to lack effector functions, typical of a "dead Fc domain." In certain embodiments, each of the Fc domain monomers in an Fc domain includes amino acid substitutions in the CH₂ antibody constant domain to reduce the interaction or binding between the Fc domain and an Fcγ receptor. In some embodiments, the Fc domain contains one or more amino acid substitutions that reduce or inhibit Fc domain dimerization. An Fc domain can be any immunoglobulin antibody isotype, including IgG, IgE, IgM, IgA, or IgD. Additionally, an Fc domain can be an IgG subtype (e.g., IgG1, IgG2a, IgG2b, IgG3, or IgG4). The Fc domain can also be a non-naturally occurring Fc domain, e.g., a recombinant Fc domain.

As used herein, the term "albumin-binding peptide" refers to an amino acid sequence of 12 to 16 amino acids that has affinity for and functions to bind serum albumin. An albumin-binding peptide can be of different origins, e.g., human, mouse, or rat. In some embodiments, an albumin-binding peptide has the sequence DICLPRWGCLW (SEQ ID NO: 72).

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell, e.g., a human hair cell).

As used herein, the term "fibronectin domain" refers to a high molecular weight glycoprotein of the extracellular matrix, or a fragment thereof, that binds to, e.g., membrane-spanning receptor proteins such as integrins and extracellular matrix components such as collagens and fibrins. In some embodiments, a fibronectin domain is a fibronectin type III domain (SEQ ID NO: 73) having amino acids 610-702 of the sequence of UniProt ID NO: P02751. In other embodiments, a fibronectin domain is an adnectin protein.

As used herein, the term "human serum albumin" refers to the albumin protein present in human blood plasma. Human serum albumin is the most abundant protein in the blood. It constitutes about half of the blood serum protein. In some embodiments, a human serum albumin has the sequence of UniProt ID NO: P02768 (SEQ ID NO: 74).

As used herein, the term "fused" is used to describe the combination or attachment of two or more elements, components, or protein domains, e.g., peptides or polypeptides, by means including chemical conjugation, recombinant means, and chemical bonds, e.g., amide bonds. For example, two single peptides in tandem series can be fused to form one contiguous protein structure, e.g., a polypeptide, through chemical conjugation, a chemical bond, a peptide linker, or any other means of covalent linkage. In some embodiments of a polypeptide described herein, an extracellular ActRIIB variant (e.g., an extracellular ActRIIB variant having the sequence of any one of SEQ ID NOs: 1-15 (e.g., SEQ ID NOs: 2-15)), may be fused in tandem series to the N- or C-terminus of a moiety (e.g., Fc domain monomer (e.g., the sequence of SEQ ID NO: 19) a wild-type Fc domain (e.g., the sequence of SEQ ID NO: 71), an Fc domain with amino acid substitutions (e.g., one or more substitutions that reduce dimerization), an albumin-binding peptide (e.g., the sequence of SEQ ID NO: 72), a fibronectin domain (e.g., the sequence of SEQ ID NO: 73), or a human serum albumin (e.g., the sequence of SEQ ID NO: 74)) by way of a linker. For example, an extracellular ActRIIB variant is fused to a moiety (e.g., an Fc domain monomer, a wild-type Fc domain, an Fc domain with amino acid substitutions (e.g., one or more substitutions that reduce dimerization), an albumin-binding peptide, a fibronectin domain, or a human serum albumin) by way of a peptide linker, in which the N-terminus of the peptide linker is fused to the C-terminus of the extracellular ActRIIB variant through a chemical bond, e.g., a peptide bond, and the C-terminus of the peptide linker is fused to the N-terminus of the moiety (e.g., Fc domain monomer, wild-type Fc domain, Fc domain with amino acid substitutions (e.g., one or more substitutions that reduce dimerization), albumin-binding peptide, fibronectin domain, or human serum albumin) through a chemical bond, e.g., a peptide bond.

As used herein, the terms "bone mineral density (BMD)," "bone density," and "bone mass" refer to a measure of the amount of bone mineral (e.g., calcium) in bone tissue. BMD may be measured by well-established clinical techniques known to one of skill in the art (e.g., by single-1 or dual-energy photon or X-ray absorptiometry). The concept of BMD relates to the mass of mineral per volume of bone, although clinically it is measured by proxy according to optical density per square centimeter of bone surface upon imaging. BMD measurement is used in clinical medicine as an indirect indicator of osteoporosis and fracture risk. In some embodiments, BMD test results are provided as a T-score, where the T-score represents the BMD of a subject compared to the ideal or peak bone mineral density of a healthy 30-year-old adult. A score of 0 indicates that the BMD is equal to the normal reference value for a healthy young adult. Differences between the measured BMD of subject and that of the reference value for a healthy young adult are measured in standard deviations units (SDs). Accordingly, a T-score of between +1 SD and −1 SD may indicate a normal BMD, a T-score of between −1 SD and −2.5 SD may indicate low bone 30 mass (e.g., osteopenia), and a T-score lower than −2.5 SD may indicate osteoporosis or severe osteoporosis. In some embodiments, a polypeptide of the invention including an extracellular ActRIIB variant (e.g., an extracellular ActRIIB variant having the sequence of any one of SEQ ID NOs: 1-15 (e.g., SEQ ID NOs: 2-15)), a nucleic acid encoding such a polypeptide, or a vector containing such a nucleic acid molecule is administered to a subject in need thereof, wherein the patient has low bone mass (e.g., a T-Score of between −1 SD and −2.5 SD). In some embodiments, a polypeptide of the invention including an extracellular ActRIIB variant (e.g., an extracellular ActRIIB variant having the sequence of any one of SEQ ID NOs: 1-15 (e.g., SEQ ID NOs: 2-15)), a nucleic acid encoding such a polypeptide, or a vector containing such a nucleic acid molecule is administered to a subject in need thereof, wherein the patient has osteoporosis (e.g., a T-Score of less than −2.5 SD). In some embodiments, administration of a polypeptide of the invention including an extracellular ActRIIB variant (e.g., an extracellular ActRIIB variant having the sequence of any one of SEQ ID NOs: 1-15 (e.g., SEQ ID NOs: 2-15)), a nucleic acid encoding such a polypeptide, or a vector containing such a nucleic acid molecule treats the subject by increasing their BMD. In some embodiments, administration of a polypeptide of the invention including an extracellular ActRIIB variant (e.g., an extracellular ActRIIB variant having the sequence of any one of SEQ ID NOs: 1-15 (e.g., SEQ ID NOs: 2-15)), a nucleic acid encoding such a polypeptide, or a vector containing such a nucleic acid molecule increases the BMD of a subject resulting in an increase in the T-Score of the subject (e.g., resulting in an increase in the T-Score of the subject of 0.1 or more, 0.2 or more, 0.3 or more, 0.4 or more, 0.5 or more, 1.0 or more, or 2.0 or more).

As used herein, the term "bone strength" refers to a measurement of bone that is determined by bone quality in addition to bone mineral density. Bone quality is influenced by bone geometry, microarchitecture, and the properties of constituent tissues. Bone strength can be used to assess the bone's risk of fracture.

As used herein, the term "bone disease" refers to a condition characterized by bone damage (e.g., decreased bone mineral density, decreased bone strength, and/or bone loss). Such diseases or conditions may be caused by an imbalance in osteoblast and/or osteoclast activity (e.g., increased bone resorption or reduced bone formation). Bone diseases include primary osteoporosis, secondary osteoporosis, osteopenia, osteopetrosis, bone fracture, bone cancer or cancer metastasis-related bone loss (e.g., bone loss associated with multiple myeloma), Paget's disease, renal osteodystrophy, treatment-related bone loss, diet-related bone loss, bone loss associated with the treatment of obesity, low gravity-related bone loss, and immobility-related bone loss.

As used herein, the terms "bone remodeling" or "bone metabolism" refer to the process for maintaining bone strength and ion homeostasis by replacing discrete parts of old bone with newly synthesized packets of proteinaceous matrix. Bone is resorbed by osteoclasts, and is deposited by osteoblasts in a process called ossification. Osteocyte activity plays a key role in this process. Conditions that result in a decrease in bone mass, can either be caused by an increase in resorption, or a decrease in ossification. In a healthy individual, during childhood, bone formation exceeds resorption. As the aging process occurs, resorption exceeds formation. Bone resorption rates are also typically much higher in post-menopausal older women due to estrogen deficiency related to menopause.

As used herein, the terms "bone resorption" or "bone catabolic activity" refer to a process by which osteoclasts break down the tissue in bones and release the minerals, resulting in a transfer of the mineral (e.g., calcium) from bone tissue to the blood. Increased rates of bone resorption are associated with aging, including in post-menopausal women. High rates of bone resorption, or rates of bone resorption that exceed the rate of ossification, are associated with bone disorders, such as decreased bone mineral density, including osteopenia and osteoporosis, and can result in bone loss. In some embodiments, a polypeptide of the invention including an extracellular ActRIIB variant (e.g., an extracellular ActRIIB variant having the sequence of any one of SEQ ID NOs: 1-15 (e.g., SEQ ID NOs: 2-15)), a nucleic acid encoding such a polypeptide, or a vector containing such a nucleic acid molecule is administered to a subject in need thereof to decrease bone resorption (e.g., decrease bone loss) in the subject (e.g., the amount or rate of bone resorption in the subject).

As used herein, the terms "bone formation," "ossification," "osteogenesis," or "bone anabolic activity" refer to the process of forming new bone tissue by osteoblasts. In some embodiments, a polypeptide of the invention including an extracellular ActRIIB variant (e.g., an extracellular ActRIIB variant having the sequence of any one of SEQ ID NOs: 1-15 (e.g., SEQ ID NOs: 2-15)), a nucleic acid encoding such a polypeptide, or a vector containing such a nucleic acid molecule is administered to a subject in need thereof, to increase bone formation (e.g., increase the amount or rate of bone formation or osteogenesis in the subject). Reduced rates of bone formation, or rates of bone formation that are exceeded by the rate of bone resorption, can result in bone loss.

As used herein, the terms "increasing" and "decreasing" refer to modulating resulting in, respectively, greater or lesser amounts, of function, expression, or activity of a metric relative to a reference. For example, subsequent to administration of a polypeptide of the invention including an extracellular ActRIIB variant in a method described herein, the amount of a marker of a metric (e.g., lean mass) as described herein may be increased or decreased in a subject relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "fibrosis" refers to the pathological process of excess formation of fibrous connective tissue. Fibrosis is characterized by fibroblast accumulation and collagen deposition in excess of normal deposition in any particular tissue. In response to inflammation or an injury to a tissue, nearby fibroblasts can migrate into the wound, proliferate, and produce large amounts of collagenous extracellular matrix. When fibrosis occurs in response to injury, the term "scarring" can be used as synonym. Fibrosis may occur in many tissues of the body, including, e.g., lungs, skin, liver, kidney, heart, eye, tendon, cartilage, pancreatic tissue, uterine tissue, neural tissue, testis, ovary, adrenal gland, artery, vein, colon, small and large intestine, biliary tract, and gut.

As used herein, the terms "pulmonary hypertension" or "PH" refer to a disease characterized by an increase in blood pressure between the heart and lungs, which can include an increase in blood pressure in pulmonary arteries (pulmonary arterial hypertension), pulmonary veins, or pulmonary capillaries. Pulmonary hypertension can have a number of symptoms, shortness of breath (dyspnea), fatigue, swelling (e.g., edema) of the legs, feet, belly (ascites), or neck, chest pain or pressure, racing pulse or heart palpitations, bluish color to lips or skin (cyanosis), dizziness, or fainting. PH also features reduce exercise tolerance and may lead to heart failure.

As used herein, the terms "pulmonary arterial hypertension" or "PAH" refer to a form of pulmonary hypertension characterized by a narrowing or obstruction in the small pulmonary arteries, often caused by scarring, and an increase in pulmonary arterial blood pressure. PAH is also known as WHO Group I PH. PAH can be diagnosed based on an increase in blood pressure in the pulmonary artery mean pulmonary arterial pressure above 25 mmHg at rest, with a normal pulmonary artery capillary wedge pressure. PAH can lead to shortness of breath, dizziness, fainting, and other symptoms, all of which are exacerbated by exertion. PAH can be a severe disease with a markedly decreased exercise tolerance and heart failure. Two major types of PAH include idiopathic PAH (e.g., PAH in which no predisposing factor is identified) and heritable PAH (e.g., PAH associated with a mutation in BMPR2, ALK1, SMAD9, caveolin 1, KCNK3, or EIF2AK4). In 70% of familial PAH cases, mutations are located in the BMPR2 gene. Risk factors for the development of PAH include family history of PAH, drug use (e.g., methamphetamine or cocaine use), infection (e.g., HIV infection or schistosomiasis), cirrhosis of the liver, congenital heart abnormalities, portal hypertension, pulmonary veno-occlusive disease, pulmonary capillary hemangiomatosis, or connective tissue/autoimmune disorders (e.g., scleroderma or lupus).

As used herein, the terms "venous pulmonary hypertension" and "venous PH" refer to a form of pulmonary hypertension that is secondary to left heart disease. Venous PH is also known as WHO Group II PH. Venous PH may be associated with or caused by left ventricular systolic dysfunction (e.g., failure of the left ventricle), left ventricular diastolic dysfunction, valvular heart disease (e.g., mitral valve or aortic valve disease), congenital cardiomyopathy, or congenital/acquired pulmonary venous stenosis.

As used herein, the terms "hypoxic pulmonary hypertension" and "hypoxic PH" refer to a form of pulmonary hypertension that is due to lung disease or chronic hypoxia. This form of PH is also known as WHO Group III PH. Hypoxic PH may be associated with or caused by chronic obstructive pulmonary disease (e.g., emphysema), interstitial lung disease, sleep-disordered breathing (e.g., sleep apnea), lung disease (e.g., pulmonary fibrosis), alveolar hypoventilation disorders, chronic exposure to high altitude, or developmental abnormalities.

As used herein, the terms "thromboembolic pulmonary hypertension" and "thromboembolic PH" refer to a form of pulmonary hypertension that is related to chronic arterial obstruction (e.g., blood clots). Thromboembolic PH is also known as WHO Group IV PH. Thromboembolic PH may be associated with or caused by chronic thromboembolic pulmonary hypertension, or other pulmonary artery obstructions (e.g., pulmonary emboli, angiosarcoma, arteritis, congenital pulmonary artery stenosis, or parasitic infection).

As used herein, the terms "miscellaneous pulmonary hypertension" and "miscellaneous PH" refer to a form of pulmonary hypertension with unclear or multifactorial mechanisms. This form of PH is categorized as WHO Group V PH. Miscellaneous PH may be associated with or caused by a sarcoidosis, pulmonary Langerhans cell histiocytosis, lymphangioleiomyomatosis, neurofibromatosis, or vasculitis), a metabolic disorder (e.g., glycogen storage disease, Gaucher disease, or thyroid diseases), pulmonary tumoral thrombotic microangiopathy, fibrosing mediastinitis, chronic kidney failure, or segmental pulmonary hypertension.

As used herein, the terms "increase red blood cell levels" and "promote red blood cell formation" refer to clinically observable metrics, such as hematocrit, red blood cell counts, and hemoglobin measurements, and are intended to be neutral as to the mechanism by which such changes occur. The term "low red blood cell levels" as used herein refers to red blood cell counts, hematocrit, and hemoglobin measurements that are below the range of values that is considered normal for the subject's age and gender.

As used herein, the terms "red blood cell formation" and "red blood cell production" refer to the generation of red blood cells, such as the process of erythropoiesis in which red blood cells are produced in the bone marrow.

As used herein, the term "anemia" refers to any abnormality in hemoglobin or red blood cells that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels.

As used herein, the term "percent (%) identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

As used herein, the term "serum half-life" refers to, in the context of administering a therapeutic protein to a subject, the time required for plasma concentration of the protein in the subject to be reduced by half. The protein can be redistributed or cleared from the bloodstream, or degraded, e.g., by proteolysis. As described herein, a polypeptide including an extracellular ActRIIB variant having the sequence of any one of SEQ ID NOs: 1-15 (e.g., SEQ ID NOs: 2-15) displays a serum half-life of 7 days in humans.

As used herein, the term "lean mass" refers to a component of body composition which includes, e.g., lean mass, body fat, and body fluid. Normally lean mass is calculated by subtracting the weights of body fat and body fluid from total body weight. Typically, a subject's lean mass is between 60% and 90% of totally body weight. In the present invention, administration of a polypeptide including an extracellular ActRIIB variant having the sequence of any one of SEQ ID NOs: 1-15 (e.g., SEQ ID NOs: 2-15), a nucleic acid molecule encoding a polypeptide including an extracellular ActRIIB variant (e.g., extracellular ActRIIB variant having the sequence of any one of SEQ ID NOs:

1-15 (e.g., SEQ ID NOs: 2-15), or vector containing such a nucleic acid molecule to a subject increases the subject's lean mass.

As used herein, the term "affinity" or "binding affinity" refers to the strength of the binding interaction between two molecules. Generally, binding affinity refers to the strength of the sum total of non-covalent interactions between a molecule and its binding partner, such as an extracellular ActRIIB variant and BMP9 or activin A. Unless indicated otherwise, binding affinity refers to intrinsic binding affinity, which reflects a 1:1 interaction between members of a binding pair. The binding affinity between two molecules is commonly described by the dissociation constant ($K_D$) or the affinity constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. The $K_D$ of two interacting molecules may be determined using methods and techniques well known in the art, e.g., surface plasmon resonance. $K_D$ is calculated as the ratio of $k_{off}/k_{on}$.

As used herein, the term "muscle mass" refers to a component of body composition. Normally muscle mass is calculated by subtracting the weights of body fat and body fluid from total body weight. The percentage of muscle mass may vary greatly among individuals depending on a subject's genetic makeup, age, race, and health status, etc. Typically, a subject's muscle mass may be between 20% and 50% of totally body weight.

As used herein, the phrase "affecting myostatin, activin, and/or BMP9 signaling" means changing the binding of myostatin, activin, and/or BMP9 to their receptors, e.g., ActRIIA, ActRIIB, and BMPRII (e.g., endogenous ActRIIB). In some embodiments, a polypeptide including an extracellular ActRIIB variant described herein reduces or inhibits the binding of myostatin, activin, and/or BMP9 to their receptors, e.g., ActRIIA, ActRIIB, and BMPRII (e.g., endogenous ActRIIB). As described herein, a polypeptide of the invention including an extracellular ActRIIB variant having the sequence of any one of SEQ ID NOs: 1-15 (e.g., SEQ ID NOs: 2-15) may have weak binding affinity to BMP9 (e.g., $K_D$ of 200 μM or higher).

As used herein, the term "vascular complication" refers to a vascular disorder or any damage to the blood vessels, such as damage to the blood vessel walls. Damage to the blood vessel walls may cause an increase in vascular permeability or leakage. The term "vascular permeability or leakage" refers to the capacity of the blood vessel walls to allow the flow of small molecules, proteins, and cells in and out of blood vessels. An increase in vascular permeability or leakage may be caused by an increase in the gaps (e.g., an increase in the size and/or number of the gaps) between endothelial cells that line the blood vessel walls and/or thinning of the blood vessel walls.

As used herein, the term "polypeptide" describes a single polymer in which the monomers are amino acid residues which are covalently conjugated together through amide bonds. A polypeptide is intended to encompass any amino acid sequence, either naturally occurring, recombinant, or synthetically produced.

As used herein, the term "homodimer" refers to a molecular construct formed by two identical macromolecules, such as proteins or nucleic acids. The two identical monomers may form a homodimer by covalent bonds or non-covalent bonds. For example, an Fc domain may be a homodimer of two Fc domain monomers if the two Fc domain monomers contain the same sequence. In another example, a polypeptide described herein including an extracellular ActRIIB variant fused to an Fc domain monomer may form a homodimer through the interaction of two Fc domain monomers, which form an Fc domain in the homodimer.

As used herein, the term "heterodimer" refers to a molecular construct formed by two different macromolecules, such as proteins or nucleic acids. The two monomers may form a heterodimer by covalent bonds or non-covalent bonds. For example, a polypeptide described herein including an extracellular ActRIIB variant fused to an Fc domain monomer may form a heterodimer through the interaction of two Fc domain monomers, each fused to a different ActRIIB variant, which form an Fc domain in the heterodimer.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell or a HEK293 cell).

As used herein, the term "therapeutically effective amount" refers an amount of a polypeptide, nucleic acid, or vector of the invention or a pharmaceutical composition containing a polypeptide, nucleic acid, or vector of the invention effective in achieving the desired therapeutic effect in treating a patient having a or at risk of developing a disease, such as a muscle disease, a condition involving weakness and atrophy of muscles, e.g., Duchenne muscular dystrophy (DMD), facioscapulohumeral muscular dystrophy (FSHD), inclusion body myositis (IBM), amyotrophic lateral sclerosis (ALS), sarcopenia, or cancer cachexia, a disease or condition involving bone damage (e.g., osteoporosis, or a condition involving bone damage, e.g., primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss), a disease or condition involving low red blood cell levels (e.g., anemia or blood loss), a disease or condition involving fibrosis, or PH (e.g., PAH, venous PH, hypoxic PH, thromboembolic PH, or miscellaneous PH). In particular, the therapeutically effective amount of the polypeptide, nucleic acid, or vector avoids adverse side effects.

As used herein, the term "pharmaceutical composition" refers to a medicinal or pharmaceutical formulation that includes an active ingredient as well as excipients and diluents to enable the active ingredient suitable for the method of administration. The pharmaceutical composition of the present invention includes pharmaceutically acceptable components that are compatible with the polypeptide, nucleic acid, or vector. The pharmaceutical composition may be in tablet or capsule form for oral administration or in aqueous form for intravenous or subcutaneous administration.

As used herein, the term "pharmaceutically acceptable carrier or excipient" refers to an excipient or diluent in a pharmaceutical composition. The pharmaceutically acceptable carrier must be compatible with the other ingredients of the formulation and not deleterious to the recipient. In the present invention, the pharmaceutically acceptable carrier or excipient must provide adequate pharmaceutical stability to the polypeptide including an extracellular ActRIIB variant, the nucleic acid molecule(s) encoding the polypeptide, or a vector containing such nucleic acid molecule(s). The nature of the carrier or excipient differs with the mode of administration. For example, for intravenous administration, an aqueous solution carrier is generally used; for oral administration, a solid carrier is preferred.

As used herein, the term "treating and/or preventing" refers to the treatment and/or prevention of a disease, e.g., a muscle disease (e.g., DMD, FSHD, IBM, and ALS), a bone disease (e.g., a disease or condition involving bone damage, e.g., osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss), a disease involving low blood cell levels (e.g., anemia or blood loss), fibrosis, or PH (e.g., PAH, venous PH, hypoxic PH, thromboembolic PH, or miscellaneous PH) using methods and compositions of the invention. Generally, treating a muscle, bone, low blood cell, or fibrotic disease, or PH (e.g., PAH, venous PH, hypoxic PH, thromboembolic PH, or miscellaneous PH) occurs after a subject has developed the muscle, bone, low blood cell, or fibrotic disease, or PH (e.g., PAH, venous PH, hypoxic PH, thromboembolic PH, or miscellaneous PH) and/or is already diagnosed with the muscle, bone, low blood cell, or fibrotic disease, or PH (e.g., PAH, venous PH, hypoxic PH, thromboembolic PH, or miscellaneous PH). Preventing a muscle, bone, low blood cell, or fibrotic disease, or PH (e.g., PAH, venous PH, hypoxic PH, thromboembolic PH, or miscellaneous PH) refers to steps or procedures taken when a subject is at risk of developing the muscle, bone, low blood cell, or fibrotic disease, or PH (e.g., PAH, venous PH, hypoxic PH, thromboembolic PH, or miscellaneous PH). The subject may show signs or mild symptoms that are judged by a physician to be indications or risk factors for developing the muscle, bone, low blood cell, or fibrotic disease, or PH (e.g., PAH, venous PH, hypoxic PH, thromboembolic PH, or miscellaneous PH), have another disease or condition associated with the development of the muscle, bone, low blood cell, or fibrotic disease, or PH (e.g., PAH, venous PH, hypoxic PH, thromboembolic PH, or miscellaneous PH), be undergoing treatment that may cause anemia, fibrosis, or loss of bone density (e.g., surgery, chemotherapy, or radiation), or have a family history or genetic predisposition to developing the muscle, bone, low blood cell, or fibrotic disease, or PH (e.g., PAH, venous PH, hypoxic PH, thromboembolic PH, or miscellaneous PH), but has not yet developed the disease.

As used herein, the term "subject" refers to a mammal, e.g., preferably a human. Mammals include, but are not limited to, humans and domestic and farm animals, such as monkeys (e.g., a cynomolgus monkey), mice, dogs, cats, horses, and cows, etc.

DESCRIPTION OF THE DRAWINGS

FIG. 1 is a sequence alignment showing the wild-type sequences of extracellular ActRIIA and ActRIIB and the amino acid substitutions in the ActRIIB variants. FIG. 1 also displays the percent body weight change resulting from treatment of a mouse with the corresponding variant.

FIG. 2 is a bar graph depicting the effects of extracellular ActRIIB variants on body weight at the end of 28 days. Mice received a single hydrodynamic injection of a plasmid construct encoding the indicated ActRIIB variant or a control plasmid. The legend lists the bars of the bar graph from left to right ("Vehicle" is the bar closest to the y-axis and "pLEV-113-ActRIIb-2.10" is the bar furthest from the y-axis).

FIGS. 5A-5C are a series of graphs depicting the effects of ActRIIB variants ActRIIB 2.11-Fc and ActRIIB 2.12-Fc on red blood cell count, hemoglobin levels, and hematocrit.

FIGS. 7A-7C are a series of graphs depicting the effects of ActRIIB variant ActRIIB 2.12-Fc on parameters of red cell mass in wild-type rats.

FIGS. 8A-8E are a series of graphs depicting the effects of ActRIIB variant ActRIIB 2.12-Fc on trabecular bone in wild-type rats.

DETAILED DESCRIPTION OF THE INVENTION

Figure 3A:
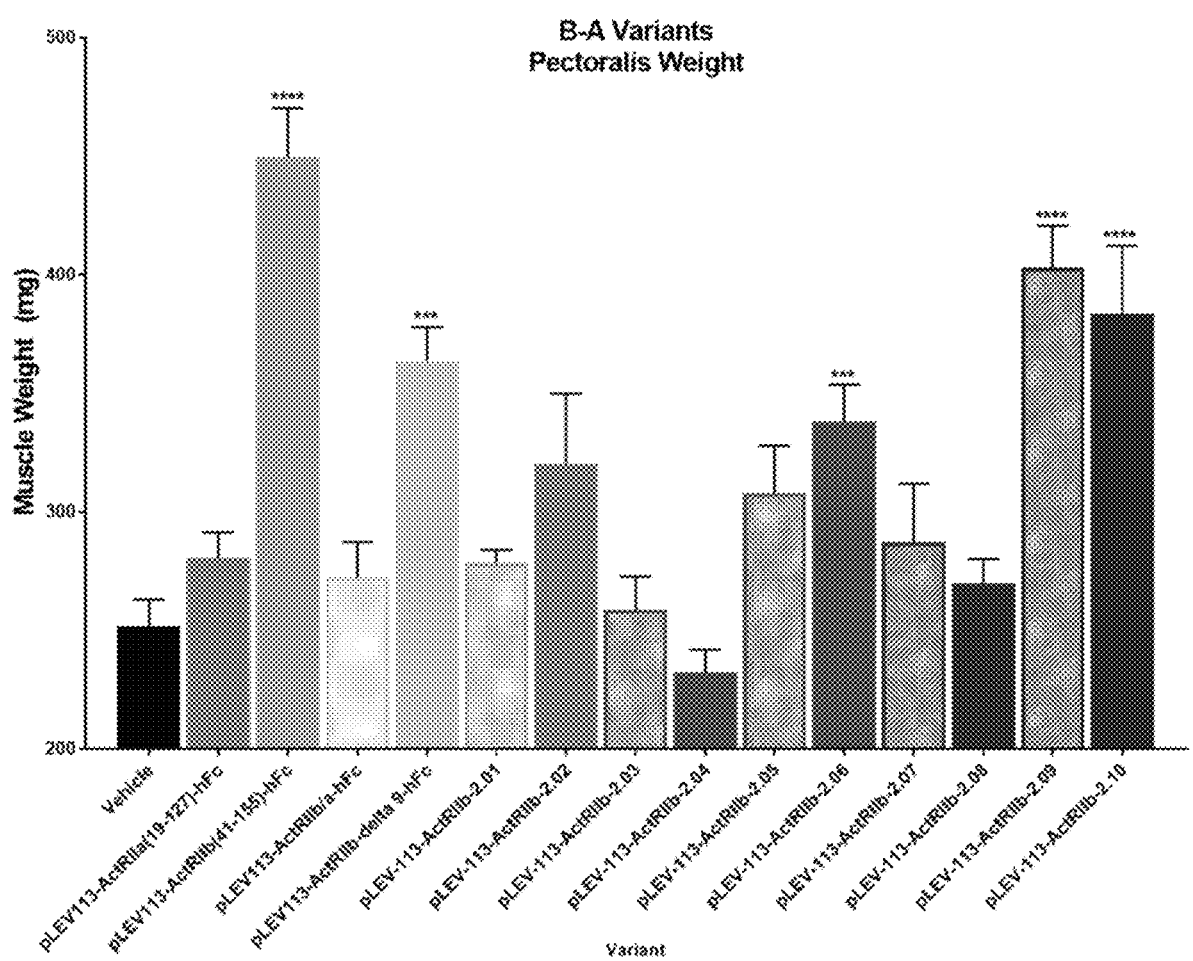
FIGS. 3A and 3B are bar graphs depicting the effects of extracellular ActRIIB variants on individual muscle weights by tissue analysis.

The invention features polypeptides that include an extracellular activin receptor type IIB (ActRIIB) variant. In some embodiments, a polypeptide of the invention includes an extracellular ActRIIB variant fused to a moiety (e.g., Fc domain monomer, a wild-type Fc domain, an Fc domain with amino acid substitutions (e.g., one or more substitutions that reduce dimerization), an albumin-binding peptide, a fibronectin domain, or a human serum albumin). A polypeptide including an extracellular ActRIIB variant fused to an Fc domain monomer may also form a dimer (e.g., homodimer or heterodimer) through the interaction between two Fc domain monomers. The ActRIIB variants described herein may have reduced binding to bone morphogenetic protein 9 (BMP9) relative to the wild-type extracellular ActRIIB, or have weak binding affinity or no binding affinity to BMP9 compared to binding affinity to activins and myostatin. The invention also includes methods of treating diseases and conditions involving weakness and atrophy of muscles by increasing muscle mass and strength, methods of treating or preventing bone damage by increasing bone mineral density, increasing bone formation, or decreasing bone resorption, methods of treating or preventing fibrosis, methods of treating or preventing low blood cell levels (e.g., anemia or blood loss) by increasing red blood cell levels (e.g., red blood cell count, hemoglobin levels, or hematocrit) or red blood cell production, methods of treating or preventing pulmonary hypertension (PH) (e.g., PAH, venous PH, hypoxic PH, thromboembolic PH, or miscellaneous PH), or methods of affecting myostatin, activin, and/or BMP9 signaling in a subject by administering to the subject a polypeptide including an extracellular ActRIIB variant described herein.

I. Extracellular Activin Receptor Type IIB Variants

Activin type II receptors are single transmembrane domain receptors that modulate signals for ligands in the transforming growth factor β (TGF-β) superfamily. Ligands in the TGF-β superfamily are involved in a host of physiological processes, such as muscle growth, vascular growth, cell differentiation, homeostasis, and osteogenesis. Examples of ligands in the TGF-β superfamily include, e.g., activin (e.g., activin A and activin B), inhibin, growth differentiation factors (GDFs) (e.g., GDF8, also known as myostatin), and bone morphogenetic proteins (BMPs) (e.g., BMP9). Myostatin and activins are known to play a role in the regulation of skeletal muscle growth. For example, mice without myostatin show a large increase in skeletal muscle mass. Myostatin has also been implicated in promoting fibrosis. For example, mice lacking myostatin show a reduction in muscle fibrosis, and injection of myostatin-coated beads induces muscle fibrosis in mice. Mice overexpressing an activin subunit that leads to production of diffusible activin A also exhibit fibrosis. In addition, activins are expressed abundantly in bone tissues and regulate bone formation by controlling both osteoblast and osteoclast functions. Activin has been reported to be upregulated in bone disease and inhibits osteoblast activity. Myostatin is also implicated in bone homeostasis through increasing osteogenesis and inhibiting osteoblast activity. Elevated activin A has also been observed in clinical and experimental pulmonary hypertension. Methods that reduce or inhibit activin or myostatin signaling could, therefore, be used in the treatment of diseases and conditions involving muscle atrophy or weakness, fibrosis, bone damage, low red blood cell levels (e.g., anemia), or pulmonary hypertension (e.g., PAH, venous PH, hypoxic PH, thromboembolic PH, or miscellaneous PH).

There exist two types of activin type II receptors: ActRIIA and ActRIIB. Studies have shown that BMP9 binds ActRIIB with about 300-fold higher binding affinity than ActRIIA (see, e.g., Townson et al., *J. Biol. Chem.* 287:27313, 2012). ActRIIA is known to have a longer half-life compared to ActRIIB. The present invention describes extracellular ActRIIB variants that are constructed by introducing amino acid residues of ActRIIA into ActRIIB, or by introducing novel amino acid substitutions, with the goal of reducing BMP9 binding to prevent or reduce disruption of endogenous BMP9 signaling. The amino acid substitutions may also impart beneficial physiological and pharmacokinetic properties of ActRIIA, such as longer half-life or the capability to increase red blood cell levels. The optimum peptides confer significant increases in lean mass, muscle mass, bone mineral density, and/or red blood cell levels (e.g., increase red blood cell production), a decrease in fibrosis, or treat PH (e.g., PAH, venous PH, hypoxic PH, thromboembolic PH, or miscellaneous PH), while having reduced binding affinity to BMP9, for example. The preferred ActRIIB variants also exhibit similar or improved binding to activins and/or myostatin compared to wild-type ActRIIB, which allows them to compete with endogenous activin receptors for ligand binding and reduce or inhibit endogenous activin receptor signaling. These variants can be used to treat disorders in which activin receptor signaling is elevated, such as bone disease (e.g., diseases or conditions involving bone damage), muscle disease, fibrosis, PH (e.g., PAH, venous PH, hypoxic PH, thromboembolic PH, or miscellaneous PH), and/or anemia, leading to a reduction in bone resorption or osteoclast activity, an increase in bone formation or bone mineral density, an increase in muscle mass or strength, reduction in fibrosis (e.g., reduced fibrosis or a slowing or stopping of the progression of fibrosis), an increase red blood cell levels (e.g., an increase in hemoglobin levels, hematocrit, or red blood cell counts, e.g., an increase in red blood cell production), or a reduction in the symptoms or progression of PH (e.g., PAH, venous PH, hypoxic PH, thromboembolic PH, or miscellaneous PH). In some embodiments, amino acid substitutions may be introduced to an extracellular ActRIIB variant to reduce or remove the binding affinity of the variant to BMP9. The wild-type amino acid sequences of the extracellular portions of human ActRIIA and ActRIIB are shown below.

```
Human ActRIIA, extracellular portion (SEQ ID
NO: 16):
GAILGRSETQECLFFNANWEKDRTNQTGVEPCYGDKDKRRHCFATWKNIS

GSIEIVKQGCWLDDINCYDRTDCVEKKDSPEVYFCCCEGNMCNEKFSYFP

EMEVTQPTS

Human ActRIIB, extracellular portion (SEQ ID
NO: 17):
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPT
```

Polypeptides described herein include an extracellular ActRIIB variant having at least one amino acid substitution relative to the wild-type extracellular ActRIIB having the sequence of SEQ ID NO: 17. Possible amino acid substitutions at 28 different positions may be introduced to an extracellular ActRIIB variant (Table 1). An extracellular ActRIIB variant may have one or more (e.g., 1-28, 1-25, 1-23, 1-21, 1-19, 1-17, 1-15, 1-13, 1-11, 1-9, 1-7, 1-5, 1-3, or 1-2; e.g., 1, 2, 3, 4, 5, 6, 7, 8, 9, 10, 11, 12, 13, 14, 15, 16, 17, 18, 19, 20, 21, 22, 23, 24, 25, 26, or 27) amino acid substitutions relative the sequence of a wild-type extracellular ActRIIB (SEQ ID NO: 17). In some embodiments, an extracellular ActRIIB variant (e.g., an extracellular ActRIIB variant having a sequence of SEQ ID NO: 1) may include amino acid substitutions at all of the 28 positions as listed in Table 1. In some embodiments, an extracellular ActRIIB variant may include amino acid substitutions at a number of positions, e.g., at 3, 4, 5, 6, 7, 8, 9, 10, 12, 15, 16, 18, 20, 22, 24, 26, or 27 out of the 28 positions, as listed in Table 1. In some embodiments, the substitutions are substitutions of an amino acid from ActRIIA into the same position in ActRIIB. In some embodiments, the substitutions are novel changes (e.g., substitutions of amino acids that are not in the corresponding position of ActRIIA, e.g., S48T, I51L, Q69D, or E70T).

Amino acid substitutions can worsen or improve the activity and/or binding affinity of the ActRIIB variants of the invention (e.g., an extracellular ActRIIB variant having the sequence of any one of SEQ ID NOs: 1-15 (e.g., SEQ ID NOs: 2-15)). In some embodiments, the amino acid substitutions worsen the binding affinity of the ActRIIB variants to BMP9 (e.g., the variants have reduced binding to BMP9 relative to wild-type extracellular ActRIIB, or have lower binding to BMP9 than to other ActRIIB ligands (e.g., activin A or B, myostatin, or GDF-11)). In some embodiments, the ActRIIB variants have reduced, weak, or no substantial binding to BMP9. In some embodiments, the amino acid substitutions improve the binding affinity of ActRIIB to myostatin, activin A or B, and/or GDF-11 (e.g., the variants have improved binding affinity relative to wild-type extracellular ActRIIB, or bind more strongly to myostatin, activin A or B, or GDF-11 than to BMP9). In some embodiments, the amino acid substitutions reduce the binding affinity of ActRIIB to myostatin, activin A or B, and/or GDF-11 (e.g., the variants have decreased binding affinity relative to wild-type extracellular ActRIIB, or bind more weakly to myostatin, activin A or B, or GDF-11 than to BMP9). In some embodiments, the amino acid substitutions do not substantially change extracellular ActRIIB function (e.g., the ActRIIB variants increase lean mass, muscle, mass, or bone mineral density, or reduce or prevent fibrosis, by a similar amount as wild-type extracellular ActRIIB, e.g., the ActRIIB variants are functionally equivalent to the wild-type extracellular ActRIIB). In some embodiments, the amino acid substitutions confer an ActRIIA property or activity on the ActRIIB variant (e.g., the ActRIIB variant can increase red blood cell levels or has a longer half-life than WT extracellular ActRIIB). Preferably, the ActRIIB variants have one or more, two or more, or three or more of the above properties (e.g., reduced BMP9 binding and improved binding to activin A or B, myostatin, and/or GDF-11, or reduced BMP9 binding and functional equivalence to wild-type ActRIIB in increasing lean mass, muscle mass, or bone mineral density, or reducing or preventing fibrosis).

The ActRIIB variants of the invention (e.g., an extracellular ActRIIB variant having the sequence of any one of SEQ ID NOs: 1-15 (e.g., SEQ ID NOs: 2-15)) preferably have one or more amino acid substitutions that reduce BMP9 binding. In some embodiments, the amino acid substitution that reduces BMP9 binding is E75K (e.g., $X_{24}$ is K in SEQ ID NO: 1). In some embodiments, the amino acid substitutions that reduce BMP9 binding are Q69T and E70D (e.g., $X_{21}$ is T and $X_{22}$ is D in SEQ ID NO: 1). In some embodiments, the amino acid substitutions that reduce BMP9 binding are Q69D and E70T (e.g., $X_{21}$ is D and $X_{22}$ is T in SEQ ID NO: 1). In some embodiments, the amino acid substitutions that reduce BMP9 binding are T74K, E75K, E76D, N77S, and Q79E (e.g., $X_{23}$, $X_{24}$, $X_{25}$, $X_{26}$, and $X_{28}$ are K, K, D, S, and E, respectively, in SEQ ID NO: 1). In some embodiments, the ActRIIB variants have more than one of the aforementioned amino acid substitutions that reduce BMP9 binding (e.g., substitution E75K and substitutions Q69D and E70T, or substitution E75K and substitutions Q69T and E70D). In some embodiments, the ActRIIB variants of the invention have one or more amino acid substitutions that reduce BMP9 binding, and one or more additional amino acid substitutions. The additional amino acid substitutions may confer other beneficial properties, such as altered binding to activins or myostatin or improved activity. For example, amino acid substitutions T74K, E75K, E76D, N77S, and Q79E lead to a reduction in ActRIIB variant activity (e.g., the variant has a reduced effect on lean mass and muscle mass compared to wild-type extracellular ActRIIB), but including additional substitutions S25T and S47I; E31Y, E33D, and Q34K; or Y41 F, R45K, and K56Q improves the effect of the ActRIIB variant on lean mass and/or muscle mass. The additional amino acid substitutions may include one or more of substitutions I11L, Y12F, L19K, E20D, S25T, L27V, R29P, E31Y, E33D, Q34K, L38R, Y41F, R45K, S47I, S48T, T50S, I51 L, L53I, K56Q and F63I, T74K, E76D, N77S, Q79E, or F89M.

In some embodiments, a polypeptide described herein includes an extracellular ActRIIB variant having the sequence of SEQ ID NO: 1.

In some embodiments, a polypeptide described herein includes an extracellular ActRIIB variant having a sequence of any one of SEQ ID NOs: 2-15 (Table 2).

TABLE 1

Amino acid substitutions in an extracellular ActRIIB variant having a sequence of SEQ ID NO: 1

GRGEAETRECX$_1$X$_2$YNANWEX$_3$X$_4$RTNQX$_5$GX$_6$EX$_7$CX$_8$GX$_9$X$_{10}$DKRX$_{11}$HC
X$_{12}$ASWX$_{13}$NX$_{14}$X$_{15}$GX$_{16}$X$_{17}$EX$_{18}$VKX$_{19}$GCWLDDX$_{20}$NCYDRX$_{21}$X$_{22}$CVA
X$_{23}$X$_{24}$X$_{25}$X$_{26}$PX$_{27}$VYFCCCEGNX$_{28}$CNERFTHLPEAGGPEVTYEPPPTA
PT (SEQ ID NO: 1)

| | |
|---|---|
| $X_1$ | I or L |
| $X_2$ | F or Y |
| $X_3$ | L or K |
| $X_4$ | D or E |
| $X_5$ | T or S |
| $X_6$ | L or V |
| $X_7$ | P or R |
| $X_8$ | Y or E |
| $X_9$ | D or E |
| $X_{10}$ | K or Q |
| $X_{11}$ | R or L |
| $X_{12}$ | Y or F |
| $X_{13}$ | R or K |
| $X_{14}$ | S or I |
| $X_{15}$ | S or T |
| $X_{16}$ | S or T |
| $X_{17}$ | I or L |
| $X_{18}$ | I or L |
| $X_{19}$ | K or Q |
| $X_{20}$ | F or I |
| $X_{21}$ | Q, T, or D |
| $X_{22}$ | E, D, or T |
| $X_{23}$ | K or T |
| $X_{24}$ | K or E |
| $X_{25}$ | D or E |
| $X_{26}$ | S or N |
| $X_{27}$ | E or Q |
| $X_{28}$ | F or M |

TABLE 2

Extracellular ActRIIB variants having the sequences of SEQ ID NOs: 2-15

| SEQ ID NO | Amino Acid Sequence |
|---|---|
| 2 | GRGEAETRECIFYNANWEKDRTNQSGLEPCYGDQDKRRHCFASWKNSSGTIELVK QGCWLDDINCYDRQECVAKKDSPEVYFCCCEGNFCNERFTHLPEAGGPEVTYEP PPTAPT |

TABLE 2-continued

Extracellular ActRIIB variants having the sequences of SEQ ID NOs: 2-15

| SEQ ID NO | Amino Acid Sequence |
|---|---|
| 3 | GRGEAETRECIYYNANWELDRTNQSGLERCEGEQDKRLHCYASWRNSSGTIELVKKGCWLDDINCYDRQECVATKENPQVYFCCCEGNFCNERFTHLPEAGGPEVTYEPPPTAPT |
| 4 | GRGEAETRECIYYNANWELERTNQSGLERCEGEQDKRLHCYASWRNSSGTIELVKKGCWLDDFNCYDRQECVAKKDSPEVYFCCCEGNFCNERFTHLPEAGGPEVTYEPPPTAPT |
| 5 | GRGEAETRECIYYNANWELERTNQTGLERCEGEQDKRLHCYASWRNISGTIELVKKGCWLDDFNCYDRQECVAKKDSPEVYFCCCEGNFCNERFTHLPEAGGPEVTYEPPPTAPT |
| 6 | GRGEAETRECIYYNANWELERTNQTGLERCEGEQDKRLHCYASWRNITGTIELVKKGCWLDDFNCYDRQECVAKKDSPEVYFCCCEGNFCNERFTHLPEAGGPEVTYEPPPTAPT |
| 7 | GRGEAETRECIYYNANWELERTNQSGLEPCEGEQDKRLHCYASWRNSSGTIELVKKGCWLDDFNCYDRQECVAKKDSPEVYFCCCEGNFCNERFTHLPEAGGPEVTYEPPPTAPT |
| 8 | GRGEAETRECIYYNANWELERTNQSGLERCYGDKDKRLHCYASWRNSSGTIELVKKGCWLDDFNCYDRQECVAKKDSPEVYFCCCEGNFCNERFTHLPEAGGPEVTYEPPPTAPT |
| 9 | GRGEAETRECIYYNANWELERTNQSGLERCEGEQDKRLHCFASWKNSSGTIELVKQGCWLDDFNCYDRQECVAKKDSPEVYFCCCEGNFCNERFTHLPEAGGPEVTYEPPPTAPT |
| 10 | GRGEAETRECIFYNANWEKDRTNQSGLERCEGEQDKRLHCYASWRNSSGTIELVKKGCWLDDFNCYDRQECVAKKDSPEVYFCCCEGNFCNERFTHLPEAGGPEVTYEPPPTAPT |
| 11 | GRGEAETRECIYYNANWELERTNQSGLERCYGDQDKRRHCYASWRNSSGTIELVKKGCWLDDFNCYDRQECVAKKDSPEVYFCCCEGNFCNERFTHLPEAGGPEVTYEPPPTAPT |
| 12 | GRGEAETRECLYYNANWELERTNQSGVERCEGEKDKRLHCYASWRNSSGSLEIVKKGCWLDDFNCYDRTDCVATEENPQVYFCCCEGNMCNERFTHLPEAGGPEVTYEPPPTAPT |
| 13 | GRGEAETRECLYYNANWELERTNQSGVERCEGEKDKRLHCYASWRNSSGSLEIVKKGCWLDDFNCYDRDTCVATEENPQVYFCCCEGNMCNERFTHLPEAGGPEVTYEPPPTAPT |
| 14 | GRGEAETRECLYYNANWELERTNQSGVERCEGEKDKRLHCYASWRNSSGSLEIVKKGCWLDDFNCYDRDTCVATKENPQVYFCCCEGNMCNERFTHLPEAGGPEVTYEPPPTAPT |
| 15 | GRGEAETRECLYYNANWELERTNQSGVERCEGEKDKRLHCYASWRNSSGSLEIVKKGCWLDDFNCYDRDTCVATKENPQVYFCCCEGNMCNERFTHLPEAGGPEVTYEPPPTAPT |

In some embodiments, a polypeptide of the invention including an extracellular ActRIIB variant may further include a moiety (e.g., Fc domain monomer, a wild-type Fc domain, an Fc domain with amino acid substitutions (e.g., one or more substitutions that reduce dimerization), an albumin-binding peptide, a fibronectin domain, or a human serum albumin), which may be fused to the N- or C-terminus (e.g., C-terminus) of the extracellular ActRIIB variant by way of a linker or other covalent bonds. A polypeptide including an extracellular ActRIIB variant fused to an Fc domain monomer may form a dimer (e.g., homodimer or heterodimer) through the interaction between two Fc domain monomers, which combine to form an Fc domain in the dimer.

Furthermore, in some embodiments, a polypeptide described herein has a serum half-life of at least 7 days in humans. The polypeptide may bind to bone morphogenetic protein 9 (BMP9) with a $K_D$ of 200 μM or higher. The polypeptide may bind to activin A with a $K_D$ of 10 μM or higher. In some embodiments, the polypeptide does not bind to BMP9 or activin A. In some embodiments, the polypeptide binds to activin and/or myostatin and exhibits reduced (e.g., weak) binding to BMP9.

Additionally, in some embodiments, the polypeptide may bind to human BMP9 with a $K_D$ of about 200 μM or higher (e.g., a $K_D$ of about 200, 300, 400, 500, 600, 700, 800, or 900 μM or higher, e.g., a $K_D$ of about 1, 2, 3, 4, 5, 6, 7, 8, 9, 10, 20, 30, 40, or 50 nM or higher, e.g., a $K_D$ of between about 200 μM and about 50 nM). In some embodiments, the polypeptide does not substantially bind to human BMP9. In some embodiments, the polypeptide may bind to human activin A with a $K_D$ of about 800 μM or less (e.g., a $K_D$ of about 800, 700, 600, 500, 400, 300, 200, 100, 90, 80, 70, 60, 50, 40, 30, 20, 10, 9, 8, 7, 6, 5, 4, 3, 2, or 1 μM or less, e.g., a $K_D$ of between about 800 μM and about 200 μM). In some embodiments, the polypeptide may bind to human activin B with a $K_D$ of 800 μM or less (e.g., a $K_D$ of about 800, 700, 600, 500, 400, 300, 200, 100, 90, 80, 70, 60, 50, 40, 30, 20, 10, 9, 8, 7, 6, 5, 4, 3, 2, or 1 μM or less, e.g., a $K_D$ of between about 800 μM and about 200 μM) The polypeptide may also bind to growth and differentiation factor 11 (GDF-11) with a $K_D$ of approximately 5 μM or higher (e.g., a $K_D$ of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 μM or higher).

II. Fc Domains

In some embodiments, a polypeptide described herein may include an extracellular ActRIIB variant fused to an Fc domain monomer of an immunoglobulin or a fragment of an Fc domain to increase the serum half-life of the polypeptide. A polypeptide including an extracellular ActRIIB variant fused to an Fc domain monomer may form a dimer (e.g., homodimer or heterodimer) through the interaction between two Fc domain monomers, which form an Fc domain in the dimer. As conventionally known in the art, an Fc domain is the protein structure that is found at the C-terminus of an immunoglobulin. An Fc domain includes two Fc domain monomers that are dimerized by the interaction between the $CH_3$ antibody constant domains. A wild-type Fc domain forms the minimum structure that binds to an Fc receptor, e.g., FcγRI, FcγRIIa, FcγRIIb, FcγRIIIa, FcγRIIIb, FcγRIV. In some embodiments, an Fc domain may be mutated to lack effector functions, typical of a "dead" Fc domain. For example, an Fc domain may include specific amino acid substitutions that are known to minimize the interaction between the Fc domain and an Fcγ receptor. In some embodiments, an Fc domain is from an IgG1 antibody and includes amino acid substitutions L234A, L235A, and G237A. In some embodiments, an Fc domain is from an IgG1 antibody and includes amino acid substitutions D265A, K322A, and N434A. The aforementioned amino acid positions are defined according to Kabat (Sequences of Proteins of Immunological Interest, 5th Ed. Public Health Service, National Institutes of Health, Bethesda, MD. (1991)). The Kabat numbering of amino acid residues may be determined for a given antibody by alignment at regions of homology of the sequence of the antibody with a "standard" Kabat numbered sequence. Furthermore, in some embodiments, an Fc domain does not induce any immune system-related response. For example, the Fc domain in a dimer of a polypeptide including an extracellular ActRIIB variant fused to an Fc domain monomer may be modified to reduce the interaction or binding between the Fc domain and an Fcγ receptor. The sequence of an Fc domain monomer that may be fused to an extracellular ActRIIB variant is shown below (SEQ ID NO: 19):

THTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVS

NKALPVPIEKTISKAKGQPREPQVYTLPPSREEMTKNQVSLTCLVKGFYPS

DIAVEWESNGQPENNYKTTPPVLDSDGPFFLYSKLTVDKSRWQQGNVFSCS

VMHEALHNHYTQKSLSLSPGK

In some embodiments, an Fc domain is from an IgG1 antibody and includes amino acid substitutions L12A, L13A, and G15A, relative to the sequence of SEQ ID NO: 19. In some embodiments, an Fc domain is from an IgG1 antibody and includes amino acid substitutions D43A, K100A, and N212A, relative to the sequence of SEQ ID NO: 19. In some embodiments, an extracellular ActRIIB variant described herein (e.g., an extracellular ActRIIB variant having the sequence of any one of SEQ ID NOs: 1-15 (e.g., SEQ ID NOs: 2-15)) may be fused to the N- or C-terminus of an Fc domain monomer (e.g., SEQ ID NO: 19) through conventional genetic or chemical means, e.g., chemical conjugation. If desired, a linker (e.g., a spacer) can be inserted between the extracellular ActRIIB variant and the Fc domain monomer. The Fc domain monomer can be fused to the N- or C-terminus (e.g., C-terminus) of the extracellular ActRIIB variant.

In some embodiments, a polypeptide described herein may include an extracellular ActRIIB variant fused to an Fc domain. In some embodiments, the Fc domain contains one or more amino acid substitutions that reduce or inhibit Fc domain dimerization. In some embodiments, the Fc domain contains a hinge domain. The Fc domain can be of immunoglobulin antibody isotype IgG, IgE, IgM, IgA, or IgD. Additionally, the Fc domain can be an IgG subtype (e.g., IgG1, IgG2a, IgG2b, IgG3, or IgG4). The Fc domain can also be a non-naturally occurring Fc domain, e.g., a recombinant Fc domain.

Methods of engineering Fc domains that have reduced dimerization are known in the art. In some embodiments, one or more amino acids with large side-chains (e.g., tyrosine or tryptophan) may be introduced to the $CH_3$-$CH_3$ dimer interface to hinder dimer formation due to steric clash. In other embodiments, one or more amino acids with small side-chains (e.g., alanine, valine, or threonine) may be introduced to the $CH_3$-$CH_3$ dimer interface to remove favorable interactions. Methods of introducing amino acids with large or small side-chains in the $CH_3$ domain are described in, e.g., Ying et al. (*J Biol Chem.* 287:19399-19408, 2012), U.S. Patent Publication No. 2006/0074225, U.S. Pat. Nos. 8,216,805 and 5,731,168, Ridgway et al. (*Protein Eng.* 9:617-612, 1996), Atwell et al. (*J Mol Biol.* 270:26-35, 1997), and Merchant et al. (*Nat Biotechnol.* 16:677-681, 1998), all of which are incorporated herein by reference in their entireties.

In yet other embodiments, one or more amino acid residues in the $CH_3$ domain that make up the $CH_3$-$CH_3$ interface between two Fc domains are replaced with positively-charged amino acid residues (e.g., lysine, arginine, or histidine) or negatively-charged amino acid residues (e.g., aspartic acid or glutamic acid) such that the interaction becomes electrostatically unfavorable depending on the specific charged amino acids introduced. Methods of introducing charged amino acids in the $CH_3$ domain to disfavor or prevent dimer formation are described in, e.g., Ying et al. (*J Biol Chem.* 287:19399-19408, 2012), U.S. Patent Publication Nos. 2006/0074225, 2012/0244578, and 2014/0024111, all of which are incorporated herein by reference in their entireties.

In some embodiments of the invention, an Fc domain includes one or more of the following amino acid substitutions: T366W, T366Y, T394W, F405W, Y349T, Y349E, Y349V, L351T, L351H, L351N, L352K, P353S, S354D, D356K, D356R, D356S, E357K, E357R, E357Q, S364A, T366E, L368T, L368Y, L368E, K370E, K370D, K370Q, K392E, K392D, T394N, P395N, P396T, V397T, V397Q, L398T, D399K, D399R, D399N, F405T, F405H, F405R, Y407T, Y407H, Y407I, K409E, K409D, K409T, and K409I, relative to the sequence of human IgG1. In one particular embodiment, an Fc domain includes the amino acid substitution T366W, relative to the sequence of human IgG1. The sequence of wild-type Fc domain is (SEQ ID NO: 71):

MEWSWVFLFFLSVTTGVHSDKTHTCPPCPAPELLGGPSVFLFPPKPKDTLM

ISRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFF

LYSKLTVDKSRWQQGNVFSCSVMHEALHNHYTQKSLSLSPGK

III. Albumin-Binding Peptide

In some embodiments, a polypeptide described herein may include an extracellular ActRIIB variant fused to a serum protein-binding peptide. Binding to serum protein peptides can improve the pharmacokinetics of protein pharmaceuticals.

As one example, albumin-binding peptides that can be used in the methods and compositions described here are generally known in the art. In one embodiment, the albumin binding peptide includes the sequence DICLPRWGCLW (SEQ ID NO: 72).

In the present invention, albumin-binding peptides may be joined to the N- or C-terminus (e.g., C-terminus) of an extracellular ActRIIB variant described herein (e.g., an extracellular ActRIIB variant having the sequence of any one of SEQ ID NOs: 1-15 (e.g., SEQ ID NOs: 2-15)) to increase the serum half-life of the extracellular ActRIIB variant. In some embodiments, an albumin-binding peptide is joined, either directly or through a linker, to the N- or C-terminus of an extracellular ActRIIB variant.

In some embodiments, an extracellular ActRIIB variant described herein (e.g., an extracellular ActRIIB variant having the sequence of any one of SEQ ID NOs: 1-15 (e.g., SEQ ID NOs: 2-15)) may be fused to the N- or C-terminus of albumin-binding peptide (e.g., SEQ ID NO: 72) through conventional genetic or chemical means, e.g., chemical conjugation. If desired, a linker (e.g., a spacer) can be inserted between the extracellular ActRIIB variant and the albumin-binding peptide. Without being bound to a theory, it is expected that inclusion of an albumin-binding peptide in an extracellular ActRIIB variant described herein may lead to prolonged retention of the therapeutic protein through its binding to serum albumin.

IV. Fibronectin Domain

In some embodiments, a polypeptide described herein may include an extracellular ActRIIB variant fused to fibronectin domains. Binding to fibronectin domains can improve the pharmacokinetics of protein pharmaceuticals.

Fibronectin domain is a high molecular weight glycoprotein of the extracellular matrix, or a fragment thereof, that binds to, e.g., membrane-spanning receptor proteins such as integrins and extracellular matrix components such as collagens and fibrins. In some embodiments of the present invention, a fibronectin domain is joined to the N- or C-terminus (e.g., C-terminus) of an extracellular ActRIIB variant described herein (e.g., an extracellular ActRIIB variant having the sequence of any one of SEQ ID NOs: 1-15 (e.g., SEQ ID NOs: 2-15)) to increase the serum half-life of the extracellular ActRIIB variant. A fibronectin domain can be joined, either directly or through a linker, to the N- or C-terminus of an extracellular ActRIIB variant.

As one example, fibronectin domains that can be used in the methods and compositions described here are generally known in the art. In one embodiment, the fibronectin domain is a fibronectin type III domain having amino acids 610-702 of the sequence of UniProt ID NO: P02751 (SEQ ID NO: 73):

GPVEVFITETPSQPNSHPIQWNAPQPSHISKYILRWRPKNSVGRWKEATIP

GHLNSYTIKGLKPGVVYEGQLISIQQYGHQEVTRFDFTTTST

In another embodiment, the fibronectin domain is an adnectin protein.

In some embodiments, an extracellular ActRIIB variant described herein (e.g., an extracellular ActRIIB variant having the sequence of any one of SEQ ID NOs: 1-15 (e.g., SEQ ID NOs: 2-15)) may be fused to the N- or C-terminus of a fibronectin domain (e.g., SEQ ID NO: 73) through conventional genetic or chemical means, e.g., chemical conjugation. If desired, a linker (e.g., a spacer) can be inserted between the extracellular ActRIIB variant and the fibronectin domain. Without being bound to a theory, it is expected that inclusion of a fibronectin domain in an extracellular ActRIIB variant described herein may lead to prolonged retention of the therapeutic protein through its binding to integrins and extracellular matrix components such as collagens and fibrins.

V. Serum Albumin

In some embodiments, a polypeptide described herein may include an extracellular ActRIIB variant fused to serum albumin. Binding to serum albumins can improve the pharmacokinetics of protein pharmaceuticals.

Serum albumin is a globular protein that is the most abundant blood protein in mammals. Serum albumin is produced in the liver and constitutes about half of the blood serum proteins. It is monomeric and soluble in the blood. Some of the most crucial functions of serum albumin include transporting hormones, fatty acids, and other proteins in the body, buffering pH, and maintaining osmotic pressure needed for proper distribution of bodily fluids between blood vessels and body tissues. In preferred embodiments, serum albumin is human serum albumin. In some embodiments of the present invention, a human serum albumin is joined to the N- or C-terminus (e.g., C-terminus) of an extracellular ActRIIB variant described herein (e.g., an extracellular ActRIIB variant having the sequence of any one of SEQ ID NOs: 1-15 (e.g., SEQ ID NOs: 2-15)) to increase the serum half-life of the extracellular ActRIIB variant. A human serum albumin can be joined, either directly or through a linker, to the N- or C-terminus of an extracellular ActRIIB variant.

As one example, serum albumins that can be used in the methods and compositions described herein are generally known in the art. In one embodiment, the serum albumin includes the sequence of UniProt ID NO: P02768 (SEQ ID NO: 74):

MKWVTFISLLFLFSSAYSRGVFRRDAHKSEVAHRFKDLGEENFKALVLIAF

AQYLQQCPFEDHVKLVNEVTEFAKTCVADESAENCDKSLHTLFGDKLCTVA

TLRETYGEMADCCAKQEPERNECFLQHKDDNPNLPRLVRPEVDVMCTAFHD

NEETFLKKYLYEIARRHPYFYAPELLFFAKRYKAAFTECCQAADKAACLLP

-continued

```
KLDELRDEGKASSAKQRLKCASLQKFGERAFKAWAVARLSQRFPKAEFAEV

SKLVTDLTKVHTECCHGDLLECADDRADLAKYICENQDSISSKLKECCEKP

LLEKSHCIAEVENDEMPADLPSLAADFVESKDVCKNYAEAKDVFLGMFLYE

YARRHPDYSVVLLLRLAKTYETTLEKCCAAADPHECYAKVFDEFKPLVEEP

QNLIKQNCELFEQLGEYKFQNALLVRYTKKVPQVSTPTLVEVSRNLGKVGS

KCCKHPEAKRMPCAEDYLSVVLNQLCVLHEKTPVSDRVTKCCTESLVNRRP

CFSALEVDETYVPKEFNAETFTFHADICTLSEKERQIKKQTALVELVKHKP

KATKEQLKAVMDDFAAFVEKCCKADDKETCFAEEGKKLVAASQAALGL
```

In some embodiments, an extracellular ActRIIB variant described herein (e.g., an extracellular ActRIIB variant having the sequence of any one of SEQ ID NOs: 1-15 (e.g., SEQ ID NOs: 2-15)) may be fused to the N- or C-terminus of a human serum albumin (e.g., SEQ ID NO: 74) through conventional genetic or chemical means, e.g., chemical conjugation. If desired, a linker (e.g., a spacer) can be inserted between the extracellular ActRIIB variant and the human serum albumin. Without being bound to a theory, it is expected that inclusion of a human serum albumin in an extracellular ActRIIB variant described herein may lead to prolonged retention of the therapeutic protein.

VI. Linkers

A polypeptide described herein may include an extracellular ActRIIB variant (e.g., an extracellular ActRIIB variant having a sequence of any one of SEQ ID NOs: 1-15 (e.g., SEQ ID NOs: 2-15)) fused to a moiety by way of a linker. In some embodiments, the moiety increases stability of the polypeptide. Exemplary moieties include an Fc domain monomer, a wild-type Fc domain, an Fc domain with amino acid substitutions (e.g., one or more substitutions that reduce dimerization), an albumin-binding peptide, a fibronectin domain, or a human serum albumin. In the present invention, a linker between a moiety (e.g., an Fc domain monomer (e.g., the sequence of SEQ ID NO: 19), a wild-type Fc domain (e.g., SEQ ID NO: 71), an Fc domain with amino acid substitutions (e.g., one or more substitutions that reduce dimerization), an albumin-binding peptide (e.g., SEQ ID NO: 72), a fibronectin domain (e.g., SEQ ID NO: 73), or a human serum albumin (e.g., SEQ ID NO: 74)) and an extracellular ActRIIB variant (e.g., an extracellular ActRIIB variant having the sequence of any one of SEQ ID NOs: 1-15 (e.g., SEQ ID NOs: 2-15)), can be an amino acid spacer including 1-200 amino acids. Suitable peptide spacers are known in the art, and include, for example, peptide linkers containing flexible amino acid residues such as glycine, alanine, and serine. In some embodiments, a spacer can contain motifs, e.g., multiple or repeating motifs, of GA, GS, GG, GGA, GGS, GGG, GGGA (SEQ ID NO: 20), GGGS (SEQ ID NO: 21), GGGG (SEQ ID NO: 22), GGGGA (SEQ ID NO: 23), GGGGS (SEQ ID NO: 24), GGGGG (SEQ ID NO: 25), GGAG (SEQ ID NO: 26), GGSG (SEQ ID NO: 27), AGGG (SEQ ID NO: 28), or SGGG (SEQ ID NO: 29). In some embodiments, a spacer can contain 2 to 12 amino acids including motifs of GA or GS, e.g., GA, GS, GAGA (SEQ ID NO: 30), GSGS (SEQ ID NO: 31), GAGAGA (SEQ ID NO: 32), GSGSGS (SEQ ID NO: 33), GAGAGAGA (SEQ ID NO: 34), GSGSGSGS (SEQ ID NO: 35), GAGAGAGAGA (SEQ ID NO: 36), GSGSGSGSGS (SEQ ID NO: 37), GAGAGAGAGAGA (SEQ ID NO: 38), and GSGSGSGSGSGS (SEQ ID NO: 39). In some embodiments, a spacer can contain 3 to 12 amino acids including motifs of GGA or GGS, e.g., GGA, GGS, GGAGGA (SEQ ID NO: 40), GGSGGS (SEQ ID NO: 41), GGAGGAGGA (SEQ ID NO: 42), GGSGGSGGS (SEQ ID NO: 43), GGAGGAGGAGGA (SEQ ID NO: 44), and GGSGGSGGSGGS (SEQ ID NO: 45). In yet some embodiments, a spacer can contain 4 to 12 amino acids including motifs of GGAG (SEQ ID NO: 26), GGSG (SEQ ID NO: 27), e.g., GGAG (SEQ ID NO: 26), GGSG (SEQ ID NO: 27), GGAGGGAG (SEQ ID NO: 46), GGSGGGSG (SEQ ID NO: 47), GGAGGGAGGGAG (SEQ ID NO: 48), and GGSGGGSGGGSG (SEQ ID NO: 49). In some embodiments, a spacer can contain motifs of GGGGA (SEQ ID NO: 23) or GGGGS (SEQ ID NO: 24), e.g., GGGGAGGGGAGGGGA (SEQ ID NO: 50) and GGGGSGGGGSGGGGS (SEQ ID NO: 51). In some embodiments of the invention, an amino acid spacer between a moiety (e.g., an Fc domain monomer, a wild-type Fc domain, an Fc domain with amino acid substitutions (e.g., one or more substitutions that reduce dimerization), an albumin-binding peptide, a fibronectin domain, or a human serum albumin) and an extracellular ActRIIB variant (e.g., an extracellular ActRIIB variant having the sequence of any one of SEQ ID NOs: 1-15 (e.g., SEQ ID NOs: 2-15)) may be GGG, GGGA (SEQ ID NO: 20), GGGG (SEQ ID NO: 22), GGGAG (SEQ ID NO: 52), GGGAGG (SEQ ID NO: 53), or GGGAGGG (SEQ ID NO: 54).

In some embodiments, a spacer can also contain amino acids other than glycine, alanine, and serine, e.g., AAAL (SEQ ID NO: 55), AAAK (SEQ ID NO: 56), AAAR (SEQ ID NO: 57), EGKSSGSGSESKST (SEQ ID NO: 58), GSAGSAAGSGEF (SEQ ID NO: 59), AEAAAKEAAAKA (SEQ ID NO: 60), KESGSVSSEQLAQFRSLD (SEQ ID NO: 61), GENLYFQSGG (SEQ ID NO: 62), SACYCELS (SEQ ID NO: 63), RSIAT (SEQ ID NO: 64), RPACKIPNDLKQKVMNH (SEQ ID NO: 65), GGSAGGSGSGSSGGSSGASGTGTAGGTGSGSGTGSG (SEQ ID NO: 66), AAANSSIDLISVPVDSR (SEQ ID NO: 67), or GGSGGGSEGGGSEGGGSEGGGSEGGG SEGGGSGGGS (SEQ ID NO: 68). In some embodiments, a spacer can contain motifs, e.g., multiple or repeating motifs, of EAAAK (SEQ ID NO: 69). In some embodiments, a spacer can contain motifs, e.g., multiple or repeating motifs, of proline-rich sequences such as $(XP)_n$, in which X may be any amino acid (e.g., A, K, or E) and n is from 1-5, and PAPAP (SEQ ID NO: 70).

The length of the peptide spacer and the amino acids used can be adjusted depending on the two proteins involved and the degree of flexibility desired in the final protein fusion polypeptide. The length of the spacer can be adjusted to ensure proper protein folding and avoid aggregate formation.

VII. Vectors, Host Cells, and Protein Production

The polypeptides of the invention can be produced from a host cell. A host cell refers to a vehicle that includes the necessary cellular components, e.g., organelles, needed to express the polypeptides and fusion polypeptides described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, or the like). The choice of nucleic acid vectors depends in part on the host cells to be used. Generally, preferred host cells are of either eukaryotic (e.g., mammalian) or prokaryotic (e.g., bacterial) origin.

Nucleic Acid Vector Construction and Host Cells

A nucleic acid sequence encoding the amino acid sequence of a polypeptide of the invention may be prepared by a variety of methods known in the art. These methods include, but are not limited to, oligonucleotide-mediated (or site-directed) mutagenesis and PCR mutagenesis. A nucleic acid molecule encoding a polypeptide of the invention may be obtained using standard techniques, e.g., gene synthesis. Alternatively, a nucleic acid molecule encoding a wild-type extracellular ActRIIB may be mutated to include specific amino acid substitutions using standard techniques in the art, e.g., QuikChange™ mutagenesis. Nucleic acid molecules can be synthesized using a nucleotide synthesizer or PCR techniques.

A nucleic acid sequence encoding a polypeptide of the invention may be inserted into a vector capable of replicating and expressing the nucleic acid molecule in prokaryotic or eukaryotic host cells. Many vectors are available in the art and can be used for the purpose of the invention. Each vector may include various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding protein of interest, and a transcription termination sequence.

In some embodiments, mammalian cells may be used as host cells for the invention. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. In some embodiments, *E. coli* cells may also be used as host cells for the invention. Examples of *E. coli* strains include, but are not limited to, *E. coli* 294 (ATCC®31,446), *E. coli* λ 1776 (ATCC® 31,537, *E. coli* BL21 (DE3) (ATCC® BAA-1025), and *E. coli* RV308 (ATCC®31,608). Different host cells have characteristic and specific mechanisms for the posttranslational processing and modification of protein products (e.g., glycosylation). Appropriate cell lines or host systems may be chosen to ensure the correct modification and processing of the polypeptide expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) *Recombinant Gene Expression: Reviews and Protocols* (*Methods in Molecular Biology*), Humana Press; 2nd ed. 2004 and Vladimir Voynov and Justin A. Caravella (eds.) *Therapeutic Proteins: Methods and Protocols* (*Methods in Molecular Biology*) Humana Press; 2nd ed. 2012.

Protein Production, Recovery, and Purification

Host cells used to produce the polypeptides of the invention may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and $CO_2$ levels, such as 5 to 10%. The pH of the medium is generally from about 6.8 to 7.4, e.g., 7.0, depending mainly on the host organism. If an inducible promoter is used in the expression vector of the invention, protein expression is induced under conditions suitable for the activation of the promoter.

In some embodiments, depending on the expression vector and the host cells used, the expressed protein may be secreted from the host cells (e.g., mammalian host cells) into the cell culture media. Protein recovery may involve filtering the cell culture media to remove cell debris. The proteins may be further purified. A polypeptide of the invention may be purified by any method known in the art of protein purification, for example, by chromatography (e.g., ion exchange, affinity, and size-exclusion column chromatography), centrifugation, differential solubility, or by any other standard technique for the purification of proteins. For example, the protein can be isolated and purified by appropriately selecting and combining affinity columns such as Protein A column (e.g., POROS Protein A chromatography) with chromatography columns (e.g., POROS HS-50 cation exchange chromatography), filtration, ultra filtration, salting-out and dialysis procedures.

In other embodiments, host cells may be disrupted, e.g., by osmotic shock, sonication, or lysis, to recover the expressed protein. Once the cells are disrupted, cell debris may be removed by centrifugation or filtration. In some instances, a polypeptide can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from influenza hemagglutinin protein (Wilson et al., *Cell* 37:767, 1984).

Alternatively, the polypeptides of the invention can be produced by the cells of a subject (e.g., a human), e.g., in the context of gene therapy, by administrating a vector (such as a viral vector (e.g., a retroviral vector, adenoviral vector, poxviral vector (e.g., vaccinia viral vector, such as Modified Vaccinia Ankara (MVA)), adeno-associated viral vector, and alphaviral vector)) containing a nucleic acid molecule encoding the polypeptide of the invention. The vector, once inside a cell of the subject (e.g., by transformation, transfection, electroporation, calcium phosphate precipitation, direct microinjection, infection, etc.) will promote expression of the polypeptide, which is then secreted from the cell. If treatment of a disease or disorder is the desired outcome, no further action may be required. If collection of the protein is desired, blood may be collected from the subject and the protein purified from the blood by methods known in the art.

VIII. Pharmaceutical Compositions and Preparations

The invention features pharmaceutical compositions that include the polypeptides described herein (e.g., a polypeptide including an extracellular ActRIIB variant (e.g., an extracellular ActRIIB variant having the sequence of any one of SEQ ID NOs: 1-15 (e.g., SEQ ID NOs: 2-15)). In some embodiments, a pharmaceutical composition of the invention includes a polypeptide including an extracellular ActRIIB variant (e.g., an extracellular ActRIIB variant having the sequence of any one of SEQ ID NOs: 1-15 (e.g., SEQ ID NOs: 2-15)) fused to a moiety (e.g., Fc domain monomer, or a dimer thereof, a wild-type Fc domain, an Fc domain with amino acid substitutions (e.g., one or more substitutions that reduce dimerization), an albumin-binding peptide, a fibronectin domain, or a human serum albumin) as the therapeutic protein. In some embodiments, a pharmaceutical composition of the invention including a polypeptide of the invention may be used in combination with other agents (e.g., therapeutic biologics and/or small molecules) or compositions in a therapy. In addition to a therapeutically effective amount of the polypeptide, the pharmaceutical composition may include one or more pharmaceutically acceptable carriers or excipients, which can be formulated by methods known to those skilled in the art. In some embodiments, a pharmaceutical composition of the invention includes a nucleic acid molecule (DNA or RNA, e.g., mRNA) encoding a polypeptide of the invention, or a vector containing such a nucleic acid molecule.

Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. Pharmaceutical compositions of the invention can be administered parenterally in the form of an injectable formulation. Pharmaceutical compositions for injection can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Banga (ed.) *Therapeutic Peptides and Proteins: Formulation, Processing and Delivery Systems* (3rd ed.) Taylor & Francis Group, CRC Press (2015).

The pharmaceutical compositions of the invention may be prepared in microcapsules, such as hydroxylmethylcellulose or gelatin-microcapsule and poly-(methylmethacrylate) microcapsule. The pharmaceutical compositions of the invention may also be prepared in other drug delivery systems such as liposomes, albumin microspheres, microemulsions, nano-particles, and nanocapsules. Such techniques are described in Remington: The Science and Practice of Pharmacy 22$^{th}$ edition (2012). The pharmaceutical compositions to be used for in vivo administration must be sterile. This is readily accomplished by filtration through sterile filtration membranes.

The pharmaceutical compositions of the invention may also be prepared as a sustained-release formulation. Suitable examples of sustained-release preparations include semipermeable matrices of solid hydrophobic polymers containing the polypeptides of the invention. Examples of sustained release matrices include polyesters, hydrogels, polyactides, copolymers of L-glutamic acid and γ ethyl-L-glutamate, non-degradable ethylene-vinyl acetate, degradable lactic acid-glycolic acid copolymers such as LUPRON DEPOT™, and poly-D-(–)-3-hydroxybutyric acid. Some sustained-release formulations enable release of molecules over a few months, e.g., one to six months, while other formulations release pharmaceutical compositions of the invention for shorter time periods, e.g., days to weeks.

The pharmaceutical composition may be formed in a unit dose form as needed. The amount of active component, e.g., a polypeptide of the invention, included in the pharmaceutical preparations is such that a suitable dose within the designated range is provided (e.g., a dose within the range of 0.01-100 mg/kg of body weight).

The pharmaceutical composition for gene therapy can be in an acceptable diluent, or can include a slow release matrix in which the gene delivery vehicle is imbedded. If hydrodynamic injection is used as the delivery method, the pharmaceutical composition containing a nucleic acid molecule encoding a polypeptide described herein or a vector (e.g., a viral vector) containing the nucleic acid molecule is delivered rapidly in a large fluid volume intravenously. Vectors that may be used as in vivo gene delivery vehicle include, but are not limited to, retroviral vectors, adenoviral vectors, poxviral vectors (e.g., vaccinia viral vectors, such as Modified Vaccinia Ankara), adeno-associated viral vectors, and alphaviral vectors.

IX. Routes, Dosage, and Administration

Pharmaceutical compositions that include the polypeptides of the invention as the therapeutic proteins may be formulated for, e.g., intravenous administration, parenteral administration, subcutaneous administration, intramuscular administration, intra-arterial administration, intrathecal administration, or intraperitoneal administration. The pharmaceutical composition may also be formulated for, or administered via, oral, nasal, spray, aerosol, rectal, or vaginal administration. For injectable formulations, various effective pharmaceutical carriers are known in the art. See, e.g., ASHP Handbook on Injectable Drugs, Toissel, 18th ed. (2014).

In some embodiments, a pharmaceutical composition that includes a nucleic acid molecule encoding a polypeptide of the invention or a vector containing such nucleic acid molecule may be administered by way of gene delivery. Methods of gene delivery are well-known to one of skill in the art. Vectors that may be used for in vivo gene delivery and expression include, but are not limited to, retroviral vectors, adenoviral vectors, poxviral vectors (e.g., vaccinia viral vectors, such as Modified Vaccinia Ankara (MVA)), adeno-associated viral vectors, and alphaviral vectors. In some embodiments, mRNA molecules encoding polypeptides of the invention may be administered directly to a subject.

In some embodiments of the present invention, nucleic acid molecules encoding a polypeptide described herein or vectors containing such nucleic acid molecules may be administered using a hydrodynamic injection platform. In the hydrodynamic injection method, a nucleic acid molecule encoding a polypeptide described herein is put under the control of a strong promoter in an engineered plasmid (e.g., a viral plasmid). The plasmid is often delivered rapidly in a large fluid volume intravenously. Hydrodynamic injection uses controlled hydrodynamic pressure in veins to enhance cell permeability such that the elevated pressure from the rapid injection of the large fluid volume results in fluid and plasmid extravasation from the vein. The expression of the nucleic acid molecule is driven primarily by the liver. In mice, hydrodynamic injection is often performed by injection of the plasmid into the tail vein. In certain embodiments, mRNA molecules encoding a polypeptide described herein may be administered using hydrodynamic injection.

The dosage of the pharmaceutical compositions of the invention depends on factors including the route of administration, the disease to be treated, and physical characteristics, e.g., age, weight, general health, of the subject. A pharmaceutical composition of the invention may include a dosage of a polypeptide of the invention ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 0.1 to about 30 mg/kg and, in a more specific embodiment, about 0.3 to about 30 mg/kg. The dosage may be adapted by the physician in accordance with conventional factors such as the extent of the disease and different parameters of the subject.

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, and oral dosage forms (e.g., ingestible solutions, drug release capsules). Generally, therapeutic proteins are dosed at 0.1-100 mg/kg, e.g., 1-50 mg/kg. Pharmaceutical compositions that include a polypeptide of the invention may be administered to a subject in need thereof, for example, one or more times (e.g., 1-10 times or more) daily, weekly, biweekly, monthly, bimonthly, quarterly, biannually, annually, or as medically necessary. In some embodiments, pharmaceutical compositions that include a polypeptide of the invention may be administered to a subject in need thereof weekly, biweekly, monthly, bimonthly, or quarterly. Dosages may be provided in either a single or multiple dosage regimens. The timing between administrations may decrease as the medical condition improves or increase as the health of the patient declines.

X. Methods of Treatment

The invention is based on the discovery that substituting amino acids from the extracellular portion of ActRIIA into the extracellular portion ActRIIB yields ActRIIB variants with improved properties. The ActRIIB variants generated by introducing residues from ActRIIA into ActRIIB may retain the beneficial properties of ActRIIB, such as an ability to increase muscle mass and high binding affinity to activins A and B, and gain some of the beneficial properties of ActRIIA, such as reduced binding affinity to BMP9 or an ability to increase red blood cell levels. As the ActRIIB variants contain the extracellular portion of the receptor, they will be soluble and able to compete with endogenous activin receptors by binding to and sequestering ligands (e.g., activins A and B, myostatin, GDF11) without activating intracellular signaling pathways. Therefore, the extracellular ActRIIB variants described herein can be used to treat diseases or conditions in which elevated activin signaling has been implicated in pathogenesis (e.g., diseases or conditions in which increased expression of activin receptors or activin receptor ligands has been observed). For example, loss of myostatin has been shown to increase skeletal muscle mass, suggesting that myostatin inhibits skeletal muscle growth. Myostatin has also been implicated in promoting fibrosis, as loss of myostatin has been shown to reduce fibrosis, while increased myostatin or activin induces fibrosis. In addition, activin has been found to be upregulated in bone disease and is known to inhibit osteoblast activity, suggesting that increased activin levels contribute to bone disease. Activin A has also been found to be elevated in clinical and experimental pulmonary hypertension. In another example, activin receptor ligand GDF11 is overexpressed in a mouse model of hemolytic anemia and associated with defects in red blood cell production. Without wishing to be bound by theory, a therapeutic agent that binds to activin receptor ligands (e.g., GDF11, myostatin, and/or activins) and reduces their binding to or interaction with endogenous activin receptors could have therapeutic utility for treating or preventing a variety of diseases or conditions, such as muscle disease, bone disease, fibrosis, anemia, or PH (e.g., PAH, venous PH, hypoxic PH, thromboembolic PH, or miscellaneous PH).

The compositions and methods described herein can be used to treat and/or prevent (e.g., prevent the development of or treat a subject diagnosed with) medical conditions, e.g., muscle disease, bone disease, low red blood cell levels (e.g., low hemoglobin levels or low red blood cell count, e.g., anemia), fibrosis, or PH (e.g., PAH, venous PH, hypoxic PH, thromboembolic PH, or miscellaneous PH). In some embodiments, the polypeptides described herein (e.g., a polypeptide including an extracellular ActRIIB variant (e.g., an extracellular ActRIIB variant having the sequence of any one of SEQ ID NOs: 1-15 (e.g., SEQ ID NOs: 2-15), e.g., an effective amount of an ActRIIB variant) may be administered to increase muscle mass and strength in a subject in need thereof. In some embodiments, the polypeptides described herein may be administered to increase lean mass. The polypeptides described herein may increase muscle mass or lean mass compared to measurements obtained prior to treatment. In some embodiments, the subject may have or be at risk of developing a disease that results in muscle weakness or atrophy (e.g., skeletal muscle weakness or atrophy). In some embodiments, the methods described herein are directed to affecting myostatin, activin, and/or BMP9 signaling (e.g., reducing or inhibiting the binding of activin, myostatin, and/or BMP9 to their endogenous receptors) in a subject having a disease or condition involving weakness and atrophy of muscles.

In some embodiments, the polypeptides described herein (e.g., a polypeptide including an extracellular ActRIIB variant (e.g., an extracellular ActRIIB variant having the sequence of any one of SEQ ID NOs: 1-15 (e.g., SEQ ID NOs: 2-15), e.g., an effective amount of an ActRIIB variant) may be administered to increase bone mineral density, increase bone formation, increase bone strength, reduce the risk of bone fracture, or reduce bone resorption in a subject in need thereof. The polypeptides described herein may increase bone mineral density, increase bone formation, or reduce bone resorption compared to measurements obtained prior to treatment. In some embodiments, the subject may have or be at risk of developing a disease that results in bone damage (e.g., osteoporosis or osteopenia). In some embodiments, the methods described herein are directed to affecting myostatin, activin, and/or BMP9 signaling (e.g., reducing or inhibiting the binding of activin, myostatin, and/or BMP9 to their endogenous receptors) in a subject having a disease or condition involving bone damage.

In some embodiments, the polypeptides described herein (e.g., a polypeptide including an extracellular ActRIIB variant (e.g., an extracellular ActRIIB variant having the sequence of any one of SEQ ID NOs: 1-15 (e.g., SEQ ID NOs: 2-15), e.g., an effective amount of an ActRIIB variant) may be administered to increase red blood cell levels (e.g., increase hemoglobin levels, increase red blood cell count, increase hematocrit, or increase red blood cell formation or production) in a subject in need thereof. The polypeptides described herein may increase red blood cell levels (e.g., increase hemoglobin levels, red blood cell count, hematocrit, or red blood cell formation) compared to measurements obtained prior to treatment. In some embodiments, the subject may have a disease or condition associated with low red blood cell levels (e.g., anemia or blood loss). In some embodiments, the subject may have or be at risk of developing anemia or blood loss (e.g., the subject may be at risk of developing anemia due to other diseases or conditions, such as chronic kidney disease, rheumatoid arthritis, cancer, or inflammatory diseases (e.g., Crohn's disease, SLE, or ulcerative colitis), or due to medical treatments, such as chemotherapy, radiation therapy, or surgery). In some embodiments, the methods described herein are directed to affecting myostatin, activin, and/or BMP9 signaling (e.g., reducing or inhibiting the binding of activin, myostatin, and/or BMP9 to their endogenous receptors) in a subject having a disease or condition involving low red blood cell levels (e.g., anemia or blood loss).

In some embodiments, the polypeptides described herein (e.g., a polypeptide including an extracellular ActRIIB variant (e.g., an extracellular ActRIIB variant having the sequence of any one of SEQ ID NOs: 1-15 (e.g., SEQ ID NOs: 2-15), e.g., an effective amount of an ActRIIB variant) may be administered to prevent or reduce fibrosis in a subject in need thereof. In some embodiments, the polypeptides described herein may be administered to slow or stop the progression of fibrosis, to reduce the risk of developing fibrosis, or to reduce (e.g., reduce the frequency or severity of) one or more symptom of fibrosis. The polypeptides described herein may reduce fibrosis or slow the progression of fibrosis by at least compared to the progression of fibrosis prior to treatment or compared to the progression of fibrosis in untreated subjects. In some embodiments, the subject may have or be at risk of developing fibrosis (e.g., the subject may have a disease or condition associated with fibrosis, such as a wound, hepatitis B or C, fatty liver disease, kidney disease (e.g., chronic kidney disease), heart disease, or atherosclerosis, or may be undergoing treatment associated with the development of fibrosis, such as chemotherapy, radiation, or surgery). In some embodiments, the polypeptides described herein prevent or delay the development of fibrosis in a subject at risk of developing fibrosis (e.g., a subject being treated with chemotherapy, radiation, or surgery, or a subject having a disease or condition associated with fibrosis, such as a wound, hepatitis B or C, fatty liver disease, kidney disease (e.g., chronic kidney disease), heart disease, or atherosclerosis). In some embodiments, the methods described herein are directed to affecting myostatin, activin, and/or BMP9 signaling (e.g., reducing or inhibiting the binding of activin, myostatin, and/or BMP9 to their endogenous receptors) in a subject having fibrosis or a disease or condition associated with fibrosis.

In some embodiments, the polypeptides described herein (e.g., a polypeptide including an extracellular ActRIIB variant (e.g., an extracellular ActRIIB variant having the sequence of any one of SEQ ID NOs: 1-15 (e.g., SEQ ID NOs: 2-15), e.g., an effective amount of an ActRIIB variant) may be administered to treat PH, reduce PH (e.g., reduce the severity or frequency of one or more symptoms of PH, such as shortness of breath (dyspnea), fatigue, swelling (e.g., edema) of the legs, feet, belly (ascites), or neck, chest pain or pressure, racing pulse or heart palpitations, bluish color to lips or skin (cyanosis), dizziness, or fainting), prevent (e.g., prevent the development of) PH, reduce the risk of developing PH, or slow or stop the progression of PH in a subject in need thereof. The polypeptides described herein may reduce the symptoms of PH (e.g., reduce the severity or frequency of one or more symptoms, such as shortness of breath (dyspnea), fatigue, swelling (e.g., edema) of the legs, feet, belly (ascites), or neck, chest pain or pressure, racing pulse or heart palpitations, bluish color to lips or skin (cyanosis), dizziness, or fainting) or slow the progression of PH (e.g., PAH, venous PH, hypoxic PH, thromboembolic PH, or miscellaneous PH) compared to the symptoms or progression observed prior to treatment or compared to symptoms or progression of PH in untreated subjects. In some embodiments, the subject may have or be at risk of developing PH (e.g., the subject may have idiopathic PAH; the subject may have a disease or condition associated with PAH (e.g., a disease or condition that leads to increased risk of developing PAH), such as HIV infection, schistosomiasis, portal hypertension, pulmonary veno-occlusive disease, pulmonary capillary hemangiomatosis, cirrhosis of the liver, congenital heart abnormalities, connective tissue/autoimmune disorders (e.g., scleroderma or lupus), or drug use or abuse (e.g., methamphetamine or cocaine use); the subject may have a family history of PH (e.g., heritable PAH); the subject may have a disease or condition associated with venous PH (e.g., a disease or condition that leads to increased risk of developing venous PH), such as left ventricular systolic dysfunction, left ventricular diastolic dysfunction, valvular heart disease, congenital cardiomyopathy, or congenital/acquired pulmonary venous stenosis; the subject may have a disease or condition associated with hypoxic PH (e.g., a disease or condition that leads to increased risk of developing hypoxic PH), such as chronic obstructive pulmonary disease (e.g., emphysema), interstitial lung disease, sleep-disordered breathing (e.g., sleep apnea), lung disease (e.g., pulmonary fibrosis), an alveolar hypoventilation disorder, chronic exposure to high altitude, or a developmental abnormality; the subject may have a disease or condition associated with thromboembolic PH (e.g., a disease or condition that leads to increased risk of developing thromboembolic PH), such as chronic thromboembolic pulmonary hypertension, or other pulmonary artery obstructions (e.g., pulmonary emboli, angiosarcoma, arteritis, congenital pulmonary artery stenosis, or parasitic infection); or the subject may have a disease or condition associated with miscellaneous PH (e.g., a disease or condition that leads to increased risk of developing miscellaneous PH), such as hematologic diseases (e.g., chronic hemolytic anemia, sickle cell disease), systemic diseases (e.g., sarcoidosis, pulmonary Langerhans cell histiocytosis, lymphangioleiomyomatosis, neurofibromatosis, or vasculitis), metabolic disorders (e.g., glycogen storage disease, Gaucher disease, or thyroid diseases), pulmonary tumoral thrombotic microangiopathy, fibrosing mediastinitis, chronic kidney failure, or segmental pulmonary hypertension (pulmonary hypertension restricted to one or more lobes of the lungs)). In some embodiments, the polypeptides described herein prevent or delay the development of PH in a subject at risk of developing PH (e.g., a subject with a family history of PH (e.g., heritable PAH), or a subject having a disease or condition that leads to increased risk of developing PAH (e.g., HIV infection, schistosomiasis, cirrhosis of the liver, congenital heart abnormalities, connective tissue/autoimmune disorders (e.g., scleroderma or lupus), or drug use or abuse (e.g., methamphetamine or cocaine use), venous PH (e.g., left ventricular systolic dysfunction, left ventricular diastolic dysfunction, valvular heart disease, congenital cardiomyopathy, or congenital/acquired pulmonary venous stenosis), hypoxic PH (e.g., chronic obstructive pulmonary disease (e.g., emphysema), interstitial lung disease, sleep-disordered breathing (e.g., sleep apnea), lung disease (e.g., pulmonary fibrosis), an alveolar hypoventilation disorder, chronic exposure to high altitude, or a developmental abnormality), thromboembolic PH (e.g., chronic thromboembolic pulmonary hypertension, or other pulmonary artery obstructions (e.g., pulmonary emboli, angiosarcoma, arteritis, congenital pulmonary artery stenosis, or parasitic infection)), or miscellaneous PH (e.g., a hematologic disease (e.g., chronic hemolytic anemia, sickle cell disease), a systemic disease (e.g., sarcoidosis, pulmonary Langerhans cell histiocytosis, lymphangioleiomyomatosis, neurofibromatosis, or vasculitis), a metabolic disorder (e.g., glycogen storage disease, Gaucher disease, or thyroid diseases), pulmonary tumoral thrombotic microangiopathy, fibrosing mediastinitis, chronic kidney failure, or segmental pulmonary hypertension). In some embodiments, the methods described herein are directed to affecting myostatin, activin, and/or BMP9 signaling (e.g., reducing or inhibiting the binding of activin, myostatin, and/or BMP9 to their receptors) in a subject having PH or a disease or condition associated with PH. In some embodiments, the PH is PAH, venous PH, hypoxic PH, thromboembolic PH, or miscellaneous PH.

In some embodiments, a polypeptide including an extracellular ActRIIB variant described herein reduces or inhibits the binding of myostatin, activin, and/or BMP9 to their endogenous receptors, e.g., ActRIIA, ActRIIB, and BMPRII (e.g., ActRIIB). The polypeptides described herein may reduce the binding of myostatin, activin, and/or BMP9 to their endogenous receptors compared to the binding of myostatin, activin, and/or BMP9 to their endogenous receptors in the absence of the polypeptides of the invention. In some embodiments, affecting myostatin, activin, and/or BMP9 signaling (e.g., reducing or inhibiting the binding of myostatin, activin, and/or BMP9 to their endogenous receptors, e.g., ActRIIA, ActRIIB, and BMPRII (e.g., ActRIIB)) results in an increase in the subject's muscle mass, an increase in the subject's bone mineral density or bone formation, a decrease in the subject's bone resorption, an increase in the subject's red blood cell levels (e.g., hemoglobin levels, hematocrit, or red blood cell count, e.g., promotes or increases red blood cell formation or production), a reduction in the subject's fibrosis or risk of developing fibrosis, a delay in the development of fibrosis, a reduction (e.g., slowing or inhibiting) in the progression of fibrosis, a reduction in the symptoms of PH (e.g., a reduction in shortness of breath (dyspnea), fatigue, swelling (e.g., edema) of the legs, feet, belly (ascites), or neck, chest pain or pressure, racing pulse or heart palpitations, bluish color to lips or skin (cyanosis), dizziness, or fainting), a reduction in the risk of developing PH, a delay in the development of PH, and/or a reduction (e.g., slowing or inhibiting) in the progression of PH. The PH can be PAH, venous PH, hypoxic PH, thromboembolic PH, or miscellaneous PH.

In some embodiments, the polypeptides described herein (e.g., a polypeptide including an extracellular ActRIIB variant (e.g., an extracellular ActRIIB variant having the sequence of any one of SEQ ID NOs: 1-15 (e.g., SEQ ID NOs: 2-15), e.g., an effective amount of an ActRIIB variant) may be administered to a subject to increase muscle mass or strength, to increase bone mineral density, to increase bone formation, to increase bone strength, to reduce the risk of bone fracture, to decrease bone resorption, to increase red blood cell levels (e.g., to increase hemoglobin levels, increase hematocrit, increase red blood cell count, or induce or increase red blood cell formation), to prevent or reduce fibrosis (e.g., to reduce fibrosis, to prevent or delay the development of fibrosis, or to slow or stop the progression of fibrosis), to prevent or treat PH (e.g., to reduce symptoms of PH, to prevent or delay the development of PH, or to slow or stop the progression of PH, such as PAH, venous PH, hypoxic PH, thromboembolic PH, or miscellaneous PH), or to affect myostatin, activin, and/or BMP9 signaling in the subject. The extracellular ActRIIB variants (e.g., an extracellular ActRIIB variant having the sequence of any one of SEQ ID NOs: 1-15 (e.g., SEQ ID NOs: 2-15), e.g., an effective amount of an ActRIIB variant) may increase muscle mass or strength, increase bone mineral density, increase bone formation, increase bone strength, reduce the risk of bone fracture, decrease bone resorption, increase red blood cell levels, prevent or reduce fibrosis, or prevent or treat PH compared to measurements obtained prior to treatment or compared to measurements obtained from untreated subjects having the same disease or condition. In some embodiments, the methods described herein do not cause any vascular complications in the subject, such as increased vascular permeability or leakage. In some embodiments of the methods described herein, the subject has or is at risk of developing a disease or condition involving weakness and atrophy of muscles (e.g., Duchenne muscular dystrophy (DMD), facioscapulohumeral muscular dystrophy (FSHD), inclusion body myositis (IBM), amyotrophic lateral sclerosis (ALS), sarcopenia, or cancer cachexia). In some embodiments of the methods described herein, the subject has or is at risk of developing a disease or condition involving bone damage (e.g., primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss). In some embodiments of the methods described herein, the subject has or is at risk of developing a disease or condition involving low red blood cell levels (e.g., anemia or blood loss, such as anemia associated with cancer (e.g., multiple myeloma, leukemia, breast cancer, lung cancer, colon cancer), cancer treatment (e.g., chemotherapy or radiation therapy), myelodysplastic syndrome, chronic or acute renal disease or failure (e.g., chronic kidney disease), inflammatory or auto-immune disease (e.g., rheumatoid arthritis, inflammatory bowel disease, such as Crohn's disease or ulcerative colitis, SLE), or surgery). In some embodiments of the methods described herein, the subject has or is at risk of developing a disease or condition involving fibrosis (e.g., chemotherapeutic drug-induced fibrosis, radiation-induced fibrosis, pulmonary fibrosis, hepatic fibrosis (e.g., cirrhosis), renal fibrosis (e.g., fibrosis related to chronic kidney disease), corneal fibrosis, heart fibrosis, osteoarticular fibrosis, tissue fibrosis, a tumor stroma, a desmoplastic tumor, a surgical adhesion, a hypertrophic scar, a keloid, or fibrosis is associated with wounds, burns, hepatitis B or C infection, fatty liver disease, Schistosoma infection, kidney disease, heart disease, macular degeneration, retinal or vitreal retinopathy, systemic or local scleroderma, atherosclerosis, or restenosis). In some embodiments of the methods described herein, the subject has or is at risk of developing a disease or condition involving PH (e.g., PAH, venous PH, hypoxic PH, thromboembolic PH, or miscellaneous PH, e.g., idiopathic PAH; heritable PAH; PAH associated with or caused by HIV infection, schistosomiasis, portal hypertension, pulmonary veno-occlusive disease, pulmonary capillary hemangiomatosis, cirrhosis of the liver, congenital heart abnormalities, connective tissue/autoimmune disorders (e.g., scleroderma or lupus), or drug use or abuse (e.g., methamphetamine or cocaine use); venous PH associated with or caused by left ventricular systolic dysfunction, left ventricular diastolic dysfunction, valvular heart disease, congenital cardiomyopathy, or congenital/acquired pulmonary venous stenosis; hypoxic PH associated with or caused by chronic obstructive pulmonary disease (e.g., emphysema), interstitial lung disease, sleep-disordered breathing (e.g., sleep apnea), lung disease (e.g., pulmonary fibrosis), an alveolar hypoventilation disorder, chronic exposure to high altitude, or a developmental abnormality; thromboembolic PH associated with or caused by chronic thromboembolic pulmonary hypertension, or other pulmonary artery obstructions (e.g., pulmonary emboli, angiosarcoma, arteritis, congenital pulmonary artery stenosis, or parasitic infection); miscellaneous PH associated with or caused by a hematologic disease (e.g., chronic hemolytic anemia, sickle cell disease), a systemic disease (e.g., sarcoidosis, pulmonary Langerhans cell histiocytosis, lymphangioleiomyomatosis, neurofibromatosis, or vasculitis), a metabolic disorder (e.g., glycogen storage disease, Gaucher disease, or thyroid diseases), pulmonary tumoral thrombotic microangiopathy, fibrosing mediastinitis, chronic kidney failure, or segmental pulmonary hypertension).

The invention also includes methods of treating a subject having or at risk of developing Duchenne muscular dystrophy (DMD), facioscapulohumeral muscular dystrophy (FSHD), inclusion body myositis (IBM), amyotrophic lateral sclerosis (ALS), sarcopenia, cancer cachexia, primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, immobility-related bone loss, anemia, blood loss, fibrosis, or PH (e.g., PAH, venous PH, hypoxic PH, thromboembolic PH, or miscellaneous PH) by administering to the subject an effective amount of a polypeptide described herein (e.g., a polypeptide including an extracellular ActRIIB variant (e.g., an extracellular ActRIIB variant having the sequence of any one of SEQ ID NOs: 1-15 (e.g., SEQ ID NOs: 2-15)).

In any of the methods described herein, a subject having or at risk of developing bone disease (e.g., bone damage) has or is at risk of developing a disease or condition including primary osteoporosis, secondary osteoporosis, osteopenia, osteopetrosis, bone fracture, bone cancer or cancer metastasis-related bone loss, Paget's disease, renal osteodystrophy, treatment-related bone loss, diet-related bone loss, bone loss associated with the treatment of obesity, low gravity-related bone loss, or immobility-related bone loss. In some embodiments, the primary osteoporosis is age-related or hormone-related osteoporosis (e.g., related to a decline in estrogen). In some embodiments, the secondary osteoporosis is immobilization-induced or glucocorticoid-induced osteoporosis. In some embodiments, the bone cancer is multiple myeloma or the cancer metastasis-related bone loss is caused by multiple myeloma. In some embodiments, the treatment-related bone loss occurs due to treatment with FGF-21 or GLP-1, due to treatment with an FGF-21 or GLP-1 containing therapeutic, due to treatment of Type-2 diabetes and/or obesity, or due to cancer therapy (e.g., chemotherapy or radiation). In some embodiments, the diet-related bone loss is rickets (e.g., vitamin D deficiency). In some embodiments, the low-gravity related bone loss is lack of load-related bone loss. In some embodiments, the methods described herein increase bone mineral density (e.g., increase bone mass), e.g., increase bone mineral density compared to measurements obtained prior to treatment or compared to bone mineral density typically observed in untreated subjects. In some embodiments, the methods described herein reduce bone resorption (e.g., reduce bone catabolic activity), e.g., reduce bone resorption compared to measurements obtained prior to treatment or compared to bone resorption typically observed in untreated subjects. In some embodiments, the methods described herein increase bone formation (e.g., increase bone anabolic activity or increase osteogenesis), e.g., increase bone formation compared to measurements obtained prior to treatment or compared to bone formation typically observed in untreated subjects. In some embodiments, the methods described herein increase osteoblast activity or osteoblastogenesis, e.g., increase osteoblast activity or osteoblastogenesis compared to measurements obtained prior to treatment or compared to osteoblast activity or osteoblastogenesis typically observed in untreated subjects. In some embodiments, the methods described herein decrease osteoclast activity or osteoclastogenesis, e.g., decrease osteoclast activity or osteoclastogenesis compared to measurements obtained prior to treatment or compared to osteoclast activity or osteoclastogenesis typically observed in untreated subjects. In some embodiments, the bone is cortical or trabecular bone.

The invention also includes methods of treating a subject having or at risk of developing anemia or blood loss by administering to the subject an effective amount of a polypeptide described herein (e.g., a polypeptide including an extracellular ActRIIB variant (e.g., an extracellular ActRIIB variant having the sequence of any one of SEQ ID NOs: 1-15 (e.g., SEQ ID NOs: 2-15)). In any of the methods described herein, a subject having or at risk of developing low red blood cell levels (e.g., low hemoglobin levels, low hematocrit, or low red blood cell counts) has or is at risk of developing anemia or blood loss. In some embodiments, the anemia is associated with nutritional deficits (e.g., vitamin deficiency), bone marrow defects (e.g., paroxysmal nocturnal hemoglobinuria), adverse reaction to medication (e.g., anti-retroviral HIV drugs), myelodysplastic syndrome, bone marrow transplantation, cancer (e.g., solid tumors, such as breast cancer, lung cancer, colon cancer; tumors of the lymphatic system, such as chronic lymphocyte leukemia, non-Hodgkin's lymphoma, Hodgkin's lymphoma; or tumors of the hematopoietic system, such as leukemia or multiple myeloma), cancer treatment (e.g., radiation or chemotherapy, e.g., chemotherapy with platinum-containing agents), inflammatory or autoimmune disease (e.g., rheumatoid arthritis, other inflammatory arthritides, systemic lupus erythematosus (SLE), acute or chronic skin diseases (e.g. psoriasis), or inflammatory bowel disease (e.g., Crohn's disease or ulcerative colitis), cystitis, gastritis), acute or chronic renal disease or failure (e.g., chronic kidney disease) including idiopathic or congenital conditions, acute or chronic liver disease, acute or chronic bleeding, infection (e.g., malaria, osteomyelitis), splenomegaly, porphyria, vasculitis, hemolysis, urinary tract infection, hemoglobinopathy (e.g., sickle cell disease), thalassemia, Churg-Strauss syndrome, Felty syndrome, graft versus host disease, hematopoietic stem cell transplantation, osteomyelofibrosis, pancytopenia, pure red-cell aplasia, purpura Schoenlein-Henoch, Shwachman syndrome (e.g., Shwachman-Diamond syndrome), drug use or abuse (e.g., alcohol abuse), or contraindication to transfusion (e.g., patients of advanced age, patients with allo- or auto-antibodies, pediatric patients, patients with cardiopulmonary disease, patients who object to transfusion for religious reasons (e.g., some Jehovah's Witnesses)). In some embodiments, the anemia is aplastic anemia, iron deficiency anemia, vitamin deficiency anemia, anemia of chronic disease, anemia associated with bone marrow disease, hemolytic anemia, sickle cell anemia, microcytic anemia, hypochromic anemia, sideroblastic anemia, Diamond Blackfan anemia, Fanconi's anemia, or refractory anemia with excess of blasts. The compositions and methods described herein can also be used to treat subjects that do not respond well to erythropoietin (EPO) or that are susceptible to adverse effects of EPO (e.g., hypertension, headaches, vascular thrombosis, influenza-like syndrome, obstruction of shunts, and myocardial infarction). In some embodiments, the blood loss is due to surgery, trauma, a wound, an ulcer, urinary tract bleeding, digestive tract bleeding, frequent blood donation, or heavy menstrual bleeding (e.g., menorrhagia). In some embodiments, the methods described herein increase red blood cell levels (e.g., hemoglobin levels, hematocrit, or red blood cell counts) compared to measurements obtained prior to treatment. In some embodiments, the methods described herein increase or induce red blood cell formation compared to measurements obtained prior to treatment. In some embodiments, the compositions and methods described herein reduce the need of a subject for a blood transfusion (e.g., the subject no longer needs blood transfusions, or the subject needs less frequent blood transfusion than before treatment with the compositions and methods described herein). Subjects with normal red blood cell levels can also be treated using the methods and compositions described herein to increase red blood cell levels so that blood can be drawn and stored for later use in transfusions.

The invention also includes methods of treating a subject having or at risk of developing fibrosis by administering to the subject an effective amount of a polypeptide described herein (e.g., a polypeptide including an extracellular ActRIIB variant (e.g., an extracellular ActRIIB variant having the sequence of any one of SEQ ID NOs: 1-15 (e.g., SEQ ID NOs: 2-15)). In any of the methods described herein, the subject has or is at risk of developing fibrosis. In some embodiments, the fibrosis is fibrosis is chemotherapeutic drug-induced fibrosis, radiation-induced fibrosis, pulmonary fibrosis (e.g., cystic fibrosis, idiopathic fibrosis, or fibrosis related to tuberculosis, pneumonia, or coal dust), hepatic fibrosis (e.g., cirrhosis, biliary atresia), renal fibrosis (e.g., fibrosis related to chronic kidney disease), corneal fibrosis, heart fibrosis (e.g., endomyocardial fibrosis, or fibrosis related to myocardial infarction), bone marrow fibrosis, mediastinal fibrosis, retropertinoneal fibrosis, arthrofibrosis, osteoarticular fibrosis, tissue fibrosis (e.g., fibrosis affecting muscle tissue, skin epidermis, skin dermis, tendon, cartilage, pancreatic tissue, uterine tissue, neural tissue, testis, ovary, adrenal gland, artery, vein, colon, small intestine, large intestine, biliary tract, or gut), a tumor stroma, a desmoplastic tumor, a surgical adhesion, a hypertrophic scar, or a keloid. In some embodiments, the fibrosis is associated with wounds, burns, hepatitis B or C infection, fatty liver disease, Schistosoma infection, kidney disease (e.g., chronic kidney disease), heart disease, macular degeneration, retinal or vitreal retinopathy, Crohn's disease, systemic or local scleroderma, atherosclerosis, or restenosis. In some embodiments, the subject is at risk of developing fibrosis related to cancer treatment (chemotherapy or radiation), disease or infection (e.g., tuberculosis, pneumonia, myocardial infarction, hepatitis B or C infection, fatty liver disease, Schistosoma infection, kidney disease (e.g., chronic kidney disease), heart disease, macular degeneration, retinal or vitreal retinopathy, Crohn's disease, systemic or local scleroderma, atherosclerosis, restenosis), surgery, a wound, or a burn. In some embodiments, the methods described herein reduce fibrosis compared to measurements obtained prior to treatment or compared to fibrosis in untreated subjects. In some embodiments, the methods described herein prevent the development of fibrosis or reduce the risk of developing fibrosis (e.g., reduce the risk of developing fibrosis compared to the development of fibrosis in untreated subjects). In some embodiments, the methods described herein slow or stop the progression of fibrosis (e.g., slow the progression of fibrosis compared to progression prior to treatment or compared to progression without treatment or in an untreated subject). In some embodiments, the methods described herein reduce the frequency or severity of one or more symptom of fibrosis. In some embodiments, the methods described herein improve organ or tissue function (e.g., the function of the organ or tissue having fibrosis) compared to organ or tissue function prior to treatment. Tissue and organ function can be assessed using any standard clinical test commonly used to evaluate tissue and organ function.

The invention also includes methods of treating a subject having or at risk of developing PH (e.g., PAH, venous PH, hypoxic PH, thromboembolic PH, or miscellaneous PH) by administering to the subject an effective amount of a polypeptide described herein (e.g., a polypeptide including an extracellular ActRIIB variant (e.g., an extracellular ActRIIB variant having the sequence of any one of SEQ ID NOs: 1-15 (e.g., SEQ ID NOs: 2-15)). In any of the methods described herein, the subject may have or be at risk of developing PH (e.g., PAH, venous PH, hypoxic PH, thromboembolic PH, or miscellaneous PH). In some embodiments, the PH is PAH. In some embodiments, the PAH is idiopathic PAH. In some embodiments, the PAH is heritable PAH. In some embodiments, the PAH is PAH related to (e.g., caused by or associated with) HIV infection, schistosomiasis, portal hypertension, pulmonary veno-occlusive disease, pulmonary capillary hemangiomatosis, cirrhosis of the liver, congenital heart abnormalities, connective tissue/autoimmune disorders (e.g., scleroderma or lupus), or drug use or abuse (e.g., methamphetamine or cocaine use). In some embodiments, the PH is venous PH. In some embodiments, the venous PH is venous PH related to (e.g., caused by or associated with) left ventricular systolic dysfunction, left ventricular diastolic dysfunction, valvular heart disease, congenital cardiomyopathy, or congenital/acquired pulmonary venous stenosis. In some embodiments, the PH is hypoxic PH. In some embodiments, the hypoxic PH is hypoxic PH related to (e.g., caused by or associated with) chronic obstructive pulmonary disease (e.g., emphysema), interstitial lung disease, sleep-disordered breathing (e.g., sleep apnea), lung disease (e.g., pulmonary fibrosis), alveolar hypoventilation disorders, chronic exposure to high altitude, or developmental abnormalities. In some embodiments, the PH is thromboembolic PH. In some embodiments, the thromboembolic PH is thromboembolic PH related to (e.g., caused by or associated with) chronic thromboembolic pulmonary hypertension, or other pulmonary artery obstructions (e.g., pulmonary emboli, angiosarcoma, arteritis, congenital pulmonary artery stenosis, or parasitic infection). In some embodiments, the PH is miscellaneous PH. In some embodiments, the miscellaneous PH is miscellaneous PH related to (e.g., caused by or associated with) a hematologic disease (e.g., chronic hemolytic anemia, sickle cell disease), a systemic disease (e.g., sarcoidosis, pulmonary Langerhans cell histiocytosis, lymphangioleiomyomatosis, neurofibromatosis, or vasculitis), a metabolic disorder (e.g., glycogen storage disease, Gaucher disease, or thyroid diseases), pulmonary tumoral thrombotic microangiopathy, fibrosing mediastinitis, chronic kidney failure, or segmental pulmonary hypertension). In some embodiments, the methods described herein reduce the symptoms (e.g., reduce the severity or frequency of symptoms, such as shortness of breath (dyspnea), fatigue, swelling (e.g., edema) of the legs, feet, belly (ascites), or neck, chest pain or pressure, racing pulse or heart palpitations, bluish color to lips or skin (cyanosis), dizziness, or fainting) of PH compared to the frequency or severity of symptoms prior to treatment. In some embodiments, the methods described herein prevent the development of PH or reduce the risk of developing PH (e.g., reduce the risk of developing PH (e.g., PAH, venous PH, hypoxic PH, thromboembolic PH, or miscellaneous PH) compared to the development of PH in untreated subjects). In some embodiments, the methods described herein slow or stop the progression of PH (e.g., slow the progression of PH (e.g., PAH, venous PH, hypoxic PH, thromboembolic PH, or miscellaneous PH) compared to progression prior to treatment or compared to progression without treatment or in an untreated subject). In some embodiments, the methods described herein reduce pulmonary vascular remodeling or vascular remodeling in the heart of a subject (e.g., the initiation or progression of vascular remodeling in the heart or lungs) compared to vascular remodeling prior to treatment or compared to vascular remodeling in an untreated subject. In some embodiments, the methods described herein reduce right ventricular hypertrophy (e.g., reduce right ventricular hypertrophy or the progression of right ventricular hypertrophy) compared to right ventricular hypertrophy prior to treatment or compared to right ventricular hypertrophy in an untreated subject. Symptoms of PH can be evaluated before and after treatment using standard clinical tests. Commonly used tests for evaluating PH include electrocardiograms, pulmonary function tests, echocardiograms, right heart catheterization, computed tomography scan, measurement of pulmonary vascular resistance, and the 6 minute walk test. In some embodiments, the methods described herein reduce pulmonary vascular resistance (e.g., result in a reduction in pulmonary vascular resistance compared to pulmonary vascular resistance prior to treatment). In some embodiments, the methods described herein improve performance in the 6 minute walk test compared to performance in the 6 minute walk test prior to treatment.

In any of the methods described herein, a dimer (e.g., homodimer or heterodimer) formed by the interaction of two Fc domain monomers that are each fused to a polypeptide including an extracellular ActRIIB variant (e.g., an extracellular ActRIIB variant having the sequence of any one of SEQ ID NOs: 1-15 (e.g., SEQ ID NOs: 2-15)) may be used as the therapeutic protein. In any of the methods described herein, a polypeptide including an extracellular ActRIIB variant (e.g., an extracellular ActRIIB variant having the sequence of any one of SEQ ID NOs: 1-15 (e.g., SEQ ID NOs: 2-15)) fused to a moiety (e.g., a wild-type Fc domain, an Fc domain with amino acid substitutions (e.g., one more substitutions that reduce dimerization), an albumin-binding peptide, a fibronectin domain, or a serum albumin) may be used as the therapeutic protein. Nucleic acids encoding the polypeptides described herein, or vectors containing said nucleic acids can also be administered according to any of the methods described herein. In any of the methods described herein, the polypeptide, nucleic acid, or vector can be administered as part of a pharmaceutical composition.

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Figure 1:
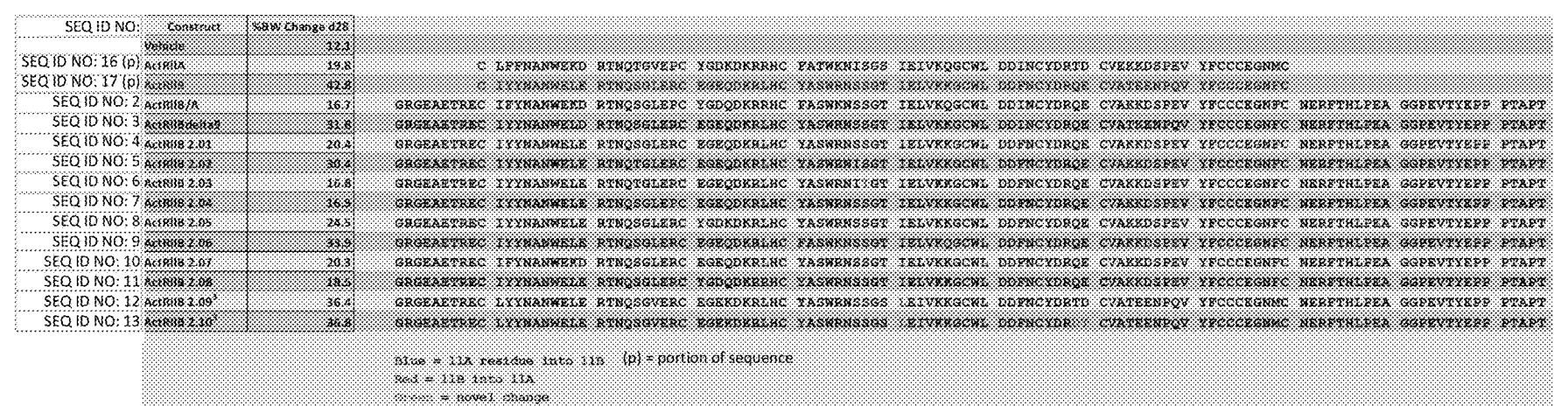
Figure 3B:
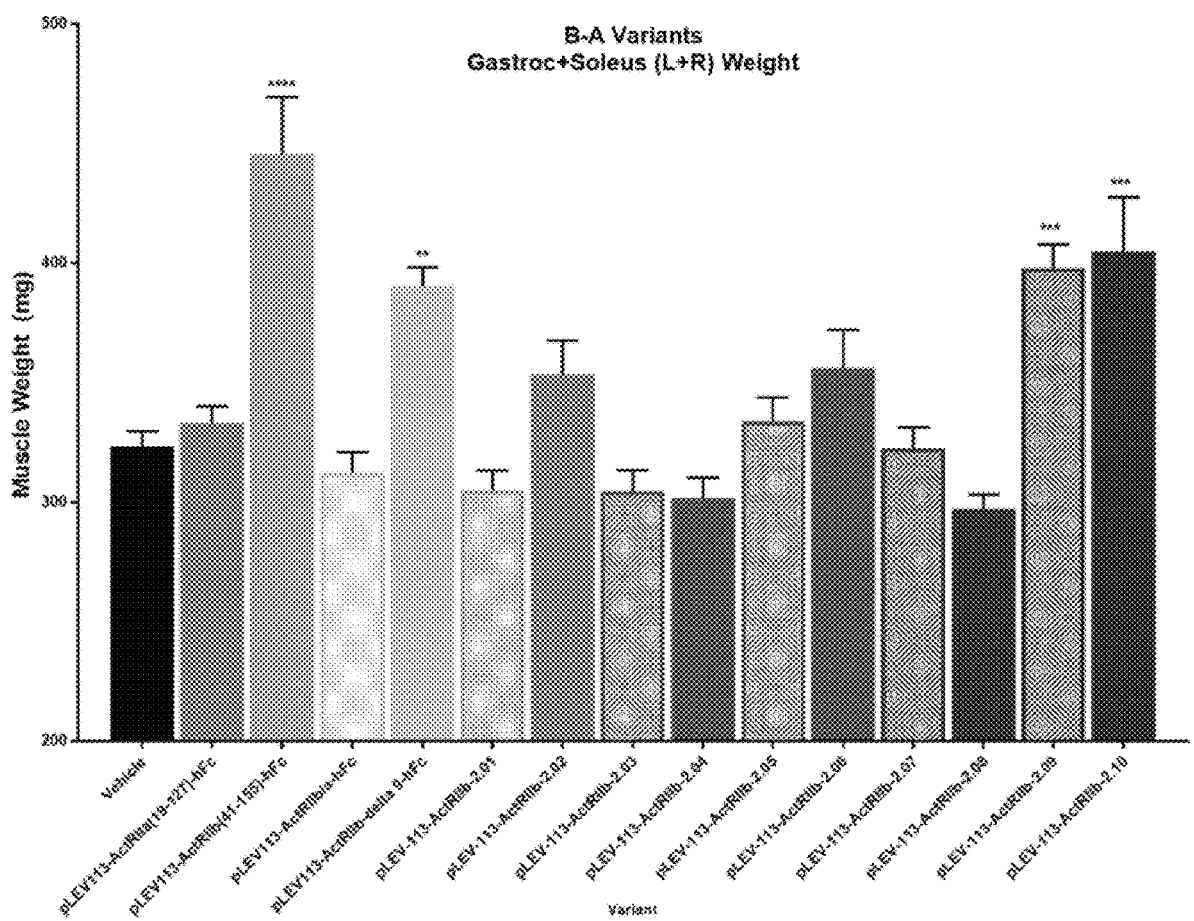

Example 1—Effect of Extracellular ActRIIB Variants on Body Weight and Muscle Weight C57Bl/6 mice received a single hydrodynamic injection of a plasmid construct encoding one of the following fourteen polypeptides or vehicle control (n=10/group, see sequences provided in FIG. 1):
(1) Vehicle,
(2) extracellular ActRIIA (SEQ ID NO: 16) fused to the N-terminus of hFc through a GGG linker;
(3) extracellular ActRIIB (SEQ ID NO: 17) fused to the N-terminus of hFc through a GGG linker;
(4) extracellular ActRIIB variant ActRIIB/A (SEQ ID NO: 2) fused to the N-terminus of hFc through a GGG linker;
(5) extracellular ActRIIB variant ActRIIBA9 (SEQ ID NO: 3) fused to the N-terminus of hFc through a GGG linker;
(6) extracellular ActRIIB variant ActRIIB 2.01 (SEQ ID NO: 4) fused to the N-terminus of hFc through a GGG linker;
(7) extracellular ActRIIB variant ActRIIB 2.02 (SEQ ID NO: 5) fused to the N-terminus of hFc through a GGG linker;
(8) extracellular ActRIIB variant ActRIIB 2.03 (SEQ ID NO: 6) fused to the N-terminus of hFc through a GGG linker;
(9) extracellular ActRIIB variant ActRIIB 2.04 (SEQ ID NO: 7) fused to the N-terminus of hFc through a GGG linker;
(10) extracellular ActRIIB variant ActRIIB 2.05 (SEQ ID NO: 8) fused to the N-terminus of hFc through a GGG linker;
(11) extracellular ActRIIB variant ActRIIB 2.06 (SEQ ID NO: 9) fused to the N-terminus of hFc through a GGG linker;
(12) extracellular ActRIIB variant ActRIIB 2.07 (SEQ ID NO: 10) fused to the N-terminus of hFc through a GGG linker;
(13) extracellular ActRIIB variant ActRIIB 2.08 (SEQ ID NO: 11) fused to the N-terminus of hFc through a GGG linker;
(14) extracellular ActRIIB variant ActRIIB 2.09 (SEQ ID NO: 12) fused to the N-terminus of hFc through a GGG linker; and
(15) extracellular ActRIIB variant ActRIIB 2.10 (SEQ ID NO: 13) fused to the N-terminus of hFc through a GGG linker.
100 µg of plasmid construct was delivered in a volume of 10% body weight over 5-8 seconds. The high volume and short period of injection provided the pressure needed to introduce the plasmid into the liver cells where the plasmid is expressed, specifically the proteins of interest were expressed under a strong and ubiquitous promoter (pLEV113). The protein of interest is secreted under the endogenous machinery of the liver cells and circulates freely. Mice were weighted twice weekly for 28 days and measurements were recorded as a percent of body weight change from baseline measurements (FIG. 1, FIG. 2). Muscles were also weighed at the end of the study and measurements were recorded in milligrams (FIGS. 3A and 3B).

Example 2—Evaluation of ActRIIB Variants Binding Affinity by Surface Plasmon Resonance (SPR)

The GE Biacore 3000 was used to measure the kinetics of the interactions between the ActRIIB-Fc variants and the ligands Activin A, Activin B, growth differentiation factor 11 (GDF11), and BMP-9. ActRIIA, ActRIIB, ActRIIB 2.06, ActRIIB 2.11 and ActRIIB 2.12 were recombinant proteins. All other ActRIIB-Fc variants were expressed by transient expression in HEK293 cells and purified from the conditioned media using Protein-A Sepharose chromatography. Flow cells 1-4 were immobilized with anti-human/anti-mouse capture antibodies from GE using the amine coupling kit. The ActRII-Fc proteins were then captured on the chip in flow cells 2-4, with flow cell 1 being left empty as a reference cell to measure and subtract any nonspecific binding. HBS-EP+buffer from GE Healthcare™ was used as a running buffer. Each ligand was run in a duplicate concentration series at 40 μl/min to avoid mass transport effects. All data was collected on a CM-5 chip except for GDF-11, which used CM-4. The data was analyzed using Scrubber2 by BioLogic™ Software to calculate the $K_D$ of each interaction (Table 3).

TABLE 3

Comparison of ActRIIB variant binding affinity ($K_D$) to various ligands

| | Construct | | | |
|---|---|---|---|---|
| | Activin A ($K_D$) | Activin B ($K_D$) | GDF-11 ($K_D$) | BMP-9 ($K_D$) |
| | | Vehicle | | |
| | N/A | N/A | N/A | N/A |
| ActRIIA (SEQ ID NO: 16) | 1 nM | 370 pM | 81 pM | 25 nM |
| ActRIIB (SEQ ID NO: 17) | 63 pM | 23 pM | 120 pM | 280 pM |
| ActRIIB/A variant (SEQ ID NO: 2) | Not detected | Not detected | Not detected | 88 nM |
| ActRIIBΔ9 variant (SEQ ID NO: 3) | 390 nM | 400 nM | 530 nM | 28 nM |
| ActRIIB 2.01 variant (SEQ ID NO: 4) | Not detected | Not detected | Not detected | Not detected |
| ActRIIB 2.02 variant (SEQ ID NO: 5) | Not detected | Not detected | Not detected | Not detected |
| ActRIIB 2.03 variant (SEQ ID NO: 6) | Not detected | Not detected | Not detected | Not detected |
| ActRIIB 2.04 variant (SEQ ID NO: 7) | Not detected | Not detected | Not detected | Not detected |
| ActRIIB 2.05 variant (SEQ ID NO: 8) | Not detected | Not detected | Not detected | Not detected |
| ActRIIB 2.06 variant (SEQ ID NO: 9) | 53 pM | 100 pM | 27 pM | 300 pM |
| ActRIIB 2.07 variant (SEQ ID NO: 10) | Not detected | Not detected | Not detected | Not detected |
| ActRIIB 2.08 variant (SEQ ID NO: 11) | Not detected | Not detected | Not detected | Not detected |
| ActRIIB 2.09 variant (SEQ ID NO: 12) | 100 pM | 160 pM | Ka 2e6 | 440 pM |
| ActRIIB 2.10 variant (SEQ ID NO: 13) | 450 pM | 280 pM | Ka 1.5e6 | 1.7 nM |
| ActRIIB 2.11 variant (SEQ ID NO: 14) | 780 pM | 370 pM | 240 pM | 2.7 nM |
| ActRIIB 2.12 variant (SEQ ID NO: 15) | 140 pM | 160 pM | 130 pM | 31 nM |

Example 3—Effect of Extracellular ActRIIB Variants on Bone Mineral Density

Adult male C57/BL6 mice receive either a sham-(SHAM) or castration-surgery (ORX). Both surgery groups are allowed to recover for 14 days post-surgery. All animals are housed in conventional cages with free access to food (regular chow) and water. SHAM and ORX animals are then assigned to either a vehicle-treated group (VEH) or ActRII variant-treated group and receive bi-weekly systemic intra-peritoneal administration of vehicle or ActRII variant (10 mg/kg) for 71 d. Body weights are measured twice per week at the time of treatment. Body composition is analyzed at study day 0 then at days 14, 28, 47, and 71 after treatment initiation using the MiniSpec LF50 NMR Analyzer. At study termination date, tissues of interest (muscles, fat depots, and tibias) are surgically removed, weighed, and properly stored for further analysis. At this time, the ORX animals are also examined to confirm complete removal of testes. Cortical morphometry and trabecular structure of the various bones are also evaluated after the experiment termination using micro-computed tomography.

Example 4—Effect of Extracellular ActRIIB Variants on Renal Fibrosis

The effect of extracellular ActRIIB variants on renal fibrosis is determined using a unilateral ureteral obstruction (UUO) mouse model of renal fibrosis. The UUO model involves complete ligation of the left ureter while keeping the right kidney function intact. Briefly, UUO is performed on mice under anesthesia, whereby the left ureter is accessed via flank incision, and two ligatures are placed on the proximal one-third of the ureter using silk thread at 5 mm apart. Sham surgeries are performed in a similar fashion without placing any ligatures on the ureter. In this model, severe fibrosis develops in the kidney within 14 days following UUO, assessed by measuring kidney collagen by directly measuring the amount of hydroxyproline in the sample. Fourteen days following UUO, dry kidney weight decreases as a result of parenchymal damage. Sham or UUO surgeries are performed on 16-week old male C57BL/6 mice, and the UUO surgery mice are divided into two groups. Each UUO group receives a subcutaneous injection of either an ActRIIB variant (10 mg/kg) or vehicle (dosed body weight volume), which does not bind to any known mouse protein, starting a day before the surgeries, and on 1, 3, 6, 8, 10, and 13 days after the surgery. Sham surgery mice receive vehicle (sterile PBS) during this time using the same schedule as the UUO groups. All the mice are sacrificed on day 14 following surgery. The kidney weights are measured, and the kidneys are flash-frozen using liquid nitrogen, and kept at −80° C. until the collagen content is measured by measuring the amount of hydroxyproline to assess fibrosis.

Example 5≤Effect of Extracellular ActRIIB Variants on Red Blood Cells

Ten male and ten female rats per group receive two SC doses (Days 1 and 15) of vehicle, or 6, 20 or 60 mg/kg of an ActRIIB variant. Hematology parameters are measured on Day 29. Studies are also conducted to evaluate the time course and the dose response for induction of RBC, hemoglobin, and hematocrit. In the first study, the time course of erythropoiesis is investigated in male and female rats that receive subcutaneous (SC) doses of an ActRIIB variant (10 mg/kg) on Days 1 and 8. Hematology parameters are evaluated prior to dosing and on Days 3, 8, 15, 29, and 44. In the second study, the hematologic dose response is investigated in male and female rats that receive SC doses of vehicle, or 0.4, 2, 10 or 30 mg/kg of an ActRIIB variant on Days 1 and 15. Hematology parameters are evaluated prior to dosing and on Days 13 and 28.

Example 6—Effect of Extracellular ActRIIB Variants on PAH

In one experiment, PAH is induced in male rats using a single subcutaneous injection of monocrotaline (MCT, 40 mg/kg). To determine whether treatment with ActRIIB variants can prevent the development of PAH, rats are randomized into vehicle or ActRIIB variant treatment groups 24 hours after PAH induction, and treated twice per week with an ActRIIB variant (5 or 15 mg/kg) or vehicle for 21 days. Ventricular function and right ventricular (RV) remodeling are examined by electrocardiogram at day 14 by anesthetizing rats with 1.5% isoflurane and using a small animal high-frequency ultrasound probe to detect pulmonary flow acceleration, right ventricular function and hypertrophy, and left ventricular function while the animal is held in a supine position. Doppler across the mitral and tricuspid valves is used to determine if treatment with the ActRIIB variant induces any obvious regurgitation or lesions. On day 21, rats are anesthetized with pentobarbital, intubated through the trachea, and mechanically ventilated using a rodent ventilator. Hemodynamics are assessed using a fluid-filled catheter through the RV apex. Rats are perfused with PBS followed by 1% formaldehyde. To measure RV hypertrophy (RVH), the heart is removed and the RV free wall dissected from the left ventricle plus septum (LV+S) and weighted separately. Degree of RVH is determined from the ratio RV/(LV+S).

In a second experiment, PAH is induced in male rats using a single subcutaneous injection of monocrotaline (MCT, 40 mg/kg). To determine whether treatment with ActRIIB variants can slow or reduce the progression of PAH, rats are injected again with MCT on day 18 and randomized into vehicle or ActRIIB variant treatment groups. Rats are injected three times per week with an ActRIIB variant (15 mg/kg) or vehicle. Hemodynamics and RVH are examined on day 35 as described above.

Example 7—Evaluation of ActRIIB Variants Using a Gene Luciferase Reporter Assay

C2C12-BRE-Luciferase and HEK293-SBE-Luciferase cells were plated on 96 well plates in DMEM supplemented with 2% FBS and placed in an incubator for no less than three hours to acclimate to the plate surface. For each ActRIIB/A-Fc variant or positive control (ActRIIA-Fc and ActRIIB-Fc), a dilution series was made in 2% DMEM and incubated with GDF-11, Activin A, Activin B, and BMP-9 for 30 minutes at 37° C. ActRIIA, ActRIIB, ActRIIB 2.06, ActRIIB 2.11 and ActRIIB 2.12 were recombinant proteins. All others were conditioned media from transiently transfected cells. Media in the plates was aspirated and the ActRIIB/A/ligand mixtures were added to the plates as media replacement. Remaining wells were used for replicates of positive controls and background. The plates were incubated overnight, and then read using Promega Steady Glo and the Molecular Devices Spectramax M5e. The cell based assays demonstrate the ability of the variants to inhibit signaling at the endogenous cell surface receptors. The variants, with the exception of ActRIIB/A and ActRIIB 2.11, have comparable inhibition of Activin A, Activin B, and GDF-11, but diminished BMP9 inhibition compared to ActRIIB-Fc, as shown in Table 4.

TABLE 4

Results from luciferase reporter assay

| Construct | Activin A | Activin B | GDF-11 | BMP-9 |
|---|---|---|---|---|
| ActRIIA (SEQ ID NO: 16) | 390 ng/mL | 210 ng/mL | 390 ng/mL | 100 µg/mL |
| ActRIIB (SEQ ID NO: 17) | 65 ng/mL | 240 ng/mL | 140 ng/mL | 82 ng/mL |
| ActRIIB/A variant (SEQ ID NO: 2) | >1 µg/mL | >1 µg/mL | >1 µg/mL | 83 µg/mL |
| ActRIIBΔ9 variant (SEQ ID NO: 3) | 480 ng/mL | 400 ng/mL | 230 ng/mL | 13 µg/mL |
| ActRIIB 2.06 variant (SEQ ID NO: 9) | 49 ng/mL | 150 ng/mL | 110 ng/mL | 52 µg/mL |
| ActRIIB 2.09 variant (SEQ ID NO: 12) | 58 ng/mL | 400 ng/mL | 300 ng/mL | 2.6 µg/mL |
| ActRIIB 2.10 variant (SEQ ID NO: 13) | 64 ng/mL | 200 ng/mL | 170 ng/mL | 9.2 µg/mL |
| ActRIIB 2.11 variant (SEQ ID NO: 14) | >1 µg/mL | >1 µg/mL | 980 ng/mL | >100 µg/mL |
| ActRIIB 2.12 variant (SEQ ID NO: 15) | 270 ng/mL | 160 ng/mL | 15 ng/mL | >100 µg/mL |

Example 8—Effect of ActRIIB Variants on Body Weight and Red Blood Cell Mass

Figure 4:
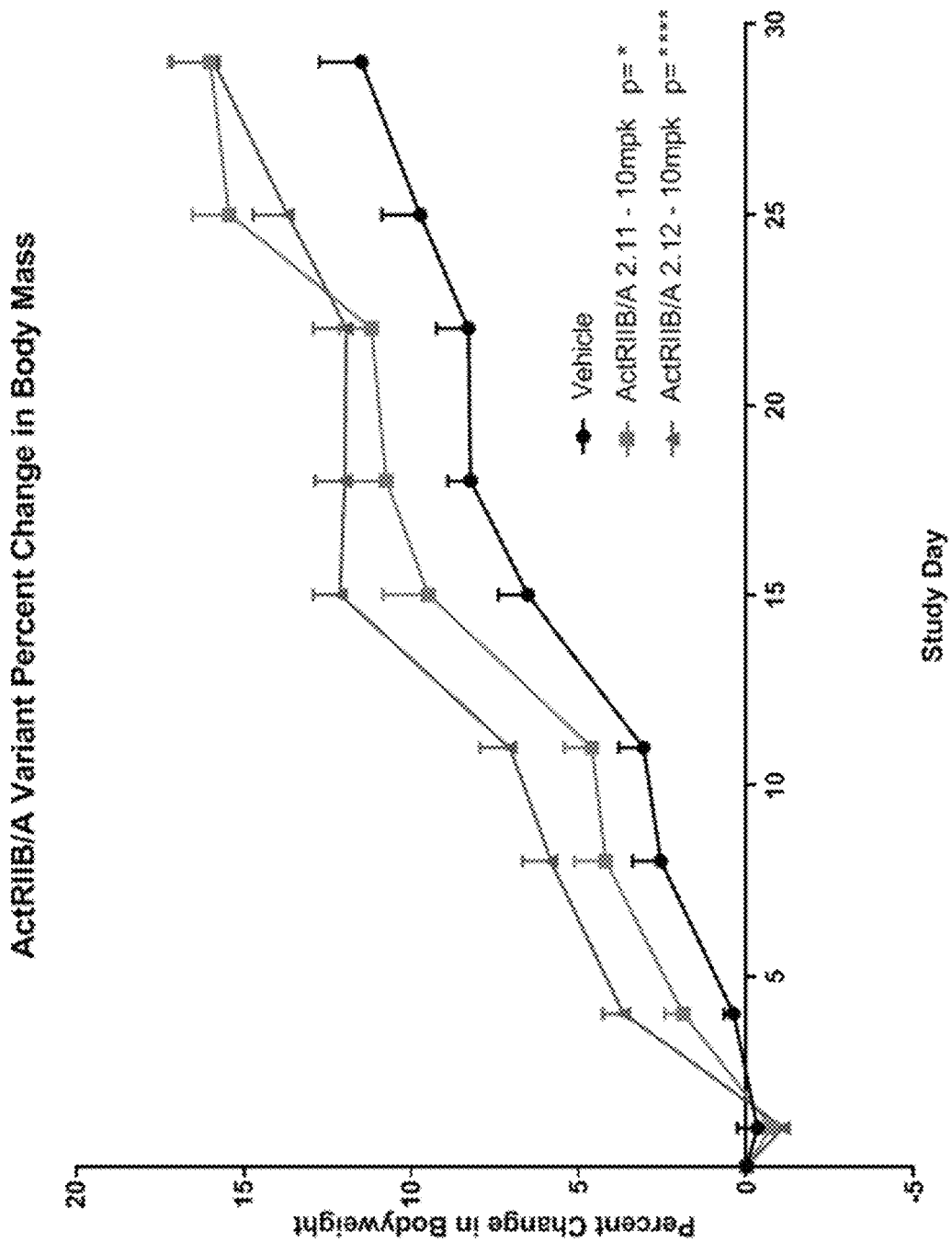
FIG. 4 is a graph depicting the effects of extracellular ActRIIB variants ActRIIB 2.11-Fc and ActRIIB 2.12-Fc on percent body weight over the course of 28 days.
Figure 5A:
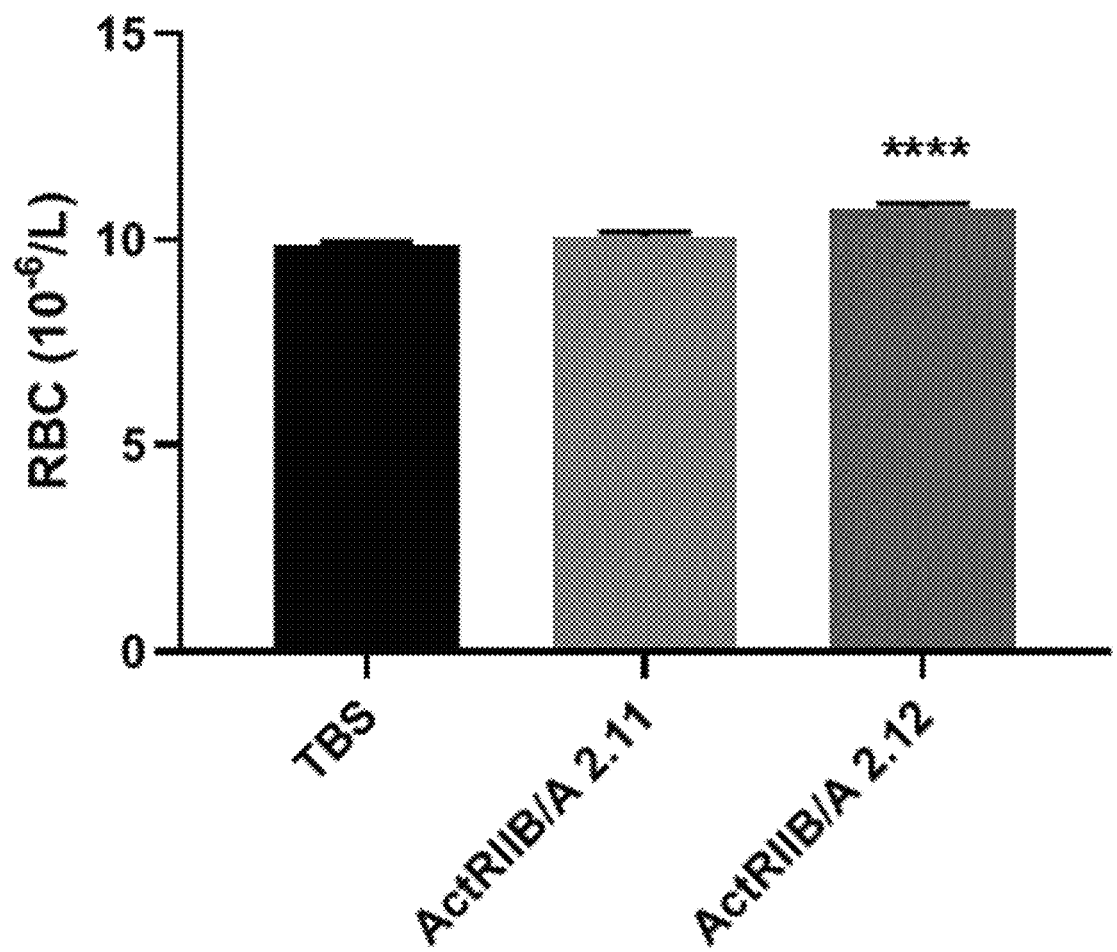
Figure 5B:
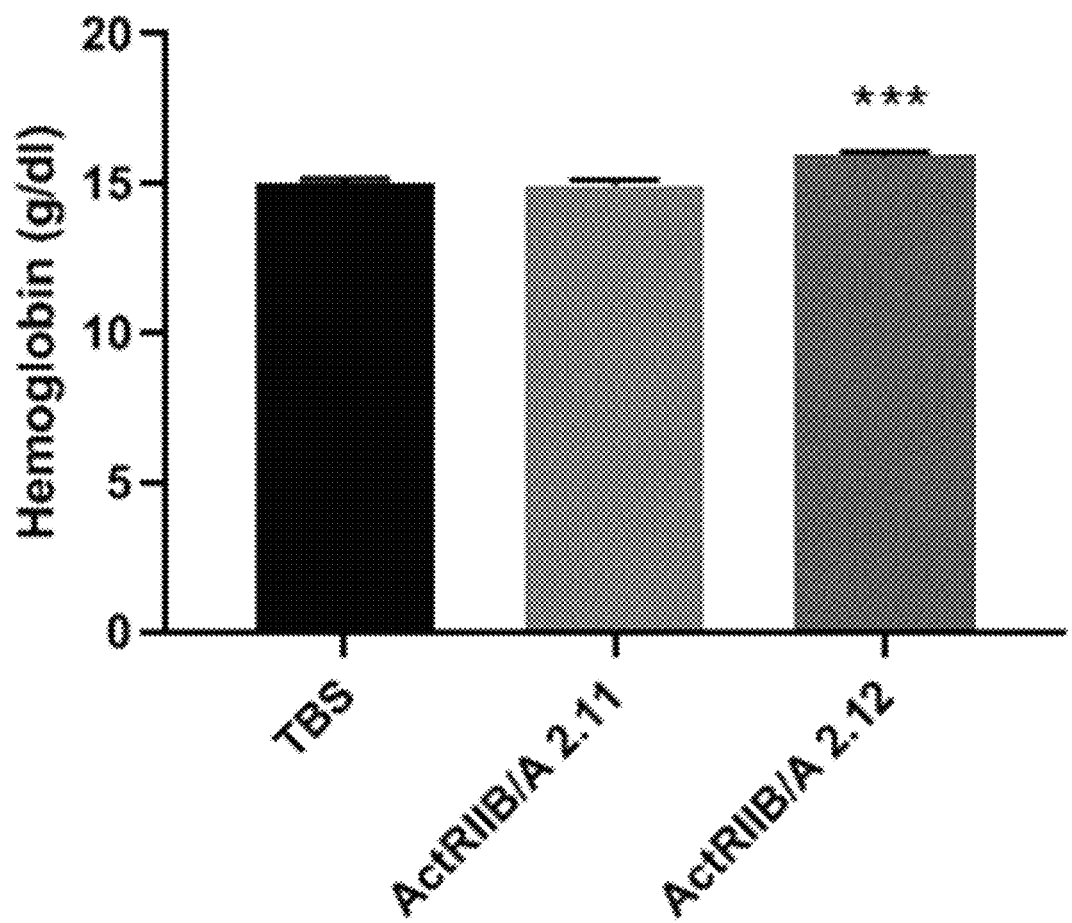
Figure 6A:
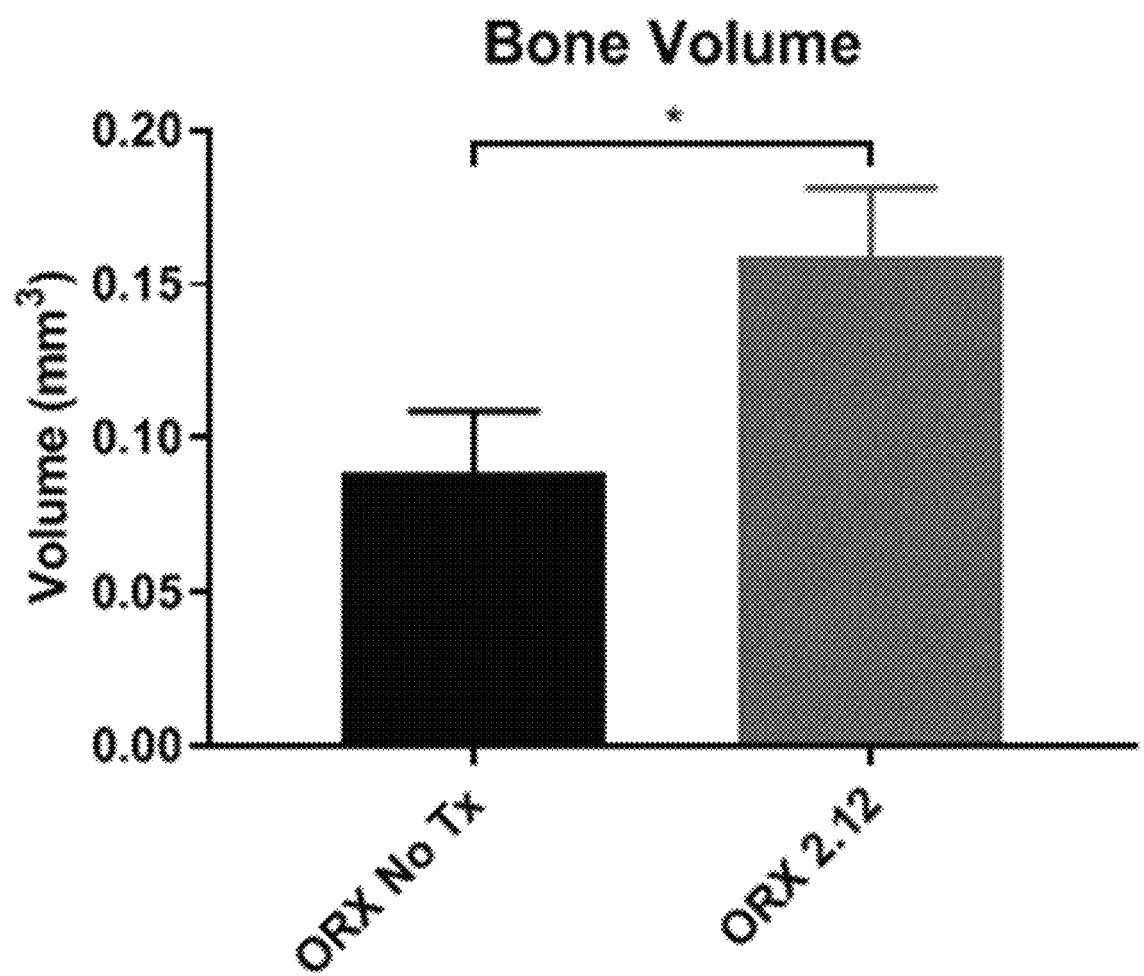
FIGS. 6A-6D are a series of graphs depicting the effects of ActRIIB variant ActRIIB 2.12-Fc on trabecular bone in a mouse model of osteoporosis.
Figure 6B:
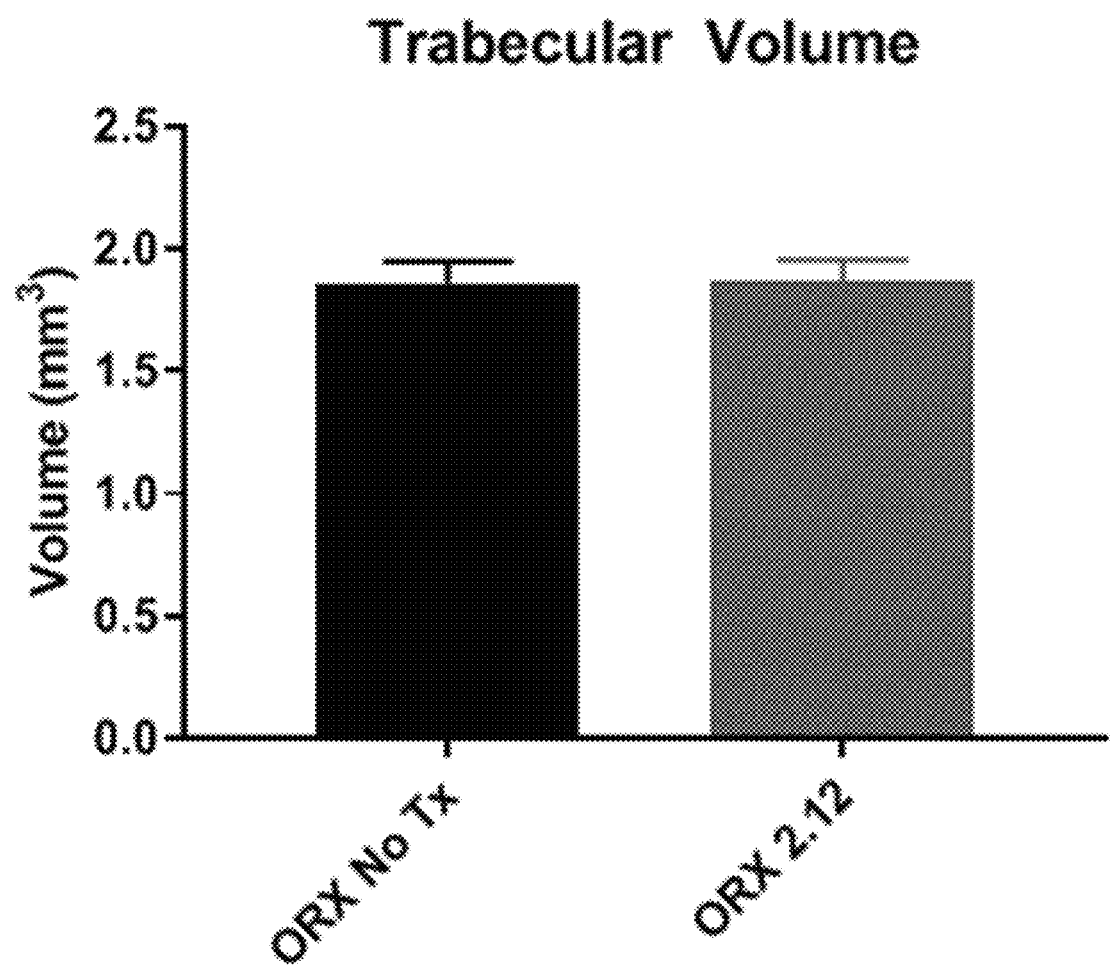
Figure 6C:
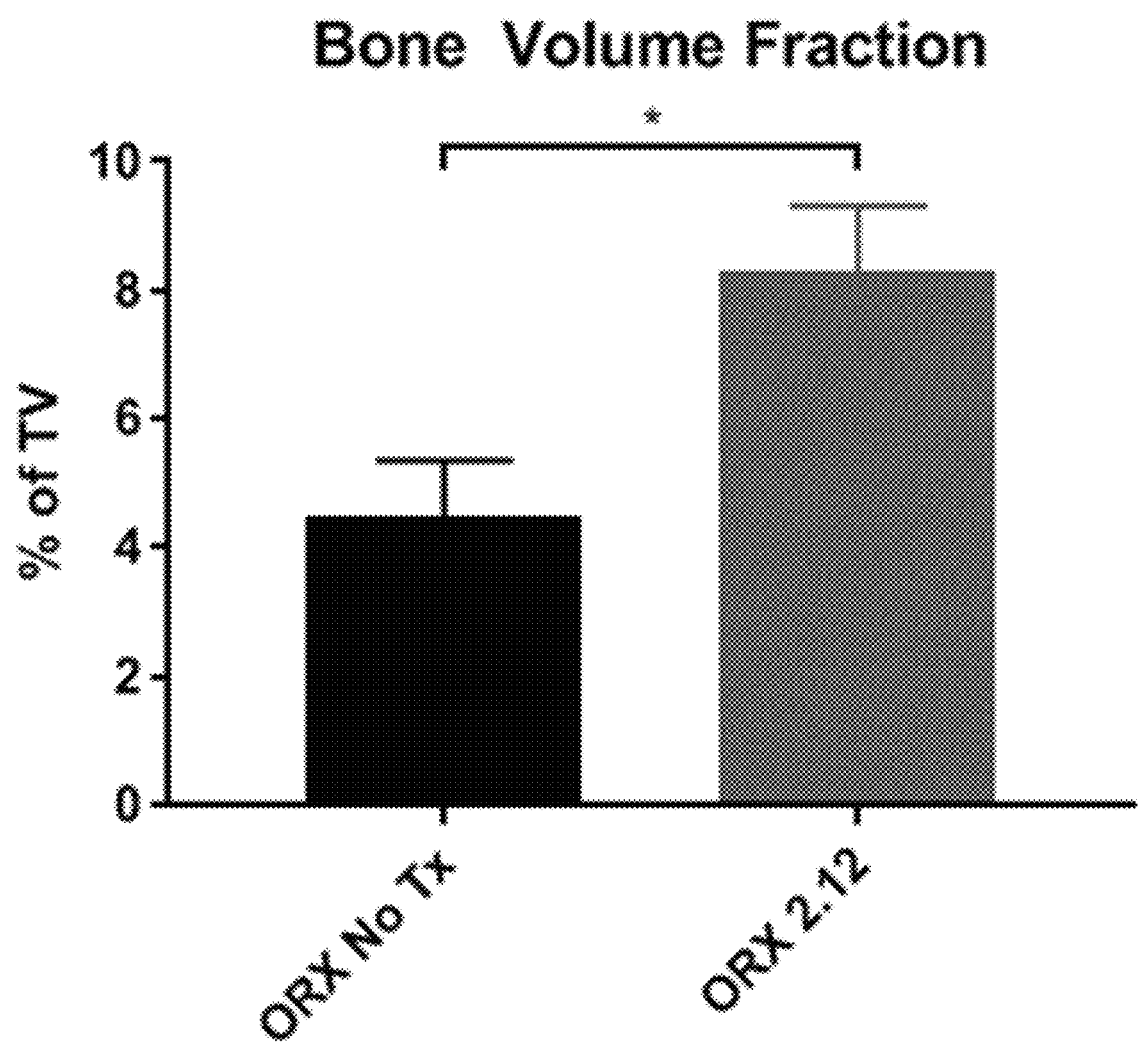
Figure 6D:
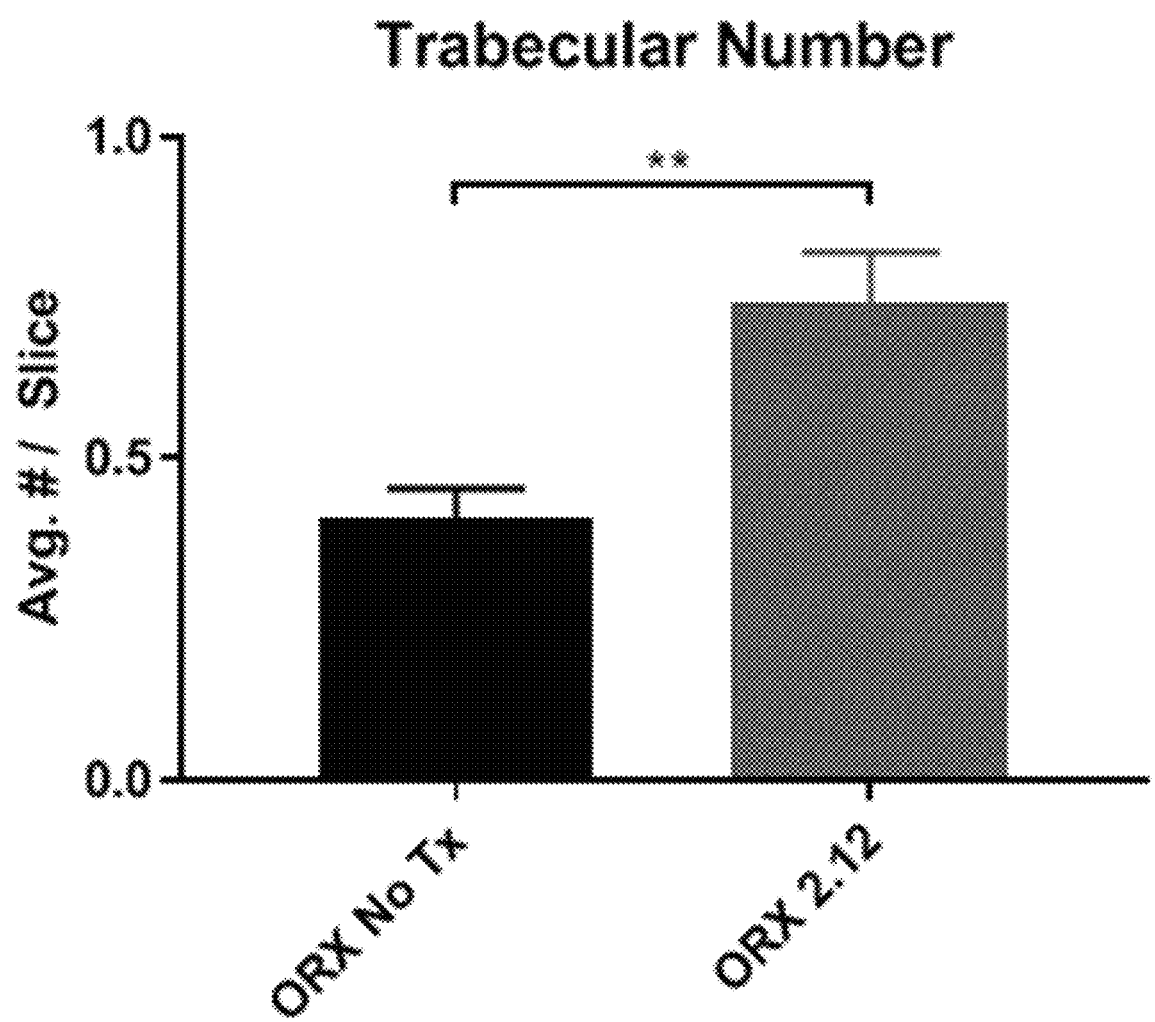

Eight-week old, male C57BL/6 mice were distributed into three groups (n=10/ group). Groups were dosed with 5 ml/kg of either vehicle (Tris-Buffered Saline, pH 7.4) or ActRIIB 2.11 (SEQ ID NO: 14)-Fc or ActRIIB 2.12 (SEQ ID NO: 15)-Fc (20 mg/kg). Treatments were administered intraperitoneally (IP) twice a week for four weeks (eight doses), and the study was terminated on study day 28. Body weights were recorded on dosing days throughout the study. Additionally, red cell mass parameters were evaluated hematologically at study termination. As shown in FIG. 4, both ActRIIB 2.11-Fc and ActRIIB 2.12-Fc increased body weight in wild-type mice (*=p<0.05; **=p<0.01). ActRIIB 2.12-Fc also increased parameters of red cell mass (*=p<0.001; ****=p<0.0001), including red blood cell count, hemoglobin levels, and hematocrit (FIGS. 5A-5C).

Example 9—Effect of an ActRIIB Variant in a Mouse Model of Osteoporosis

C57BL/6 mice received orchiectomy (ORX) or sham surgery at nine weeks of age. Following a six-week recovery period, during which time the ORX mice developed an osteoporotic phenotype, ORX mice received intraperitoneal injections twice weekly of either vehicle or ActRIIB 2.12 (SEQ ID NO: 15)-Fc (10 mg/kg). Micro-CT (Perkin Elmer Quantum Fx) imaging was conducted at 11 weeks after dosing initiation. ASBMR bone morphometry parameters of each dataset were calculated with AnalyzePro software (AnalyzeDirect, Overland Park KS) using the Bone Morphometry Analysis Add-on. A 50-slice region of CT volume immediately distal to the proximal tibial growth plate was selected to assess changes in trabecular bone parameters. As shown in FIGS. 6A-6D, Treatment with ActRIIB 2.12-Fc increased bone volume, increased bone volume fraction, and increased trabecular number associated with orchiectomy (*=p<0.05; **=p<0.01). These data indicate that treatment of osteoporotic mice with ActRIIB 2.12-Fc increases trabecular bone mass as a result of increased bone formation.

Figure 7A:
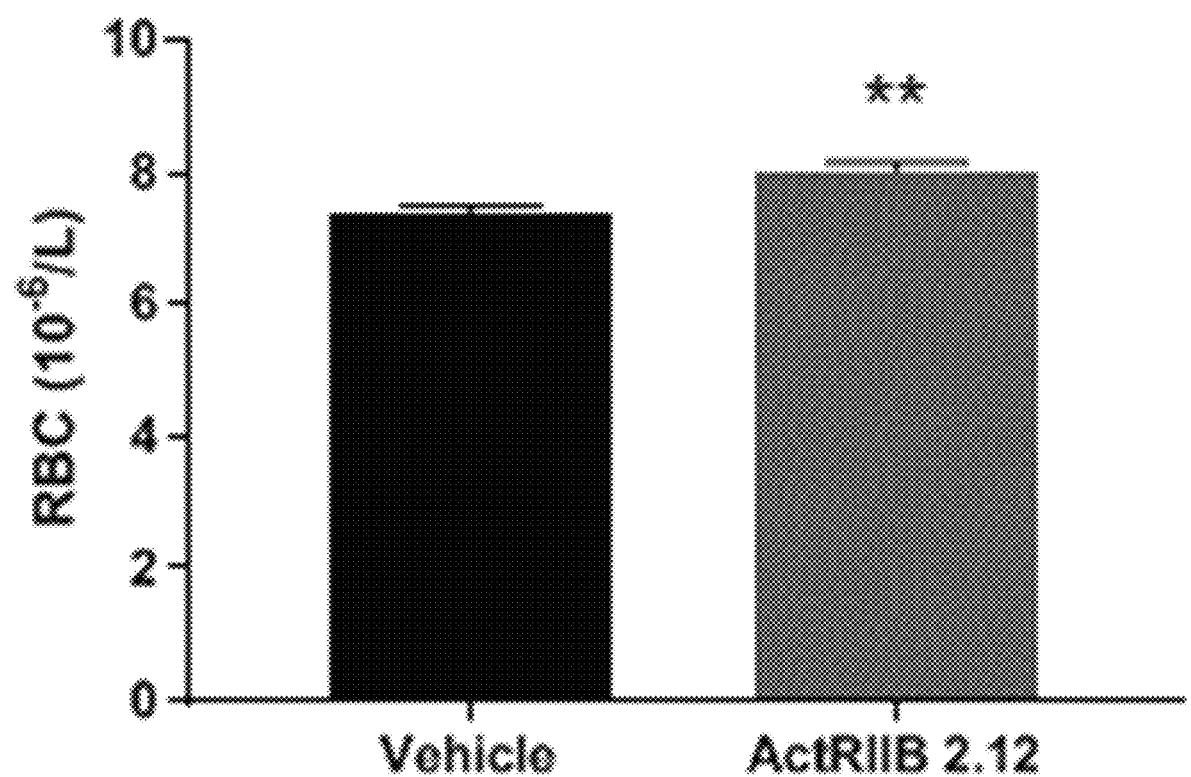
Figure 7B:
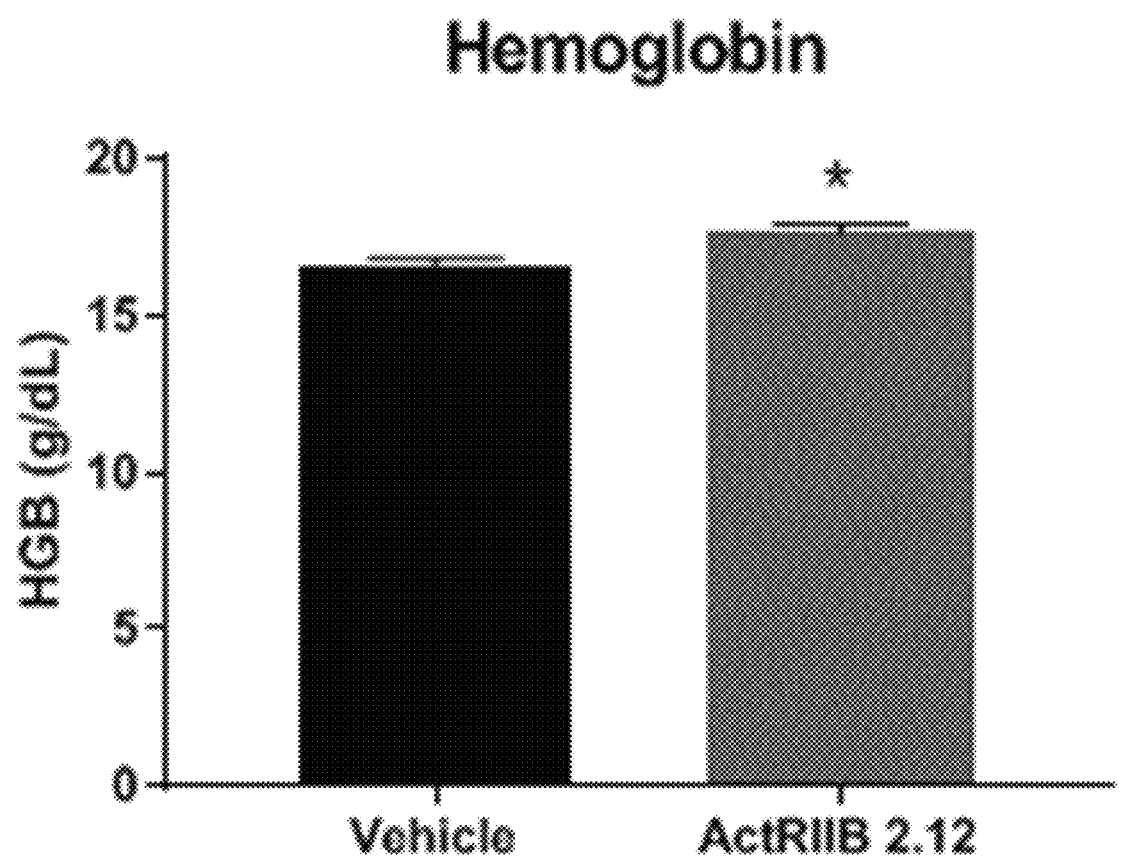
Figure 8B:
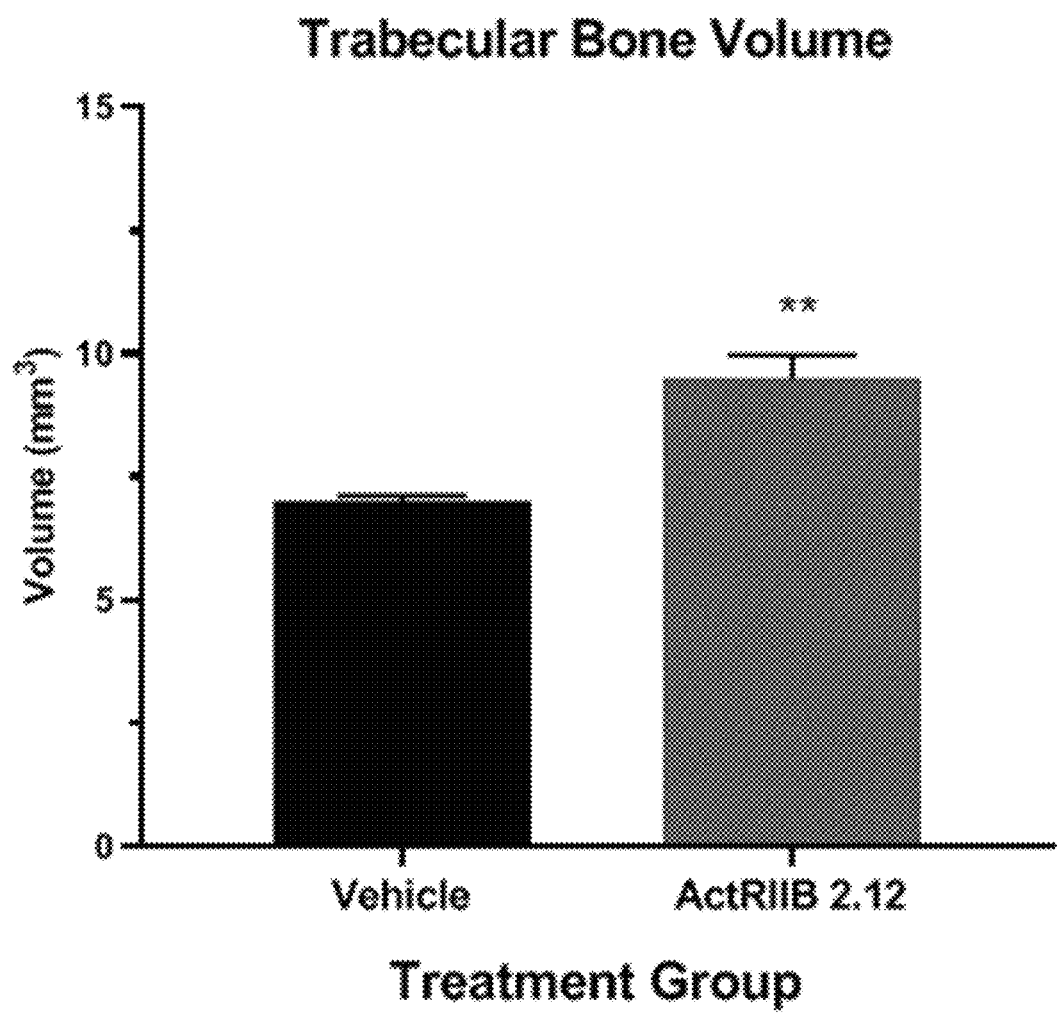
Figure 8C:
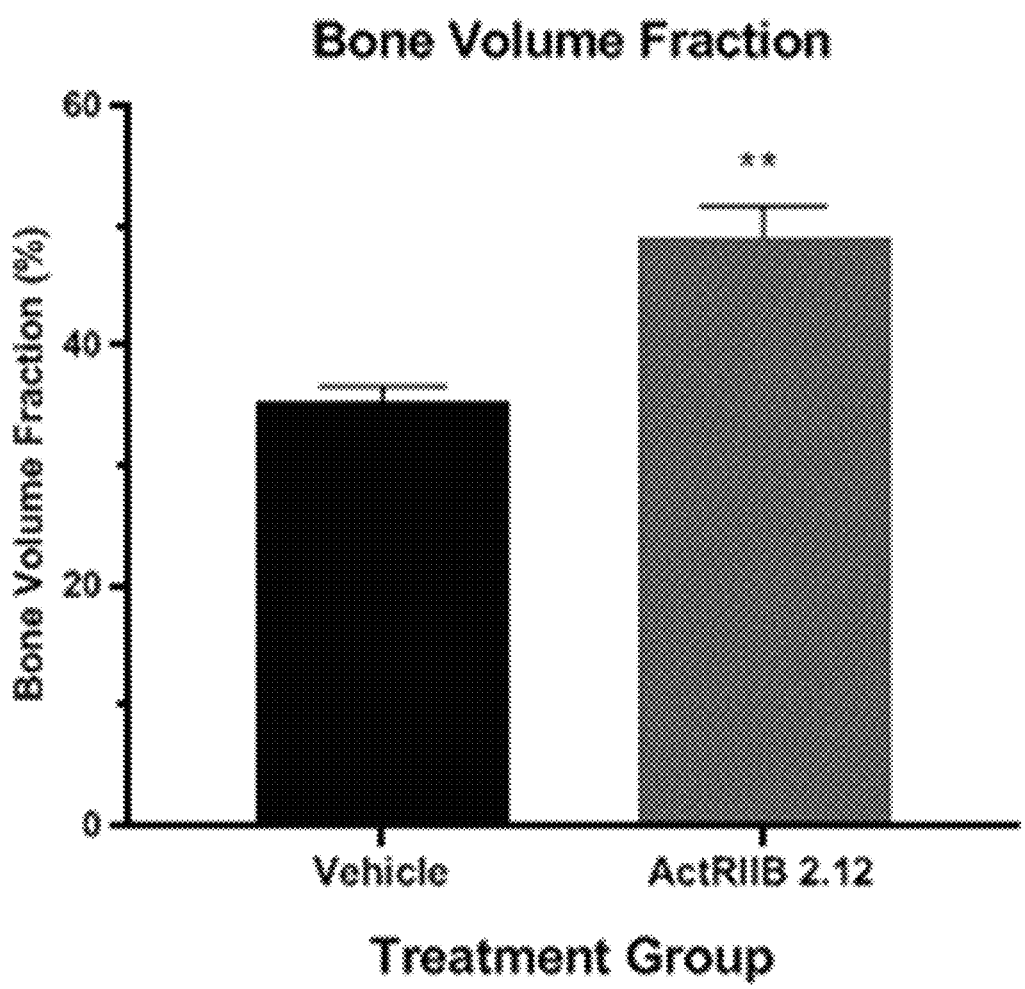
Figure 8D:
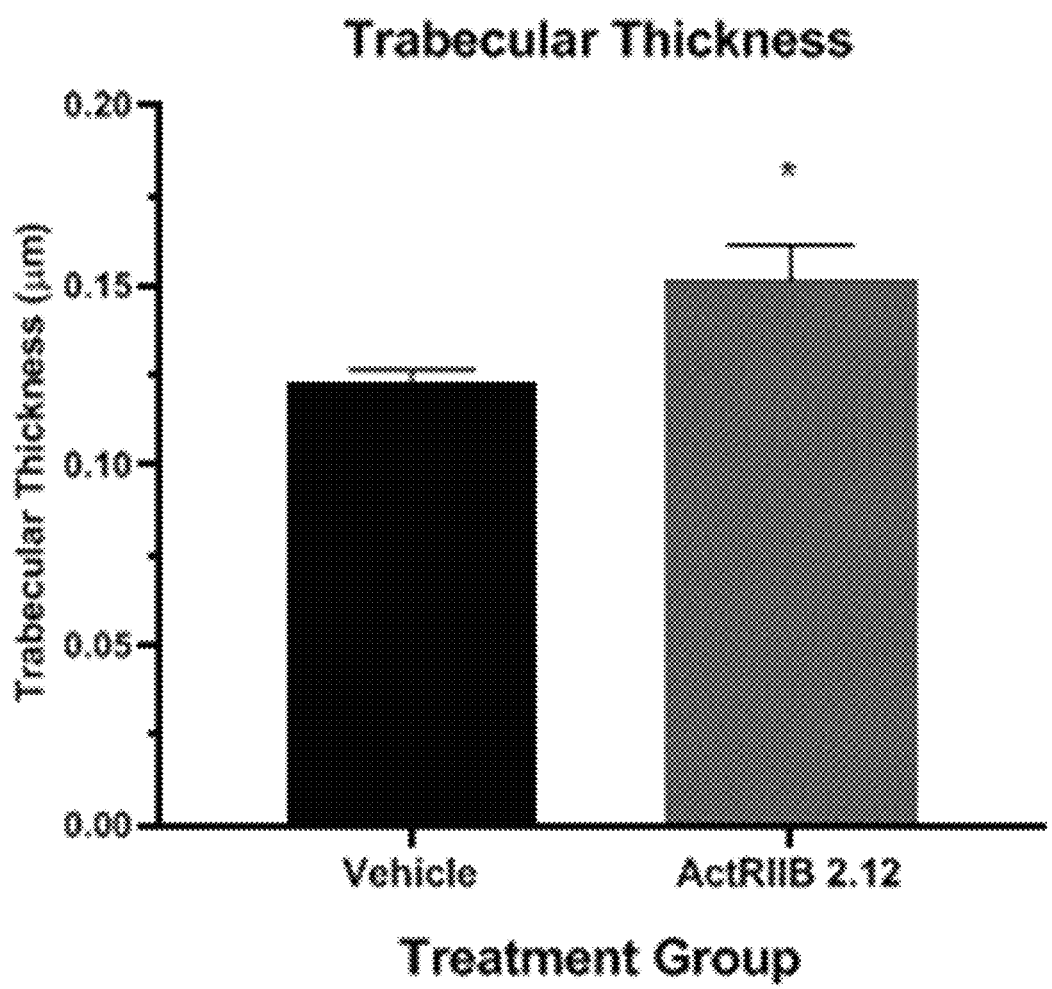
Figure 8E:
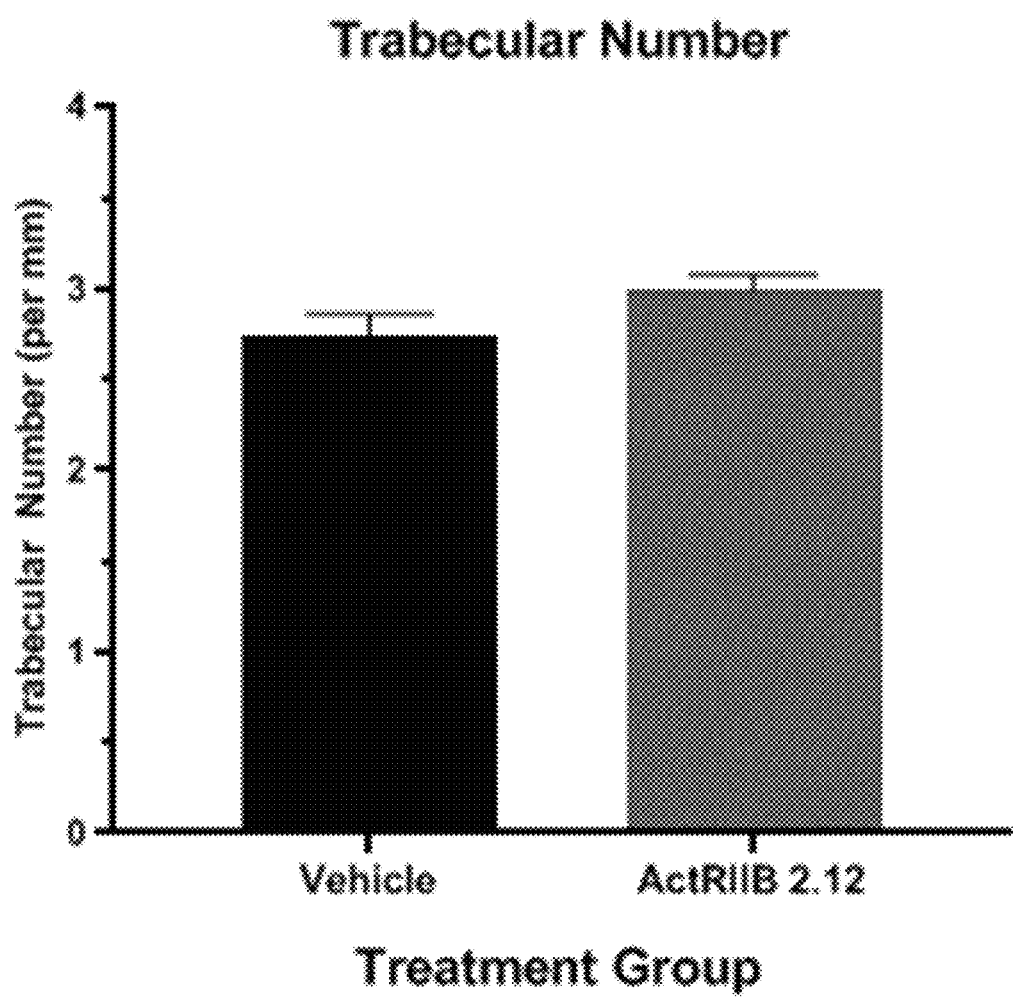

Example 10—Effect of ActRIIB Variant 2.12 on Red Blood Cell Mass and Trabecular Bone in Rats A hydrodynamic injection of ActRIIB 2.12 (SEQ ID NO: 15)-Fc plasmid DNA was delivered via lateral tail vein injection to four-week old Sprague Dawley rats. Four weeks after injection, blood was analyzed for hematology parameters and ActRIIB 2.12-Fc levels. MicroCT imaging (Perkin Elmer Quantum Fx) was performed ex vivo on the tibia. ASBMR bone morphometry parameters of each dataset were calculated with AnalyzePro software (Analyze Direct, Overland Park KS) using the Bone Morphometry Analysis Add-on. A 150-slice region of CT volume immediately distal to the proximal tibial growth plate was selected to assess changes in trabecular bone parameters. As shown in FIGS. 7A-7C, ActRIIB 2.12-Fc increased parameters of red cell mass in wild-type rats (*=p<0.05; **=p<0.01), including red blood cell counts, hemoglobin levels, and hematocrit. ActRIIB 2.12-Fc also increased trabecular bone (trabecular bone volume, trabecular bone fraction, and trabecular thickness) in wild-type rats (FIGS. 8A-8E; *=p<0.05; **=p<0.01). These data indicate that treatment with ActRIIB 2.12-Fc in wild-type rats increases trabecular bone mass.

Example 11—Treatment of Muscle Disease by Administration of an Extracellular ActRIIB Variant According to the methods disclosed herein, a physician of skill in the art can treat a subject, such as a human patient, having muscle disease (e.g., DMD, ALS, or inclusion body myositis) so as to increase muscle mass or maintain or improve muscle strength (e.g., reduce muscle weakness). The method of treatment can include diagnosing or identifying a subject as a candidate for treatment based on standard clinical tests for muscle diseases (e.g., blood test, muscle biopsy, genetic test, and/or electromyogram). To treat the subject, a physician of kill in the art can administer to the subject a composition containing an extracellular ActRIIB variant (e.g., an extracellular ActRIIB variant having the sequence of any one of SEQ ID NOs: 1-15 (e.g., SEQ ID NOs: 2-15)). The composition containing the extracellular ActRIIB variant may be administered to the subject, for example, by parenteral injection (e.g., intravenous injection) or by local administration (e.g., injection into the muscle) to treat muscle disease. The extracellular ActRIIB variant (e.g., an extracellular ActRIIB variant having the sequence of any one of SEQ ID NOs: 1-15 (e.g., SEQ ID NOs: 2-15)) is administered in a therapeutically effective 5 amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the extracellular ActRIIB variant is administered bimonthly, once a month, once every two weeks, or at least once a week or more (e.g., 1, 2, 3, 4, 5, 6, or 7 times a week or more). The extracellular ActRIIB variant is administered in an amount sufficient to increase muscle mass or maintain or improve muscle strength (e.g., reduce muscle weakness).

Following administration of the composition to a patient, a practitioner of skill in the art can monitor the patient's improvement in response to the therapy by a variety of methods. For example, a physician can monitor the patient's muscle mass, muscle strength, and motor function. A finding that the patient exhibits increased muscle mass or maintains or improves muscle strength following administration of the composition compared to test results prior to administration of the composition indicates that the patient is responding favorably to the treatment. Subsequent doses can be determined and administered as needed.

Example 12—Treatment of Bone Disease by Administration of an Extracellular ActRIIB variant According to the methods disclosed herein, a physician of skill in the art can treat a subject, such as a human patient, having bone disease (e.g., osteoporosis or osteopenia) so as to increase bone mineral density, increase bone formation, reduce bone resorption, reduce bone loss, or reduce the risk of bone fracture. The method of treatment can include diagnosing or identifying a subject as a candidate for treatment based on standard clinical tests for bone mineral density (e.g., dual X-ray absorptiometry). To treat the subject, a physician of kill in the art can administer to the subject a composition containing an extracellular ActRIIB variant (e.g., an extracellular ActRIIB variant having the sequence of any one of SEQ ID NOs: 1-15 (e.g., SEQ ID NOs: 2-15)). The composition containing the extracellular ActRIIB variant may be administered to the subject, for example, by parenteral injection (e.g., intravenous injection) to treat bone disease. The extracellular ActRIIB variant (e.g., an extracellular ActRIIB variant having the sequence of any one of SEQ ID NOs: 1-15 (e.g., SEQ ID NOs: 2-15)) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the extracellular ActRIIB variant is administered bimonthly, once a month, once every two weeks, or at least once a week or more (e.g., 1, 2, 3, 4, 5, 6, or 7 times a week or more). The extracellular ActRIIB variant is administered in an amount sufficient to increase bone mineral density, increase bone formation, reduce bone resorption, reduce bone loss, or reduce the risk of bone fracture.

Following administration of the composition to a patient, a practitioner of skill in the art can monitor the patient's improvement in response to the therapy by a variety of methods. For example, a physician can monitor the patient's bone mineral density by performing dual X-ray absorptiometry. A finding that the patient exhibits increased bone mineral density, increased bone formation, reduced bone resorption, reduced bone loss, or a reduced risk of bone fracture following administration of the composition compared to test results prior to administration of the composition indicates that the patient is responding favorably to the treatment. Subsequent doses can be determined and administered as needed.

Example 13—Treatment of Anemia by Administration of an Extracellular ActRIIB Variant According to the methods disclosed herein, a physician of skill in the art can treat a subject, such as a human patient, having anemia (e.g., vitamin deficiency anemia or anemia associated with chronic kidney disease) so as to increase a parameter of red cell mass, such as red blood cell count, hemoglobin levels, or hematocrit. The method of treatment can include diagnosing or identifying a subject as a candidate for treatment based on a blood test measuring hematological parameters. To treat the subject, a physician of kill in the art can administer to the subject a composition containing an extracellular ActRIIB variant (e.g., an extracellular ActRIIB variant having the sequence of any one of SEQ ID NOs: 1-15 (e.g., SEQ ID NOs: 2-15)). The composition containing the extracellular ActRIIB variant may be administered to the subject, for example, by parenteral injection (e.g., intravenous injection) to treat anemia. The extracellular ActRIIB variant (e.g., an extracellular ActRIIB variant having the sequence of any one of SEQ ID NOs: 1-15 (e.g., SEQ ID NOs: 2-15)) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the extracellular ActRIIB variant is administered bimonthly, once a month, once every two weeks, or at least once a week or more (e.g., 1, 2, 3, 4, 5, 6, or 7 times a week or more). The extracellular ActRIIB variant is administered in an amount sufficient to increase hemoglobin levels, increase red blood cell counts, or increase hematocrit.

Following administration of the composition to a patient, a practitioner of skill in the art can monitor the patient's improvement in response to the therapy by a variety of methods. For example, a physician can monitor the patient's hemoglobin levels, red blood cell counts, or hematocrit by performing a blood test. A finding that the patient exhibits improved hemoglobin levels, red blood cell counts, or hematocrit following administration of the composition compared to test results prior to administration of the composition indicates that the patient is responding favorably to the treatment. Subsequent doses can be determined and administered as needed.

Example 14—Treatment of Fibrosis by Administration of an Extracellular ActRIIB Variant According to the methods disclosed herein, a physician of skill in the art can treat a subject, such as a human patient, having fibrosis (e.g., pulmonary fibrosis or fibrosis associated with chronic kidney disease) so as to reduce the symptoms of fibrosis or slow or stop the progression of fibrosis. The method of treatment can include diagnosing or identifying a subject as a candidate for treatment based on clinical tests for fibrosis (e.g., imaging tests, such as X-ray or CT scan). To treat the subject, a physician of kill in the art can administer to the subject a composition containing an extracellular ActRIIB variant (e.g., an extracellular ActRIIB variant having the sequence of any one of SEQ ID NOs: 1-15 (e.g., SEQ ID NOs: 2-15)). The composition containing the extracellular ActRIIB variant may be administered to the subject, for example, by parenteral injection (e.g., intravenous injection) to treat fibrosis, or can be locally administered (e.g., injected) to the fibrotic tissue or organ. The extracellular ActRIIB variant (e.g., an extracellular ActRIIB variant having the sequence of any one of SEQ ID NOs: 1-15 (e.g., SEQ ID NOs: 2-15)) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the extracellular ActRIIB variant is administered bimonthly, once a month, once every two weeks, or at least once a week or more (e.g., 1, 2, 3, 4, 5, 6, or 7 times a week or more). The extracellular ActRIIB variant is administered in an amount sufficient to reduce the symptoms of fibrosis or slow or stop the progression of fibrosis.

Following administration of the composition to a patient, a practitioner of skill in the art can monitor the patient's improvement in response to the therapy by a variety of methods. For example, a physician can monitor the patient's fibrosis by performing imaging tests and can monitor the patient's symptoms using standard clinical tests. A finding that the patient's symptoms are reduced or that progression of the patient's fibrosis slows or stops following administration of the composition compared to test results prior to administration of the composition indicates that the patient is responding favorably to the treatment. Subsequent doses can be determined and administered as needed.

Example 15—Treatment of Pulmonary Hypertension by Administration of an Extracellular ActRIIB Variant According to the methods disclosed herein, a physician of skill in the art can treat a subject, such as a human patient, having pulmonary hypertension (PH, e.g., PAH) so as to reduce the symptoms of PH or slow or stop the progression of PH. The method of treatment can include diagnosing or identifying a subject as a candidate for treatment based on standard clinical tests for PH (e.g., echocardiogram, electrocardiogram, chest X-ray, or right heart catheterization). To treat the subject, a physician of kill in the art can administer to the subject a composition containing an extracellular ActRIIB variant (e.g., an extracellular ActRIIB variant having the sequence of any one of SEQ ID NOs: 1-15 (e.g., SEQ ID NOs: 2-15)). The composition containing the extracellular ActRIIB variant may be administered to the subject, for example, by parenteral injection (e.g., intravenous injection) to treat PH. The extracellular ActRIIB variant (e.g., an extracellular ActRIIB variant having the sequence of any one of SEQ ID NOs: 1-15 (e.g., SEQ ID NOs: 2-15)) is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the extracellular ActRIIB variant is administered bimonthly, once a month, once every two weeks, or at least once a week or more (e.g., 1, 2, 3, 4, 5, 6, or 7 times a week or more). The extracellular ActRIIB variant is administered in an amount sufficient to reduce the symptoms of PH or slow or stop the progression of PH.

Following administration of the composition to a patient, a practitioner of skill in the art can monitor the patient's improvement in response to the therapy by a variety of methods. For example, a physician can monitor the patient's symptoms using standard clinical tests and patient self reporting. A finding that the patient's symptoms are reduced the symptoms of PH or that progression of the patient's PH slows or stops following administration of the composition compared to test results prior to administration of the composition indicates that the patient is responding favorably to the treatment. Subsequent doses can be determined and administered as needed.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are within the following claims.

```
                        SEQUENCE LISTING

Sequence total quantity: 74
SEQ ID NO: 1            moltype = AA  length = 115
FEATURE                 Location/Qualifiers
VARIANT                 11
                        note = MISC_FEATURE - Xaa is Ile or Leu
VARIANT                 12
                        note = MISC_FEATURE - Xaa is Phe or Tyr
VARIANT                 19
                        note = MISC_FEATURE - Xaa is Leu or Lys
VARIANT                 20
                        note = MISC_FEATURE - Xaa is Asp or Glu
VARIANT                 25
                        note = MISC_FEATURE - Xaa is Thr or Ser
VARIANT                 27
                        note = MISC_FEATURE - Xaa is Leu or Val
VARIANT                 29
                        note = MISC_FEATURE - Xaa is Pro or Arg
VARIANT                 31
                        note = MISC_FEATURE - Xaa is Tyr or Glu
VARIANT                 33
                        note = MISC_FEATURE - Xaa is Asp or Glu
VARIANT                 34
                        note = MISC_FEATURE - Xaa is Lys or Gln
VARIANT                 38
                        note = MISC_FEATURE - Xaa is Arg or Leu
VARIANT                 41
                        note = MISC_FEATURE - Xaa is Tyr or Phe
VARIANT                 45
                        note = MISC_FEATURE - Xaa is Arg or Lys
VARIANT                 47
                        note = MISC_FEATURE - Xaa is Ser or Ile
VARIANT                 48
                        note = MISC_FEATURE - Xaa is Ser or Thr
VARIANT                 50
                        note = MISC_FEATURE - Xaa is Ser or Thr
VARIANT                 51
                        note = MISC_FEATURE - Xaa is Ile or Leu
VARIANT                 53
                        note = MISC_FEATURE - Xaa is Ile or Leu
VARIANT                 56
                        note = MISC_FEATURE - Xaa is Lys or Gln
VARIANT                 63
                        note = MISC_FEATURE - Xaa is Phe or Ile
VARIANT                 69
                        note = MISC_FEATURE - Xaa is Gln, Thr, or Asp
VARIANT                 70
                        note = MISC_FEATURE - Xaa is Glu, Asp, or Thr
VARIANT                 74
                        note = MISC_FEATURE - Xaa is Lys or Thr
VARIANT                 75
                        note = MISC_FEATURE - Xaa is Lys or Glu
VARIANT                 76
                        note = MISC_FEATURE - Xaa is Asp or Glu
VARIANT                 77
                        note = MISC_FEATURE - Xaa is Ser or Asn
VARIANT                 79
                        note = MISC_FEATURE - Xaa is Glu or Gln
VARIANT                 89
                        note = MISC_FEATURE - Xaa is Phe or Met
source                  1..115
                        mol_type = protein
                        organism = synthetic construct
```

```
SEQUENCE: 1
GRGEAETREC XXYNANWEXX RTNQXGXEXC XGXXDKRXHC XASWXNXXGX XEXVKXGCWL    60
DDXNCYDRXX CVAXXXXPXV YFCCCEGNXC NERFTHLPEA GGPEVTYEPP PTAPT        115

SEQ ID NO: 2            moltype = AA  length = 115
FEATURE                 Location/Qualifiers
source                  1..115
                        mol_type = protein
                        organism = synthetic construct
SEQUENCE: 2
GRGEAETREC IFYNANWEKD RTNQSGLEPC YGDQDKRRHC FASWKNSSGT IELVKQGCWL    60
DDINCYDRQE CVAKKDSPEV YFCCCEGNFC NERFTHLPEA GGPEVTYEPP PTAPT        115

SEQ ID NO: 3            moltype = AA  length = 115
FEATURE                 Location/Qualifiers
source                  1..115
                        mol_type = protein
                        organism = synthetic construct
SEQUENCE: 3
GRGEAETREC IYYNANWELD RTNQSGLERC EGEQDKRLHC YASWRNSSGT IELVKKGCWL    60
DDINCYDRQE CVATKENPQV YFCCCEGNFC NERFTHLPEA GGPEVTYEPP PTAPT        115

SEQ ID NO: 4            moltype = AA  length = 115
FEATURE                 Location/Qualifiers
source                  1..115
                        mol_type = protein
                        organism = synthetic construct
SEQUENCE: 4
GRGEAETREC IYYNANWELE RTNQSGLERC EGEQDKRLHC YASWRNSSGT IELVKKGCWL    60
DDFNCYDRQE CVAKKDSPEV YFCCCEGNFC NERFTHLPEA GGPEVTYEPP PTAPT        115

SEQ ID NO: 5            moltype = AA  length = 115
FEATURE                 Location/Qualifiers
source                  1..115
                        mol_type = protein
                        organism = synthetic construct
SEQUENCE: 5
GRGEAETREC IYYNANWELE RTNQTGLERC EGEQDKRLHC YASWRNISGT IELVKKGCWL    60
DDFNCYDRQE CVAKKDSPEV YFCCCEGNFC NERFTHLPEA GGPEVTYEPP PTAPT        115

SEQ ID NO: 6            moltype = AA  length = 115
FEATURE                 Location/Qualifiers
source                  1..115
                        mol_type = protein
                        organism = synthetic construct
SEQUENCE: 6
GRGEAETREC IYYNANWELE RTNQTGLERC EGEQDKRLHC YASWRNITGT IELVKKGCWL    60
DDFNCYDRQE CVAKKDSPEV YFCCCEGNFC NERFTHLPEA GGPEVTYEPP PTAPT        115

SEQ ID NO: 7            moltype = AA  length = 115
FEATURE                 Location/Qualifiers
source                  1..115
                        mol_type = protein
                        organism = synthetic construct
SEQUENCE: 7
GRGEAETREC IYYNANWELE RTNQSGLEPC EGEQDKRLHC YASWRNSSGT IELVKKGCWL    60
DDFNCYDRQE CVAKKDSPEV YFCCCEGNFC NERFTHLPEA GGPEVTYEPP PTAPT        115

SEQ ID NO: 8            moltype = AA  length = 115
FEATURE                 Location/Qualifiers
source                  1..115
                        mol_type = protein
                        organism = synthetic construct
SEQUENCE: 8
GRGEAETREC IYYNANWELE RTNQSGLERC YGDKDKRLHC YASWRNSSGT IELVKKGCWL    60
DDFNCYDRQE CVAKKDSPEV YFCCCEGNFC NERFTHLPEA GGPEVTYEPP PTAPT        115

SEQ ID NO: 9            moltype = AA  length = 115
FEATURE                 Location/Qualifiers
source                  1..115
                        mol_type = protein
                        organism = synthetic construct
SEQUENCE: 9
GRGEAETREC IYYNANWELE RTNQSGLERC EGEQDKRLHC FASWKNSSGT IELVKQGCWL    60
DDFNCYDRQE CVAKKDSPEV YFCCCEGNFC NERFTHLPEA GGPEVTYEPP PTAPT        115

SEQ ID NO: 10           moltype = AA  length = 115
FEATURE                 Location/Qualifiers
source                  1..115
```

```
                        mol_type = protein
                        organism = synthetic construct
SEQUENCE: 10
GRGEAETREC IFYNANWEKD RTNQSGLERC EGEQDKRLHC YASWRNSSGT IELVKKGCWL    60
DDFNCYDRQE CVAKKDSPEV YFCCCEGNFC NERFTHLPEA GGPEVTYEPP PTAPT        115

SEQ ID NO: 11           moltype = AA  length = 115
FEATURE                 Location/Qualifiers
source                  1..115
                        mol_type = protein
                        organism = synthetic construct
SEQUENCE: 11
GRGEAETREC IYYNANWELE RTNQSGLERC YGDQDKRRHC YASWRNSSGT IELVKKGCWL    60
DDFNCYDRQE CVAKKDSPEV YFCCCEGNFC NERFTHLPEA GGPEVTYEPP PTAPT        115

SEQ ID NO: 12           moltype = AA  length = 115
FEATURE                 Location/Qualifiers
source                  1..115
                        mol_type = protein
                        organism = synthetic construct
SEQUENCE: 12
GRGEAETREC LYYNANWELE RTNQSGVERC EGEKDKRLHC YASWRNSSGS LEIVKKGCWL    60
DDFNCYDRTD CVATEENPQV YFCCCEGNMC NERFTHLPEA GGPEVTYEPP PTAPT        115

SEQ ID NO: 13           moltype = AA  length = 115
FEATURE                 Location/Qualifiers
source                  1..115
                        mol_type = protein
                        organism = synthetic construct
SEQUENCE: 13
GRGEAETREC LYYNANWELE RTNQSGVERC EGEKDKRLHC YASWRNSSGS LEIVKKGCWL    60
DDFNCYDRDT CVATEENPQV YFCCCEGNMC NERFTHLPEA GGPEVTYEPP PTAPT        115

SEQ ID NO: 14           moltype = AA  length = 115
FEATURE                 Location/Qualifiers
source                  1..115
                        mol_type = protein
                        organism = synthetic construct
SEQUENCE: 14
GRGEAETREC LYYNANWELE RTNQSGVERC EGEKDKRLHC YASWRNSSGS LEIVKKGCWL    60
DDFNCYDRTD CVATKENPQV YFCCCEGNMC NERFTHLPEA GGPEVTYEPP PTAPT        115

SEQ ID NO: 15           moltype = AA  length = 115
FEATURE                 Location/Qualifiers
source                  1..115
                        mol_type = protein
                        organism = synthetic construct
SEQUENCE: 15
GRGEAETREC LYYNANWELE RTNQSGVERC EGEKDKRLHC YASWRNSSGS LEIVKKGCWL    60
DDFNCYDRDT CVATKENPQV YFCCCEGNMC NERFTHLPEA GGPEVTYEPP PTAPT        115

SEQ ID NO: 16           moltype = AA  length = 109
FEATURE                 Location/Qualifiers
source                  1..109
                        mol_type = protein
                        organism = Homo sapiens
SEQUENCE: 16
GAILGRSETQ ECLFFNANWE KDRTNQTGVE PCYGDKDKRR HCFATWKNIS GSIEIVKQGC    60
WLDDINCYDR TDCVEKKDSP EVYFCCCEGN MCNEKFSYFP EMEVTQPTS              109

SEQ ID NO: 17           moltype = AA  length = 115
FEATURE                 Location/Qualifiers
source                  1..115
                        mol_type = protein
                        organism = Homo sapiens
SEQUENCE: 17
GRGEAETREC IYYNANWELE RTNQSGLERC EGEQDKRLHC YASWRNSSGT IELVKKGCWL    60
DDFNCYDRQE CVATEENPQV YFCCCEGNFC NERFTHLPEA GGPEVTYEPP PTAPT        115

SEQ ID NO: 18           moltype = AA  length = 512
FEATURE                 Location/Qualifiers
source                  1..512
                        mol_type = protein
                        organism = Homo sapiens
SEQUENCE: 18
MTAPWVALAL LWGSLCAGSG RGEAETRECI YYNANWELER TNQSGLERCE GEQDKRLHCY    60
ASWRNSSGTI ELVKKGCWLD DFNCYDRQEC VATEENPQVY FCCCEGNFCN ERFTHLPEAG   120
GPEVTYEPPP TAPTLLTVLA YSLLPIGGLS LIVLLAFWMY RHRKPPYGHV DIHEDPGPPP   180
PSPLVGLKPL QLLEIKARGR FGCVWKAQLM NDFVAVKIFP LQDKQSWQSE REIFSTPGMK   240
```

```
HENLLQFIAA EKRGSNLEVE LWLITAFHDK GSLTDYLKGN IITWNELCHV AETMSRGLSY    300
LHEDVPWCRG EGHKPSIAHR DFKSKNVLLK SDLTAVLADF GLAVRFEPGK PPGDTHGQVG    360
TRRYMAPEVL EGAINFQRDA FLRIDMYAMG LVLWELVSRC KAADGPVDEY MLPFEEEIGQ    420
HPSLEELQEV VVHKKMRPTI KDHWLKHPGL AQLCVTIEEC WDHDAEARLS AGCVEERVSL    480
IRRSVNGTTS DCLVSLVTSV TNVDLPPKES SI                                 512

SEQ ID NO: 19           moltype = AA   length = 225
FEATURE                 Location/Qualifiers
source                  1..225
                        mol_type = protein
                        organism = Homo sapiens
SEQUENCE: 19
THTCPPCPAP ELLGGPSVFL FPPKPKDTLM ISRTPEVTCV VVDVSHEDPE VKFNWYVDGV     60
EVHNAKTKPR EEQYNSTYRV VSVLTVLHQD WLNGKEYKCK VSNKALPVPI EKTISKAKGQ    120
PREPQVYTLP PSREEMTKNQ VSLTCLVKGF YPSDIAVEWE SNGQPENNYK TTPPVLDSDG    180
PFFLYSKLTV DKSRWQQGNV FSCSVMHEAL HNHYTQKSLS LSPGK                    225

SEQ ID NO: 20           moltype = AA   length = 4
FEATURE                 Location/Qualifiers
source                  1..4
                        mol_type = protein
                        organism = synthetic construct
SEQUENCE: 20
GGGA                                                                   4

SEQ ID NO: 21           moltype = AA   length = 4
FEATURE                 Location/Qualifiers
source                  1..4
                        mol_type = protein
                        organism = synthetic construct
SEQUENCE: 21
GGGS                                                                   4

SEQ ID NO: 22           moltype = AA   length = 4
FEATURE                 Location/Qualifiers
source                  1..4
                        mol_type = protein
                        organism = synthetic construct
SEQUENCE: 22
GGGG                                                                   4

SEQ ID NO: 23           moltype = AA   length = 5
FEATURE                 Location/Qualifiers
source                  1..5
                        mol_type = protein
                        organism = synthetic construct
SEQUENCE: 23
GGGGA                                                                  5

SEQ ID NO: 24           moltype = AA   length = 5
FEATURE                 Location/Qualifiers
source                  1..5
                        mol_type = protein
                        organism = synthetic construct
SEQUENCE: 24
GGGGS                                                                  5

SEQ ID NO: 25           moltype = AA   length = 5
FEATURE                 Location/Qualifiers
source                  1..5
                        mol_type = protein
                        organism = synthetic construct
SEQUENCE: 25
GGGGG                                                                  5

SEQ ID NO: 26           moltype = AA   length = 4
FEATURE                 Location/Qualifiers
source                  1..4
                        mol_type = protein
                        organism = synthetic construct
SEQUENCE: 26
GGAG                                                                   4

SEQ ID NO: 27           moltype = AA   length = 4
FEATURE                 Location/Qualifiers
source                  1..4
                        mol_type = protein
                        organism = synthetic construct
SEQUENCE: 27
```

```
GGSG                                                                                   4

SEQ ID NO: 28              moltype = AA  length = 4
FEATURE                    Location/Qualifiers
source                     1..4
                           mol_type = protein
                           organism = synthetic construct SEQUENCE: 28
AGGG                                                                                   4

SEQ ID NO: 29              moltype = AA  length = 4
FEATURE                    Location/Qualifiers
source                     1..4
                           mol_type = protein
                           organism = synthetic construct SEQUENCE: 29
SGGG                                                                                   4

SEQ ID NO: 30              moltype = AA  length = 4
FEATURE                    Location/Qualifiers
source                     1..4
                           mol_type = protein
                           organism = synthetic construct SEQUENCE: 30
GAGA                                                                                   4

SEQ ID NO: 31              moltype = AA  length = 4
FEATURE                    Location/Qualifiers
source                     1..4
                           mol_type = protein
                           organism = synthetic construct SEQUENCE: 31
GSGS                                                                                   4

SEQ ID NO: 32              moltype = AA  length = 6
FEATURE                    Location/Qualifiers
source                     1..6
                           mol_type = protein
                           organism = synthetic construct SEQUENCE: 32
GAGAGA                                                                                 6

SEQ ID NO: 33              moltype = AA  length = 6
FEATURE                    Location/Qualifiers
source                     1..6
                           mol_type = protein
                           organism = synthetic construct SEQUENCE: 33
GSGSGS                                                                                 6

SEQ ID NO: 34              moltype = AA  length = 8
FEATURE                    Location/Qualifiers
source                     1..8
                           mol_type = protein
                           organism = synthetic construct SEQUENCE: 34
GAGAGAGA                                                                               8

SEQ ID NO: 35              moltype = AA  length = 8
FEATURE                    Location/Qualifiers
source                     1..8
                           mol_type = protein
                           organism = synthetic construct SEQUENCE: 35
GSGSGSGS                                                                               8

SEQ ID NO: 36              moltype = AA  length = 10
FEATURE                    Location/Qualifiers
source                     1..10
                           mol_type = protein
                           organism = synthetic construct SEQUENCE: 36
GAGAGAGAGA                                                                            10

SEQ ID NO: 37              moltype = AA  length = 10
FEATURE                    Location/Qualifiers
source                     1..10
                           mol_type = protein
                           organism = synthetic construct
```

```
SEQUENCE: 37
GSGSGSGSGS                                                                        10

SEQ ID NO: 38          moltype = AA  length = 12
FEATURE                Location/Qualifiers
source                 1..12
                       mol_type = protein
                       organism = synthetic construct
SEQUENCE: 38
GAGAGAGAGA GA                                                                     12

SEQ ID NO: 39          moltype = AA  length = 12
FEATURE                Location/Qualifiers
source                 1..12
                       mol_type = protein
                       organism = synthetic construct
SEQUENCE: 39
GSGSGSGSGS GS                                                                     12

SEQ ID NO: 40          moltype = AA  length = 6
FEATURE                Location/Qualifiers
source                 1..6
                       mol_type = protein
                       organism = synthetic construct
SEQUENCE: 40
GGAGGA                                                                            6

SEQ ID NO: 41          moltype = AA  length = 6
FEATURE                Location/Qualifiers
source                 1..6
                       mol_type = protein
                       organism = synthetic construct
SEQUENCE: 41
GGSGGS                                                                            6

SEQ ID NO: 42          moltype = AA  length = 9
FEATURE                Location/Qualifiers
source                 1..9
                       mol_type = protein
                       organism = synthetic construct
SEQUENCE: 42
GGAGGAGGA                                                                         9

SEQ ID NO: 43          moltype = AA  length = 9
FEATURE                Location/Qualifiers
source                 1..9
                       mol_type = protein
                       organism = synthetic construct
SEQUENCE: 43
GGSGGSGGS                                                                         9

SEQ ID NO: 44          moltype = AA  length = 12
FEATURE                Location/Qualifiers
source                 1..12
                       mol_type = protein
                       organism = synthetic construct
SEQUENCE: 44
GGAGGAGGAG GA                                                                     12

SEQ ID NO: 45          moltype = AA  length = 12
FEATURE                Location/Qualifiers
source                 1..12
                       mol_type = protein
                       organism = synthetic construct
SEQUENCE: 45
GGSGGSGGSG GS                                                                     12

SEQ ID NO: 46          moltype = AA  length = 8
FEATURE                Location/Qualifiers
source                 1..8
                       mol_type = protein
                       organism = synthetic construct
SEQUENCE: 46
GGAGGGAG                                                                          8

SEQ ID NO: 47          moltype = AA  length = 8
FEATURE                Location/Qualifiers
source                 1..8
                       mol_type = protein
```

```
                        organism = synthetic construct
SEQUENCE: 47
GGSGGGSG                                                                8

SEQ ID NO: 48           moltype = AA  length = 12
FEATURE                 Location/Qualifiers
source                  1..12
                        mol_type = protein
                        organism = synthetic construct
SEQUENCE: 48
GGAGGGAGGG AG                                                           12

SEQ ID NO: 49           moltype = AA  length = 12
FEATURE                 Location/Qualifiers
source                  1..12
                        mol_type = protein
                        organism = synthetic construct
SEQUENCE: 49
GGSGGGSGGG SG                                                           12

SEQ ID NO: 50           moltype = AA  length = 15
FEATURE                 Location/Qualifiers
source                  1..15
                        mol_type = protein
                        organism = synthetic construct
SEQUENCE: 50
GGGGAGGGGA GGGGA                                                        15

SEQ ID NO: 51           moltype = AA  length = 15
FEATURE                 Location/Qualifiers
source                  1..15
                        mol_type = protein
                        organism = synthetic construct
SEQUENCE: 51
GGGGSGGGGS GGGGS                                                        15

SEQ ID NO: 52           moltype = AA  length = 5
FEATURE                 Location/Qualifiers
source                  1..5
                        mol_type = protein
                        organism = synthetic construct
SEQUENCE: 52
GGGAG                                                                   5

SEQ ID NO: 53           moltype = AA  length = 6
FEATURE                 Location/Qualifiers
source                  1..6
                        mol_type = protein
                        organism = synthetic construct
SEQUENCE: 53
GGGAGG                                                                  6

SEQ ID NO: 54           moltype = AA  length = 7
FEATURE                 Location/Qualifiers
source                  1..7
                        mol_type = protein
                        organism = synthetic construct
SEQUENCE: 54
GGGAGGG                                                                 7

SEQ ID NO: 55           moltype = AA  length = 4
FEATURE                 Location/Qualifiers
source                  1..4
                        mol_type = protein
                        organism = synthetic construct
SEQUENCE: 55
AAAL                                                                    4

SEQ ID NO: 56           moltype = AA  length = 4
FEATURE                 Location/Qualifiers
source                  1..4
                        mol_type = protein
                        organism = synthetic construct
SEQUENCE: 56
AAAK                                                                    4

SEQ ID NO: 57           moltype = AA  length = 4
FEATURE                 Location/Qualifiers
source                  1..4
```

```
                              mol_type = protein
                              organism = synthetic construct
SEQUENCE: 57
AAAR                                                                    4

SEQ ID NO: 58                 moltype = AA   length = 14
FEATURE                       Location/Qualifiers
source                        1..14
                              mol_type = protein
                              organism = synthetic construct
SEQUENCE: 58
EGKSSGSGSE SKST                                                        14

SEQ ID NO: 59                 moltype = AA   length = 12
FEATURE                       Location/Qualifiers
source                        1..12
                              mol_type = protein
                              organism = synthetic construct
SEQUENCE: 59
GSAGSAAGSG EF                                                          12

SEQ ID NO: 60                 moltype = AA   length = 12
FEATURE                       Location/Qualifiers
source                        1..12
                              mol_type = protein
                              organism = synthetic construct
SEQUENCE: 60
AEAAAKEAAA KA                                                          12

SEQ ID NO: 61                 moltype = AA   length = 18
FEATURE                       Location/Qualifiers
source                        1..18
                              mol_type = protein
                              organism = synthetic construct
SEQUENCE: 61
KESGSVSSEQ LAQFRSLD                                                    18

SEQ ID NO: 62                 moltype = AA   length = 10
FEATURE                       Location/Qualifiers
source                        1..10
                              mol_type = protein
                              organism = synthetic construct
SEQUENCE: 62
GENLYFQSGG                                                             10

SEQ ID NO: 63                 moltype = AA   length = 8
FEATURE                       Location/Qualifiers
source                        1..8
                              mol_type = protein
                              organism = synthetic construct
SEQUENCE: 63
SACYCELS                                                                8

SEQ ID NO: 64                 moltype = AA   length = 5
FEATURE                       Location/Qualifiers
source                        1..5
                              mol_type = protein
                              organism = synthetic construct
SEQUENCE: 64
RSIAT                                                                   5

SEQ ID NO: 65                 moltype = AA   length = 17
FEATURE                       Location/Qualifiers
source                        1..17
                              mol_type = protein
                              organism = synthetic construct
SEQUENCE: 65
RPACKIPNDL KQKVMNH                                                     17

SEQ ID NO: 66                 moltype = AA   length = 36
FEATURE                       Location/Qualifiers
source                        1..36
                              mol_type = protein
                              organism = synthetic construct
SEQUENCE: 66
GGSAGGSGSG SSGGSSGASG TGTAGGTGSG SGTGSG                                36

SEQ ID NO: 67                 moltype = AA   length = 17
FEATURE                       Location/Qualifiers
```

| | | |
|---|---|---|
| source | 1..17<br>mol_type = protein<br>organism = synthetic construct | |
| SEQUENCE: 67 | | |
| AAANSSIDLI SVPVDSR | | 17 |
| | | |
| SEQ ID NO: 68<br>FEATURE<br>source | moltype = AA  length = 36<br>Location/Qualifiers<br>1..36<br>mol_type = protein<br>organism = synthetic construct | |
| SEQUENCE: 68 | | |
| GGSGGGSEGG GSEGGGSEGG GSEGGGSEGG GSGGGS | | 36 |
| | | |
| SEQ ID NO: 69<br>FEATURE<br>source | moltype = AA  length = 5<br>Location/Qualifiers<br>1..5<br>mol_type = protein<br>organism = synthetic construct | |
| SEQUENCE: 69 | | |
| EAAAK | | 5 |
| | | |
| SEQ ID NO: 70<br>FEATURE<br>source | moltype = AA  length = 5<br>Location/Qualifiers<br>1..5<br>mol_type = protein<br>organism = synthetic construct | |
| SEQUENCE: 70 | | |
| PAPAP | | 5 |
| | | |
| SEQ ID NO: 71<br>FEATURE<br>source | moltype = AA  length = 246<br>Location/Qualifiers<br>1..246<br>mol_type = protein<br>organism = Homo sapiens | |
| SEQUENCE: 71 | | |
| MEWSWVFLFF LSVTTGVHSD KTHTCPPCPA PELLGGPSVF LFPPKPKDTL MISRTPEVTC | | 60 |
| VVVDVSHEDP EVKFNWYVDG VEVHNAKTKP REEQYNSTYR VVSVLTVLHQ DWLNGKEYKC | | 120 |
| KVSNKALPAP IEKTISKAKG QPREPQVYTL PPSRDELTKN QVSLTCLVKG FYPSDIAVEW | | 180 |
| ESNGQPENNY KTTPPVLDSD GSFFLYSKLT VDKSRWQQGN VFSCSVMHEA LHNHYTQKSL | | 240 |
| SLSPGK | | 246 |
| | | |
| SEQ ID NO: 72<br>FEATURE<br>source | moltype = AA  length = 11<br>Location/Qualifiers<br>1..11<br>mol_type = protein<br>organism = synthetic construct | |
| SEQUENCE: 72 | | |
| DICLPRWGCL W | | 11 |
| | | |
| SEQ ID NO: 73<br>FEATURE<br>source | moltype = AA  length = 93<br>Location/Qualifiers<br>1..93<br>mol_type = protein<br>organism = Homo sapiens | |
| SEQUENCE: 73 | | |
| GPVEVFITET PSQPNSHPIQ WNAPQPSHIS KYILRWRPKN SVGRWKEATI PGHLNSYTIK | | 60 |
| GLKPGVVYEG QLISIQQYGH QEVTRFDFTT TST | | 93 |
| | | |
| SEQ ID NO: 74<br>FEATURE<br>source | moltype = AA  length = 609<br>Location/Qualifiers<br>1..609<br>mol_type = protein<br>organism = Homo sapiens | |
| SEQUENCE: 74 | | |
| MKWVTFISLL FLFSSAYSRG VFRRDAHKSE VAHRFKDLGE ENFKALVLIA FAQYLQQCPF | | 60 |
| EDHVKLVNEV TEFAKTCVAD ESAENCDKSL HTLFGDKLCT VATLRETYGE MADCCAKQEP | | 120 |
| ERNECFLQHK DDNPNLPRLV RPEVDVMCTA FHDNEETFLK KYLYEIARRH PYFYAPELLF | | 180 |
| FAKRYKAAFT ECCQAADKAA CLLPKLDELR DEGKASSAKQ RLKCASLQKF GERAFKAWAV | | 240 |
| ARLSQRFPKA EFAEVSKLVT DLTKVHTECC HGDLLECADD RADLAKYICE NQDSISSKLK | | 300 |
| ECCEKPLLEK SHCIAEVEND EMPADLPSLA ADFVESKDVC KNYAEAKDVF LGMFLYEYAR | | 360 |
| RHPDYSVVLL LRLAKTYETT LEKCCAAADP HECYAKVFDE FKPLVEEPQN LIKQNCELFE | | 420 |
| QLGEYKFQNA LLVRYTKKVP QVSTPTLVEV SRNLGKVGSK CCKHPEAKRM PCAEDYLSVV | | 480 |
| LNQLCVLHEK TPVSDRVTKC CTESLVNRRP CFSALEVDET YVPKEFNAET FTFHADICTL | | 540 |
| SEKERQIKKQ TALVELVKHK PKATKEQLKA VMDDFAAFVE KCCKADDKET CFAEEGKKLV | | 600 |
| AASQAALGL | | 609 |

The invention claimed is:

1. A method of treating a subject having pulmonary hypertension (PH), the method comprising administering to the subject a therapeutically effective amount of a polypeptide comprising an extracellular activin receptor type IIB (ActRIIB) variant, the variant having one or more amino acid substitutions relative to the sequence of GRGEAETREC IYYNANWELE RTNQSGLERC EGEQDKRLHC YASWRNSSGT IELVKKGCWL DDFNCYDRQE CVATEENPQV YFCCCEGNFC NERFTHLPEA GGPEVTYEPP PTAPT (SEQ ID NO: 17),
   wherein the variant comprises one or more amino acid substitutions that impart reduced binding to bone morphogenetic protein 9 (BMP9) relative to wild type extracellular ActRIIB;
   wherein the variant comprises:
   (i) amino acid substitutions Q69T, E70D, I11L, L27V, Q34K, T50S, I51L, L53I, and F89M;
   (ii) amino acid substitutions Q69T, E70D, E75K, I11L, L27V, Q34K, T50S, I51L, L53I, and F89M;
   (iii) amino acid substitutions Q69D, E70T, I11L, L27V, Q34K, T50S, I51L, L53I, and F89M; or
   (iv) amino acid substitutions Q69D, E70T, E75K, I11L, L27V, Q34K, T50S, I51L, L53I, and F89M; and
   wherein the variant has at least 85% amino acid sequence identity to the sequence of SEQ ID NO: 17.

2. The method of claim 1, wherein the variant has the sequence of SEQ ID NO: 12.

3. The method of claim 1, wherein the variant has the sequence of SEQ ID NO: 13.

4. The method of claim 1, wherein the variant has the sequence of SEQ ID NO: 14.

5. The method of claim 1, wherein the variant has the sequence of SEQ ID NO: 15.

6. The method of claim 1, wherein the polypeptide further comprises an Fc domain monomer, an Fc domain, an albumin-binding peptide, a fibronectin domain, or a human serum albumin fused to the C-terminus of the polypeptide by way of a linker.

7. The method of claim 6, wherein the polypeptide comprises an Fc domain monomer fused to the C-terminus of the polypeptide by way of a linker.

8. The method of claim 7, wherein the polypeptide is in the form of a homodimer.

9. The method of claim 1, wherein the polypeptide binds to human BMP9 with a KD of 200 pM or higher.

10. The method of claim 1, wherein the polypeptide binds to human activin A with a $K_D$ of 800 µM or less.

11. The method of claim 1, wherein the polypeptide binds to human activin B with a $K_D$ of 800 µM or less.

12. The method of claim 1, wherein the PH is pulmonary arterial hypertension.

13. The method of claim 1, wherein the method reduces pulmonary vascular remodeling or vascular remodeling in the heart of the subject, reduces right ventricular hypertrophy, reduces pulmonary vascular resistance, or improves performance in the 6-minute walk test.

* * * * *

UNITED STATES PATENT AND TRADEMARK OFFICE
CERTIFICATE OF CORRECTION

PATENT NO. : 12,269,858 B2
APPLICATION NO. : 18/407929
DATED : April 8, 2025
INVENTOR(S) : Jasbir S. Seehra et al.

It is certified that error appears in the above-identified patent and that said Letters Patent is hereby corrected as shown below:

In the Claims

Column 82, Claim 9, Lines 16-17, replace "with a KD of 200 pM or higher" with --with a $K_D$ of 200 pM or higher--;

Claim 10, Line 19, replace "800 μM or less" with --800 pM or less--;

Claim 11, Line 21, replace "800 μM or less" with --800 pM or less--.

Signed and Sealed this
Fifth Day of August, 2025

Coke Morgan Stewart
*Acting Director of the United States Patent and Trademark Office*